US006025128A

United States Patent [19]
Veltri et al.

[11] Patent Number: 6,025,128
[45] Date of Patent: Feb. 15, 2000

[54] PREDICTION OF PROSTATE CANCER PROGRESSION BY ANALYSIS OF SELECTED PREDICTIVE PARAMETERS

[75] Inventors: Robert W Veltri, Oklahoma City; Michael P. Bacus, Edmond; M. Craig Miller, Guthrie; Kaveh Ashenayi, Tulsa, all of Okla.; Donald P. Coffey, Lutherville, Md.; Alan W. Partin; Jonathan I. Epstein, both of Baltimore, Md.

[73] Assignees: The University of Tulsa, Tulsa, Okla.; John Hopkins University, Baltimore, Md.; Cytodiagnostics, Inc., Oklahoma City, Okla.

[21] Appl. No.: 08/315,210

[22] Filed: Sep. 29, 1994

[51] Int. Cl.$^7$ ............................. G01N 33/574; C12Q 1/68
[52] U.S. Cl. ................................ 435/6; 435/7.23; 436/63; 436/64; 436/813
[58] Field of Search ........................ 435/7.23, 6; 436/63, 436/64, 813

[56] References Cited

PUBLICATIONS

Bartels, "Computer–Generated Diagnosis and Image Analysis," *Cancer Supplement*, 69(6):1636–1638, Mar. 1992.

Bartels et al., "A Self–Learning Computer Program for Cell Recognition," *ACTA Cytologica*, 14(8):486–494, Sep.–Oct. 1970.

Bartels et al., "Machine Learning in Quantitative Histopathology," *Analytical and Quantitative Cytology and Histology*, 10(4):299–306, Aug. 1988.

Burke et al., "Artificial Neural Networks for outcome Prediction in Cancer," World Congress on Neural Networks—San Diego, 1994 International Neural Network Society Annual Meeting, I:53–56, Jun. 1994.

Carmichael et al., "Deoxyribonucleic Acid Ploidy Analysis as a Predictor of Recurrence Following Radical Prostatectomy for Stage T2 Disease," *The Journal of Urology*, 153:1015–1019, Mar. 1995.

Criley et al., "Prospective Validation of Prognostic Factor Score (PFS) as a Predictor of PSA Recurrence After Radical Prostatectomy in 124 Men with Clinically Localized Prostate Cancer," *The Journal of Urology*, 153(4), AUA Ninetieth Annual Meeting, Apr. 1995.

D'Amico et al., "A Multivariate Analysis of Clinical and Pathological Factors That Predict for Prostate Specific Antigen Failure After Radical Prostatectomy for Prostate Cancer," *The Journal of Urology*, 154:131–138, Jul. 1995.

Diamond et al., "Computerized Image Analysis of Nuclear Shape as a Prognostic Factor for Prostatic Cancer," *The Prostate*, 3:321–332, 1982.

Epstein et al., "Correlation of Pathologic Findings with Progression After Radical Retropubic Prostatectomy," *Cancer*, 71(11):3582–3593, Jun. 1993.

Epstein et al., "Correlation of Prostate Cancer Nuclear Deoxyribonucleic Acid, Size, Shape and Gleason Grade with Pathological Stage at Radical Prostatectomy," *The Journal of Urology*, 148:87–91, Jul. 1992.

Kim et al., "Semiautomated Nuclear Shape Analysis of Prostatic Carcinoma and Benign Prostatic Hyperplasia," *Analytical and Quantitative Cytology and Histology*, 16(6): 400–414, Dec. 1994.

Mohler et al., "Nuclear Morphometry in Automatic Biopsy and Radical Prostatectomy Specimens of Prostatic Carcinoma, A Comparison," *Analytical and Quantitative Cytology and Histology*, 16(6):415–420, Dec. 1994.

Oberholzer et al., "Some Fundamental Aspects of Morphometry in Clinical Pathology, Demonstrated on a Simple, Multipurpose Analysis System," *Analytical and Quantitative Cytology and Histology*, 13(5):316–320, Oct. 1991.

Partin et al., "A Comparison of Nuclear Morphometry and Gleason Grade as a Predictor of Prognosis in Stage A2 Prostate Cancer: A Critical Analysis," *The Journal of Urology*, 142:1254–1258, Nov. 1989.

Peller et al., "Sextant Prostate Biopsies, A Histopathologic Correlation with Radical Prostatectomy Specimens," *Cancer*, 75(2):530–538, Jan. 1995.

Sherwood et al., "Feature Selection in Cell Image Analysis: Use of the ROC Curve," *ACTA Cytologica*, 20(3):255–261, May–Jun. 1976.

van den Ouden et al., "Deoxyribonucleic Acid Ploidy of Core Biopsies and Metastatic Lymph Nodes of Prostate Cancer Patients: Impact on Time to Progression," *The Journal of Urology*, 150:400–406, Aug. 1993.

Veltri et al., Correlation of Chromatin Complexity, DNA content, HER–2–neu, PD–41, and PCNA with Prostate Cancer Organ–Confined Disease Status, Proceedings American Asociation for Cancer Research, 86th Annual Meeting, Toronto, Ontario, Canada, vol. 36, Mar. 1995.

Veltri et al., "Multivariate Statistical Modeling of Biomarkers as Predictors of Recurrence Following Radical Prostatectomy," American Urological Association, Inc., 1994 Annual Meeting, San Francisco, CA, Oct. 1993.

(List continued on next page.)

*Primary Examiner*—Toni R. Scheiner
*Attorney, Agent, or Firm*—Arnold, White & Durkee

[57] ABSTRACT

A method for screening individuals at risk for prostate cancer progression is disclosed. The method is useful for evaluating cells from patients at risk for recurrence of prostate cancer following surgery for prostate cancer. Specifically, the method uses specific Markovian nuclear texture factors, alone or in combination with other biomarkers, to determine whether the cancer will progress or lose organ confinement. In addition, methods of predicting the development of fatal metastatic disease by statistical analysis of selected biomarkers is also disclosed. The invention also contemplates a method that uses a neural network to analyze and interpret cell morphology data. Utilizing Markovian factors and other biomarkers as parameters, the network is first trained with a sets of cell data from known progressors and known non-progressors. The trained network is then used to predict prostate cancer progression in patient samples.

31 Claims, 30 Drawing Sheets

OTHER PUBLICATIONS

Veltri et al., "Quantitative Nuclear Morphometry, Markovian Texture Descriptors, and DNA Content Captured on a CAS–200 Image Analysis System, Combined with PCNA and HER–2/neu Immunohistochemistry for Prediction of Prostate Cancer Progression," *Journal of Cellular Biochemistry Supplement*, 19:249–258, 1994.

Wang et al., "Morphometry of Nuclei of the Normal and Malignant Prostate in Relation to DNA Ploidy," *Analytical and Quantitative Cytology and Histology*, 14(3):210–216, Jun. 1992.

Wied et al., "Image Analysis in Quantitative Cytopathology and Histopathology," *Human Pathology*, 20(6):549–571, Jun. 1989.

Stozka et al., "A Hybrid Neural and Statistical Classifier System for Histopathologic Grading of Prostatic Lesions," *Analytical and Quantitative Cytology and Histology*, 17(3):204–218, Jun. 1995.

Ashenayi et al., "Gaussian Perceptron Capable of Classifying "2N+1" Distinct Classes of Input Patterns," *Control and Computers*, 20(2):54–59, 1992.

Bibbo et al., "Architectural, Morphometric and Photometric Features and Their Relationship to the Main Subjective Diagnostic Clues in the Grading of Prostatic Cancer," *Analytical and Quantitative Cytology and Histology*, 12(2):85–90, 1990.

Bostwick et al., "Staging of Early Prostate Cancer: A Proposed Tumor Volume–Based Prognostic Index," *Scientific Articles*, 41(5):403–411, 1993.

Christen et al., "Chromatin Texture Features in Hematoxylin and Eosin–Stained Prostate Tissue," *Analytical and Quantitative Cytology and Histology*, 15(6):383–387, 1993.

Dawson et al., "Chromatin Texture Measurement by Markovian Analysis Use of Nuclear Models to Define and Select Texture Features," *Analytical and Quantitative Cytology and Histology*, 15(4):227–235, 1993.

Diamond et al., "A New Method to Assess Metastatic Potential of Human Prostate Cancer: Relative Nuclear Roundness," *The Journal of Urology*, 128:729–734, 1982.

Irinopoulou et al., "Toward Objective Prognostic Grading of Prostatic Carcinoma Using Image Analysis," *Analytical and Quantitative Cytology and Histology*, 15(5):341–344, 1993.

Mohler et al., "Nuclear Roundness Factor Measurement for Assessment of Prognosis of Patients with Prostatic Carcinoma. I. Testing of a Digitization System," *The Journal of Urology*, 139:1080–1084, 1988.

Mohler et al., "Nuclear Roundness Factor Measurement for Assessment of Prognosis of Patients with Prostatic Carcinoma. II. Standardization of Methodology for Histologic Sections," *The Journal of Urology*, 139: 1085–1090, 1988.

Narayan et al., "Automated Image Analysis—a New Technique to Predict Metastatic Potential of Prostate Carcinomas," *J. Urol.*, 141(4 part of 2):183, Abstract, 1989.

Oesterling, "Prostate Specific Antigen: A Critical Assessment of the Most Useful Tumor Marker for Adenocarcinoma of the Prostate," *The Journal of Urology*, 145:907–923, 1991.

Partin, "Serum PSA After Anatomic Radical Prostatectomy," *Prostatic Tumor Markers*, 20(4):713–725, 1993.

Partin, "Use of Nuclear Morphometry, Gleason Histologic Scoring, Clinical Stage, and Age to Predict Disease–Free Survival Among Patients with Prostate Cancer," *Cancer*, 70(1):161–168, 1992.

Partin, "The Use of Prostate Specific Antigen, Clinical Stage and Gleason Score to Predict Pathological Stage in Men with Localized Prostate Cancer," *The Journal of Urology*, 150:110–114, 1993.

Pressman, "Markovian Analysis of Cervical Cell Images," *The Journal of Histochemistry and Cytochemistry*, 24(1):138–144, 1976.

PCNA Scoring:
Carrol et al. method; number of positive nuclei per 1000 nuclei scored in 40X fields within JHH pathologist confirmed cancerous areas
Cases without areas dotted for cancer: 3184-17109, 3184-22048, 3185-02004, 4182-18558, 3186-03135
PD-41 Scoring:
Positive staining ducts versus total number of ducts in JHH pathologist confirmed cancerous areas
Cases with part of dotted tumor area missing: 3185-20076A

DNA1:
0 - Diploid
1 - ONR: Hypodiploid/****
2 - ONR: >S+G2M/****
3 - Ab: >S+G2M/****
4 - Ab: Aneuploid/****

DNAIO:
0 - Hypodiploid, Diploid (0-1)
1 - ONR: >S+G2M(2)
2 - Ab: >S+G2M, Tetraploid, Aneuploid (3-5)

DNA10:
0 - Normal, ONR (0-2)     1 - Abnormal (3-5)

H2NInt:
0 - No definite staining of the cytoplasm in cancer area.
1 - Definite but faint staining of the cytoplasm in the cancer area.
2 - Moderate staining intensity of all cells within the cancer area with minor variations in staining intensity.
3 - Moderate to strong staining intensity of all cells within the cancer area with minor variations in staining intensity.
4 - Uniform strong staining of all cells in the cancer area.
Cases without areas dotted for cancer: 3184-17109, 3184-22048,

H2NFDN:
0 = Negative
1 = Focal Staining (<30%)    2 = Diffuse Staining

FIG. 28B

PREDICTION OF PROSTATE CANCER PROGRESSION BY ANALYSIS OF SELECTED PREDICTIVE PARAMETERS

The government may own rights in the present invention pursuant grant number P50-CA58236-02 from the National Institutes of Health.

BACKGROUND OF THE INVENTION

1. Field of the Invention

The present invention relates to fields of computer-assisted quantitative image analysis and methods to classify cells related to cancer progression. More specifically, it concerns methods to detect patients at risk for progression following radical surgery that have been diagnosed with localized prostate cancer by current state of the art clinical pathology and clinical laboratory methodology. Additionally, it concerns using the same approach to predict organ confined disease status using pre-treatment information extracted from the core biopsy materials.

2. Description of the Related Art

Prostate cancer is diagnosed in 100/100,000 white males and in 70.1/100,000 black males in the United States. It is the second leading cause of male cancer deaths and the most commonly diagnosed cancer in men in the United States representing 21% of all newly diagnosed cancers. In 1993 an estimated 165,000 men in the United States were diagnosed with clinically apparent prostate cancer and 35,000 will succumb to the disease. The age-specific increase in incidence achieves a maximum of 1000/100,000 in men >75 years of age. The lifetime risk of developing clinical prostate cancer in the U.S. is 8.7% for white and 9.4% for black Americans with a lifetime risk of dying being 2.6% and 4.3% respectively. The risk of developing prostate cancer has risen 42.6% since 1975 as compared to an increase of only 26% in risk of developing lung cancer for that same time period. Approximately 65% of prostate cancers are clinically localized at the time of diagnosis and potentially curable with standard surgical techniques, yet only 50% of men are found to have disease confined to the prostate at the time of surgery. Pack and Spitz (Pack R. and Spitz M. A. The Cancer Bulletin, 45:384–388, 1993), reviewing the epidemiology of prostate cancer, indicated several definable risk factors such as age, race, dietary fat consumption, vasectomy, and familial aggregation with at least a two-fold increased risk for first generation relatives of men with prostate cancer (rare autosomal dominant inheritance). These causal correlations, though impressive, can not yet explain the complex etiology, biologic heterogeneity, and rapidly increasing incidence of this disease, and await further investigations of genetic, epigenetic and environmental factors.

The mortality rate for prostate cancer has been steadily increasing over the past 40 years and will continue to do so as our population ages. This clinically evident disease represents only the tip of the iceberg in that nearly 30 percent of all men over age 50 harbor a silent microscopic form of latent prostate cancer. Current early detection methods are increasing the numbers of this latent form of cancer identified, which now represent more than 11 million cases within the male population in the United States, and growth rate studies indicate that these tumors appear to grow very slowly and the great majority should remain clinically silent.

Recent advancements in transrectal ultrasonography and the development of a serum based assay (prostate specific antigen, PSA) for early detection has caused the diagnosis of premalignant neoplasias as well as prostate cancer to increase at an alarming rate. Many of these newly diagnosed neoplasias could represent the non-aggressive, potentially latent form of the disease that may never have become clinically evident if followed without therapy. Unfortunately, no accurate and specific methods presently exist to distinguish the more potentially aggressive form of prostate cancer from the latent form of the disease; thus most patients diagnosed are presently treated as though they had the aggressive form of the disease. At present, the factors to be considered in assessing cancer progression are estimates and significance of tumor volume, pre- and post-operative histological grading of cancer and high grade intraepithelial neoplasia, clinical and pathological stage, and serum prostate specific antigen (PSA) to predict biological aggressiveness of prostate cancer. These techniques generally have only marginal predictive value.

It is well accepted that the epigenetic and genetic transformation of a normal prostatic epithelial cell to a cancer cell with progression to a metastatic phenotype requires multiple steps. The development of methods to quantify accurately these changes in order to better predict tumor aggressiveness has been the subject of much experimental work in prostate cancer.

Diamond and associates (Diamond et al., Prostate, 3:321, 1982; Diamond et al., J. Urol., 128:729, 1982) were the first to employ a simple nuclear shape factor (nuclear roundness) to describe the shape of cancerous nuclei for patients with stage B1 and B2 (Whitmore-Jewett staging) prostate cancer and accurately predicted outcome for these patients. Since then several investigators have used this method to predict prognosis for patients with various stages of prostate cancer. More recently, Partin et al. (Partin et al., Cancer 70:161–168, 1992.19) used a multivariate analysis of the variance of nuclear roundness, clinical stage, Gleason score, and the patients age to predict disease free survival among a group of 100 post-operative patients with localized prostate cancer. The use of chromatin texture feature data extracted from either H&E or Feulgen stained sections correlate well to classification of malignant cells. However, the sensitivity of Markovian texture measurements is complicated by the level of pixel gray level resolution (grain). Dawson et al. (Dawson et al., Analytical and Quantitative Cytology and Histology, 15:227–35, 1993.47) used a CAS-100 Image Analysis System and software to measure 22 Markovian texture features at 20 levels of pixel resolution (grain) and found ten features that discriminated chromatin patterns in breast cancer images captured by the CAS-100. Markovian analysis is a method based on determining gray-level transition probabilities and it allows discrimination among different nuclear texture features; the value for each feature depending on the level of grain resolution for each measurement.

Christen et al. (Christen et al., Analytical Quant. Cytol. Histol., 15: 383–388, 1991) have applied a linear discriminant statistical model analysis of shape, size and texture features of H&E stained prostate nuclei to a high efficiency, 93% correct classification of normal and abnormal cells. More recently, Irinopoulou et al. (Irinopoulou et al., Analytical and Quantitative Cytology and Histology, 15: 341–44, 1993) employed Feulgen stained nuclei and a computer-assisted image analysis system to characterize digitized images (512×512 pixels, with 256 possible gray tone levels) from twenty-three patients with Stage B carcinoma of the prostate followed for at least three years. Using five chromatin texture features and discriminant analysis methodology, these patients could be divided into those with a good and poor prognosis.

In spite of the progress made in evaluating the progression of prostate cancer, it is evident that improvements are needed in the accuracy of such determinations. A particular advantage would be realized by the development of methods that provide for accurate and reproducible statistical analysis of prognostic variables to maximize the aggregate positive predictive value while simultaneously reducing false negatives and false positives.

SUMMARY OF INVENTION

The present invention provides new and improved methods for determining the biological potential for progression of treatable, localized prostate cancers using core biopsies, fine needle aspirates, or radical prostatectomy specimens in order to: (1) better evaluate which patients have tumors that need any treatment, (2) determine the prognosis of patients with prostate cancer pathologically localized to the gland, after surgery, so that adjuvant treatment of those patients with a high probability of disease progression might begin earlier in the natural course of the disease, and finally, (3) provide more objective means to select patients for chemo-prevention trials using dietary modifications, retinoids, and hormonal manipulation (i.e. 5-alpha reductase inhibitors).

For the purposes of this invention, progression is defined as recurrence of disease post-treatment (surgery or irradiation), for example in the case of prostate cancer, as determined by PSA elevation, clinical evidence of local or regional tumor recurrence, distant metastasis, or death. Organ confined disease status is defined as prostate cancer that is still contained within the prostate gland and has not invaded the prostatic capsule.

In certain embodiments of the invention, a statistically analyzed combination that includes quantitative nuclear image features selected from pathologically important tissue sections and appropriately selected biomarkers provides an aggregate positive predictive value with negligible false negatives and false positives that exceeds current conventional pathological methods. In addition, this approach affords the probability of identifying additional potential utilities for biomarkers to identify progressors with pathologically defined low to moderate Gleason score ($\leq 6$) as being of higher risk due to the presence of such biomarkers. Also, select biomarkers served to identify tumors that have extended beyond the prostate gland (non-organ confined disease). The aggregate positive predictive power of the model, all parameters (i.e. quantitative nuclear image features and biomarkers), was achieved using clinically and pathologically well defined, long term (>7 years follow-up) retrospective patient samples. The ultimate goal of this invention is to apply these predictive capabilities to prostate biopsies (both progression and organ confined disease status) and/or post-surgery prostatectomy samples (progression risk only).

This invention provides a method to collect nuclear images and extract all relevant nuclear morphometric descriptors (NMD's), including size, shape, texture (Markovian analysis), and DNA content features. Additionally, other phenotypic cancer cell properties were assessed through the use of antibody probes for cellular biomarkers (e.g. Her-2/neu, Feulgen DNA stain, PD-41 (prostate mucin antigen), etc.). The NMD's combined with the biomarkers can then be analyzed to construct a non-parametric, non-linear mathematical model (e.g. Applying statistical methods such as logistic regression; discriminate analysis (Bayesian classifier or Fischer analysis); recursive partitioning methods (Classification and Regression Trees, or CART); or neural networks (both standard and proprietary)), that can yield a single predictive probability for prostate cancer progression or organ confinement, with or without conventional pathological grading. The pathologically significant areas are identified by an expert trained in the identification of abnormal cells and tissue architecture associated with malignancies of the prostate. Such abnormalities may be present in core biopsies, fine needle aspirates, or radical prostatectomy specimens that have been fixed using methods that preserve the antigenicity of the biomolecules of diagnostic significance, cellular architecture, and integrity of the deoxyribonucleic acid (DNA) or chromatin.

According to the present invention, a method of predicting prostate cancer progression or organ confined disease status is provided, comprising the steps of first obtaining a clinical sample from a subject, then analyzing cell nuclei from areas selected by pathology experts and collecting the NMD's as well as phenotypic cellular biomarker information, and thirdly, predicting prostate cancer progression or organ confined disease status using non-parametric statistical analysis of the data. Cell sampling for image analysis involves the selection of intact cell nuclei representative of the worst state of differentiation as well as, when present, well to moderately differentiated cancer cells. This provides a measure of tumor heterogeneity often present in prostate cancer. It is suggested that at least 50% of the cells analyzed be of the worst state of cellular differentiation present in the clinical sample, and that the remainder of the cancer cells analyzed represent the well to moderately differentiated cell population, if present, in the clinical sample.

In certain embodiments, the resulting data includes biomarker results (e.g. including but not limited to Her-2/neu antigenicity, PD-41 positivity, and DNA ploidy) and NMD's, calculated based on nuclear size and shape, as well as texture features derived by nearest neighbor relational analysis of individual pixel gray levels to mathematically determine several features (e.g. object sum, picograms of DNA, contrast, correlation, sum average, sum variance, difference variance, difference entropy, information measure B, product moment, and standard deviation). For the purposes of this invention, these parameters are collectively referred to as prognostic parameters.

Clinical samples obtained from patients at risk for recurrence of prostate cancer following prostatectomy are analyzed and values generated for various prognostic parameters, including the nuclear morphometric descriptors (NMD's), Her-2/neu antigenicity, PD-41 (prostate mucin antigen) positivity above a 5% cutoff, and nuclear roundness variance (NRV-DynaCell™). Summary statistics from the NMD's (e.g. standard deviation and variance) and raw data from the biomarkers are analyzed using logistic regression. The logistic regression may be applied in a univariate or multivariate mode. As used herein, multivariate analysis means that several univariately significant independent variables are jointly regressed on the same dependent variable. A dependent variable refers to a clinical outcome (e.g. Progression as determined by PSA elevation, local or regional tumor recurrence, distant metastasis, or death), or a pathological disease state (e.g. organ confinement status). Based upon significance levels, the statistical program selects only those univariately significant independent variables that contribute to the correct prediction of the dependent variable (e.g. progression or organ confined disease status). Notable is the fact that future changes in the model, such as measurement of NMD's (e.g. different magnifications for collection, improved camera resolution, etc.) and or additional biomarkers, may change the parameters needed and only improve upon the predictive power of the models by small percentages so it may approach 100%.

As used herein, a receiver operating characteristic (ROC) curve plots an independent variable's sensitivity (true positive fraction) on the y-axis against 1-specificity (the false positive fraction) on the x-axis as the cutoff value for a predicted positive observation is varied. A positive observation means that the predicted probability is greater than or equal to an investigator selected cutoff value. The ROC curve or plot is useful for determining the sensitivity, specificity, and negative and positive predictive values of a single test or a multiparameter test. In addition, the ROC curve can be used to establish the optimum threshold cutoff for a continuous variable. When quantitating the area under a ROC curve, an area of 1.0 means a perfect predictive value, while an area of 0.5 means no predictive value and is due to random chance alone.

For the purposes of the invention, sensitivity is the fraction of observed positive cases that are correctly classified and equals: true positives÷{true positives+false negatives}. The positive predictive value equals: true positives÷{true positives+false positives}.

Specificity is the fraction of observed negative cases that are correctly classified and equals: true negatives÷{true negatives+false positives}. The negative predictive value equals: true negatives+{true negatives+false negatives}.

As used herein, Markovian analysis means a process by which an image (pattern space) is transformed into a transitional-probability space. The Markovian approach to texture measurement treats images as stochastic processes in the form of discrete Markovian fields, yielding matrices of gray-level transition probabilities. These probabilities are arrays of numbers that describe digital images in terms of the probability of occurrence of different gray levels and sequences of gray levels. The current invention uses 22 texture parameters calculated from such matrices.

Texture is an important visual feature for many pattern recognition tasks. As used herein, texture describes the interdependent characteristics of pixels within a neighboring area. Regular texture has more or less periodic patterns, while random texture is best described by its "coarseness". A texture parameter is a local statistic, meaning that the statistic is computable from a set of neighboring picture points in a neighborhood that is small compared to the number of picture points in the entire region.

A Markovian matrix of the present invention is constructed using a cell nucleus image captured in the QDA Morphology mode of the CMP v3.0 software on a CAS-200 Image Analysis System. Using the QDA Morphology mode of CMP v3.0 software allows the measurement and calculation of the features listed in Table I. CMP v3.0 calculates 22 different Markovian nuclear descriptors based upon the gray-level transition probabilities of Feulgen stained nuclei. The step size selected may range from 1 pixel to 256 pixels. The step size defines the size of the "grain" or picture point in number of pixels that is to be compared to the neighboring picture points. Each cell nucleus image is normalized by partitioning the image into eight equally frequent gray level ranges, each range consisting of an equal number of pixels. This normalization process is done by first plotting each individual pixel optical density (gray level) that is above an operator set threshold against the number of pixels. This plot is divided into eight equally frequent gray-level ranges (optical density ranges); each range containing an equal number of pixels (FIG. 1A and FIG. 1B). This yields a normalized cell nucleus image consisting of pixels with gray-level values ranging from 0–7.

TABLE I

Nuclear Morphometric Descriptors Measured Using CMP v3.0 in the QDA Morphology Mode 1. (OBSD) Object Sum OD
2. (OBSZ) Object Size
3. (OBSH) Object Shape
4. Picograms of DNA
5. (TXA001) Angular Second Moment
6. (TXB001) Contrast
7. (TXC001) Correlation
8. (TXD001) Difference Moment
9. (TXE001) Inverse Difference Moment
10. (TXF001) Sum Average
11. (TXG001) Sum Variance
12. (TXH001) Sum Entropy
13. (TXI001) Entropy
14. (TXJ001) Difference Variance
15. (TXK001) Difference Entropy
16. (TXL001) Information Measure A
17. (TXM001) Information Measure B
18. (TXN001) Maximal Correlation Coeff.
19. (TXO001) Coefficient of Variation
20. (TXP001) Peak Transition Probability
21. (TXQ001) Diagonal Variance
22. (TXR001) Diagonal Moment
23. (TXS001) Second Diagonal Moment
24. (TXT001) Product Moment
25. (TXU001) Triangular Symmetry
26. (TXV001) Blobness
27. (TXW) Standard Deviation
28. Cell Classification
   (1 = Hypodiploid, 2 = Diploid,
   3 = S-Phase, 5 = Tetraploid,
   6 = Hyperploid)

NOTE:
Values 5–25 are grain dependent Markovian texture features. Grain may be looked at as a measurement in pixels of the width of an average sized object. The grain values for all of these measurements were set to 1.

As a further step, an 8×8 gray-level transition matrix is constructed from the normalized cell nucleus image by comparing the gray-levels of neighboring picture points (e.g. if a given picture point has a normalized value of 4, and its neighboring picture point has a normalized value of 3, an entry is made in the matrix at location Row-4 and Column-3, and all of the entries at this location are summed). This matrix is then transformed into an 8×8 conditional gray-level transition probability matrix by dividing every matrix entry by the total number of pixels in the cell nucleus image. This "Markovian" probability matrix (Equation 1) is then used to compute the 22 Markovian texture features (Table I).

Equation 1

8 × 8 Conditional Grey-level

Transition Probability Matrix (Markovian)

$$M = \begin{bmatrix} P_L(0/0) & P_L(0/1) & \cdots & P_L(0/7) \\ P_L(1/0) & P_L(1/1) & \cdots & P_L(1/7) \\ \vdots & \vdots & \vdots & \vdots \\ P_L(7/0) & P_L(7/1) & \cdots & P_L(7/7) \end{bmatrix}$$

where each matrix element $P_L(i/j)$ is defined as the conditional probability of gray-level i occurring L picture points after gray-level j occurs, where L is defined as the step size (or size in pixels of the picture point).

More recently, JVB Imaging (Elmhurst, Ill.) has written a software application called ILM Morphometry v1.0 that can be applied to listmode files (*.ILM) generated using a CAS-200 Image Analysis System. This program therefore allows the measurement and calculation of the same features as the CMP v3.0 software (Markovian and DNA Content features) as well as eight additional features (listed in Table II). The inventors have already tested this new software on the patient sample reported in this invention and obtained similar statistical model performance as with the CMP v3.0 software.

TABLE II

Nuclear Morphometric Descriptors Measured Using ILM Morphometry v1.0

1. Object Sum Optical Density
2. Object Size
3. Object Shape
4. Picograms of DNA
5. Angular Second Moment
6. Contrast
7. Correlation
8. Difference Moment
9. Inverse Difference Moment
10. Sum Average
11. Sum Variance
12. Sum Entropy
13. Entropy
14. Difference Variance
15. Difference Entropy
16. Information Measure A
17. Information Measure B
18. Maximal Correlation Coefficient
19. Coefficient of Variation
20. Peak Transition Probability
21. Diagonal Variance
22. Diagonal Moment
23. Second Diagonal Moment
24. Product Moment
25. Triangular Symmetry
26. Standard Deviation
27. Cell Classification
    (1 = Hypodiploid, 2 = Diploid,
    3 = S-Phase, 5 = Tetraploid,
    6 = Hyperploid)
28. Perimeter
29. DNA Index
30. Density
31. Average Optical Density
32. Feret X
33. Feret Y
34. Maximum Diameter
35. Minimum Diameter
36. Elongation NOTE:
Values 5–25 are grain dependent Markovian texture features. Grain may be looked at as a measurement in pixels of the width of an average sized object. The grain values for all of these measurements were set to 1.

In exemplary embodiments of the invention, consideration must be given to several parameters, such as cell selection, magnification, pixel shape and size, camera resolution (number of pixels in the x and y dimension, e.g. number of pixels per $\mu m^2$), and Markovian step size, which can significantly alter nuclear morphometric descriptor outputs (FIG. 2). The NMD's have been demonstrated in this invention to be significant independent variables in the prediction of tumor progression and organ confined disease status. As previously indicated, the method for cell selection is critical because of the need to sample biologic tumor heterogeneity. Additionally, the total number of NMD's required to predict an outcome is decreased as the magnification increases (Table III; also see FIGS. 3–6), as well as significant changes in the individual NMD's required. The latter is due to an increase in the number of pixels per $\mu m^2$ that would enhance the resolution of calculations for the NMD's. Also notable, the predictive power for all outcomes using the NMD component of the model increases as the magnification increases.

TABLE III

Magnification Effects (40× vs. 63×) upon Number of Nuclear Morphometric Descriptors needed to Accurately Predict Progression in a Subset of 10 Progressors and 10 Non-Progressors

|  | 40× | | 63× | |
| --- | --- | --- | --- | --- |
|  | CMP v3.0* | JVB v1.0** | CMP v3.0* | JVB v1.0** |
| P Value Cutoff | 0.45 | 0.50 | 0.25 | 0.70 |
| Sensitivity | 90.00% | 90.00% | 100.00% | 90.00% |
| Positive Pred. Value | 90.00% | 100.00% | 76.92% | 100.00% |
| Specificity | 90.00% | 100.00% | 70.00% | 100.00% |
| Negative Pred. Value | 90.00% | 90.91% | 100.00% | 90.91% |
| # False Positives | 1 | 0 | 3 | 0 |
| # False Negatives | 1 | 1 | 0 | 1 |
| Area Under ROC Curve | 0.9400 | 0.9500 | 0.9400 | 0.9600 |

| NMD's in Model | 6 Markovian & Area | 5 Markovian & Sum O.D, Area, perimeter | 5 Markovian & Area | 4 Markovian & Sum O.D. |
| --- | --- | --- | --- | --- |
| # Concordant NMD's | 3 | | 3 | |
| # Discordant NMD's | 4 | 5 | 3 | 2 |

*Number of CMP Nuclear Morphometric Descriptors (NMD's) = 28
**Number of JVB Nuclear Morphometric Descriptors (NMD's) = 36

In other embodiments, either non-parametric statistical methods, or standard or proprietary neural networks were used to validate the utility of NMD's and biomarkers for the prediction of two possible outcomes, progression and organ confined disease status. Using a clinically and pathologically well-defined retrospective patient sample diagnosed with localized prostate cancer, logistic regression methods were applied on a well defined patient sample (n=124) (Table IV) to determine which NMD's and biomarkers were capable (e.g. statistically significant) of predicting either progression or organ confined disease status.

LOGISTIC REGRESSION PROGRESSION MODEL

The invention applies logistic regression to select the univariately significant variables for progression (Table V) using the STATA™ statistical software package (STATA™ command: logistic). Next, these univariately significant variables are multivariately assessed using backwards stepwise logistic regression (STATA™ command: swlogis) to determine which independent variables (e.g. NMD's (CMP or JVB), Gleason Score, Nuclear Roundness Variance, and biomarkers) are retained to predict progression (Tables VI, Via, VII, and VIIa).

TABLE IV

JHH-1 PATIENT SAMPLE

| | | | | |
|---|---|---|---|---|
| Average Age: | 59.6 ± 6.4 years [40–87 yrs] | Non-progressors: | 74(60%) | |
| First operation: | Jun-'75 | Progressors: | 50(40%) | |
| Last Operation: | Jun-'91 | Avg. Time to Prog: | 3.62 ± 2.1 years | |
| Time to assess: | 6.6 ± 3.1 years [1–15 yrs] | Local Recurrence: | 11(9%) | |
| Clin. Stage A1,A2 | 6% | Distant Mets: | 5(4%) | |
| Clin. Stage B1,B2 | 94% | | | |

| PATHOLOGY DIAGNOSIS | | | | GLEASON GRADING | | |
|---|---|---|---|---|---|---|
| | | | | SCORE | PRE-OP | POST-OP |
| STAGE T1b | 2(2%) | FCP+ | = 89(72%) | 2 | 0% | 1% |
| STAGE T1c | 1(1%) | FCP− | = 35(28%) | 3 | 1% | 0% |
| STAGE T2a | 72(58%) | ECP+ | = 52(42%) | 4 | 11% | 1% |
| STAGE T2b | 45(36%) | ECP− | = 72(58%) | 5 | 25% | 27% |
| STAGE T2c | 4(3%) | OC NO | = 95(77%) | 6 | 41% | 28% |
| | | OC Yes | = 29(23%) | 7 | 19% | 36% |
| | | SM+ | = 52(42%) | 8 | 2% | 6% |
| | | SM− | = 72(58%) | 9 | 0% | 1% |
| | | SV+ | = 0 | | | |
| | | LN+ | = 0 | | | |

TABLE V

Univariate Analysis for Progression Prediction using STATA ™ Logistic Regression

| Independent Variable | Statistical Significance (p Value) |
|---|---|
| Post Operative Gleason Score | p ≦ 0.00001 |
| Nuclear Roundness Variance* | p ≦ 0.00001 |
| Best CAS-200 CMP v3.0 Nuclear Morphometric Descriptors | p ≦ 0.00001 |
| Best CAS-200 JVB v1.0 Nuclear Morphometric Descriptors | p ≦ 0.00001 |
| CAS-200 DNA Ploidy - 1 (C-DNA1) | p = 0.0080 |
| CAS-200 DNA Ploidy - 10 (C-DNA10) | p = 0.0274 |
| CAS-200 DNA Ploidy - JIE (JHHDNA10) | p = 0.0109 |
| Her-2/neu Antigenicity: Focal, Diffuse, Negative (H2NFDN) | p = 0.0147 |
| PCNA Antigenicity | p = 0.1600** |
| PD-41 Antigenicity above a 5% cutoff | p = 0.3045** |

*Measured using DynaCell ™ system at Johns Hopkins Hospital
**Not Statistically Significant. Must be less than 0.0500 to be statistically significant.

TABLE VI

Univariate/Multivariate Analysis for Prostate Cancer Progression
{N = 124 Radical Prostatectomy Specimens}
Progressors/Non-Progressors: 50/74
Statistical Analysis of JHH-1 Database using Univariately Significant STDEV & VAR Statistics for CMP Texture Features, Biomarkers, Post Gleason, % JHH-NRV in Progression Prediction

| | A Post GL | B JHH-NRV | C Biomarkers (n = 3)** | D2 CMP Nuclear Descriptors (n = 12)* | H CMP Nuclear Descriptors (n = 13*) Post GL | I CMP Nuclear Descriptors (n = 10)* JHH-NRV | J CMP Nuclear Descriptors (n = 13)* JHH-NRV Post GL | K CMP Nuclear Descriptors (n = 12)* Biomarkers (n = 2)**** | L CMP Nuclear Descriptors (n = 12)* Biomarkers (n = 2)*** Post GL | M CMP Nuclear Descriptors (n = 10)* Biomarkers (n = 2)**** JHH-NRV | N CMP Nuclear Descriptors (n = 13)* Biomarkers (H2NFDN) JHH-NRV Post GL |
|---|---|---|---|---|---|---|---|---|---|---|---|
| Positive Cutoff (p>=#) | 0.50 | 0.35 | 0.40 | 0.35 | 0.40 | 0.40 | 0.50 | 0.45 | 0.45 | 0.45 | 0.50 |
| SENSITIVITY | 78.00% | 86.00% | 62.00% | 86.00% | 84.00% | 86.00% | 94.00% | 78.00% | 86.00% | 92.00% | 96.00% |
| Pos Predictive Value | 73.58% | 78.18% | 54.39% | 65.15% | 85.71% | 84.31% | 97.92% | 73.58% | 84.31% | 88.46% | 100.00% |
| SPECIFICITY | 81.08% | 83.56% | 64.86% | 68.92% | 90.54% | 89.04% | 98.63% | 81.08% | 89.19% | 91.78% | 100.00% |
| Neg Predictive Value | 84.51% | 89.71% | 71.64% | 87.93% | 89.33% | 90.28% | 96.00% | 84.51% | 90.41% | 94.37% | 97.33% |
| % False | 26.42% | 21.82% | 45.61% | 34.85% | 14.29% | 15.69% | 2.08% | 26.42% | 15.69% | 11.54% | 0.00% |

TABLE VI-continued

Univariate/Multivariate Analysis for Prostate Cancer Progression
{N = 124 Radical Prostatectomy Specimens}
Progressors/Non-Progressors: 50/74
Statistical Analysis of JHH-1 Database using Univariately Significant STDEV & VAR Statistics for CMP Texture Features, Biomarkers,
Post Gleason, % JHH-NRV in Progression Prediction

|  | A Post GL | B JHH-NRV | C Bio-markers (n = 3)** | D2 CMP Nuclear Descriptors (n = 12)* | H CMP Nuclear Descriptors (n = 13*) Post GL | I CMP Nuclear Descriptors (n = 10)* JHH-NRV | J CMP Nuclear Descriptors (n = 13)* JHH-NRV Post GL | K CMP Nuclear Descriptors (n = 12)* Biomarkers (n = 2)**** | L CMP Nuclear Descriptors (n = 12)* Biomarkers (n = 2)*** Post GL | M CMP Nuclear Descriptors (n = 10)* Biomarkers (n = 2)**** JHH-NRV | N CMP Nuclear Descriptors (n = 13)* Biomarkers (H2NFDN) JHH-NRV Post GL |
|---|---|---|---|---|---|---|---|---|---|---|---|
| Positives % False Negatives | 15.49% | 10.29% | 28.36% | 12.07% | 10.67% | 9.72% | 4.00% | 15.49% | 9.59% | 5.63% | 2.67% |
| Area Under ROC Curve | 0.8262 | 0.8975 | 0.7108 | 0.8557 | 0.9154 | 0.9556 | 0.9885 | 0.8857 | 0.9368 | 0.9726 | 0.9915 |
| Significance | <0.00001 | <0.00001 | 0.0009 | <0.00001 | <0.00001 | <0.00001 | <0.00001 | <0.00001 | <0.00001 | <0.00001 | <0.00001 |

*NOTE: n = number of CMP Nuclear Descriptors which survived the model, either Std. Deviation or Variance or both statistics.
**NOTE: Surviving Biomarkers are C-DNA1, H2NFDN, and PD41-5
***NOTE: Surviving Biomarkers are C-DNA1 and H2NFDN
****NOTE: Surviving Biomarkers are H2NFDN and PD41-5

TABLE VIa

| Feature | D1 | D2 | H | I | J | K | L | M | N |
|---|---|---|---|---|---|---|---|---|---|
| 1 | X | X | X |   | X |   |   | X | X |
| 2 | X |   | X | X | X | X |   | X | X |
| 3 | X | X | X | X | X | X | X |   | X |
| 4 | X | X | X |   | X | X | X |   | X |
| 5 |   |   |   |   |   |   |   |   |   |
| 6 | X | X |   | X | X | X | X | X | X |
| 7 | X | X | X | X | X | X | X | X | X |
| 8 | X |   | X |   |   |   | X |   |   |
| 9 |   |   |   |   |   |   |   |   |   |
| 10 | X | X | X | X | X | X | X | X | X |
| 11 | X | X | X |   | X | X | X |   | X |
| 12 |   |   |   |   |   |   |   |   |   |
| 13 |   |   |   |   |   |   |   |   |   |
| 14 | X | X | X | X | X | X | X | X | X |
| 15 | X | X | X | X | X | X | X | X | X |
| 16 |   |   |   |   |   |   |   |   |   |
| 17 | X | X | X | X | X | X | X | X | X |
| 18 |   |   |   |   |   |   |   |   |   |
| 19 |   |   |   |   |   |   |   |   |   |
| 20 |   |   |   |   |   |   |   |   |   |
| 21 |   |   |   |   |   |   |   |   |   |
| 22 | X | X | X | X | X | X | X | X | X |
| 23 | X |   |   |   |   |   |   |   |   |
| 24 |   |   |   |   |   |   |   |   |   |
| 25 |   |   |   |   |   |   |   |   |   |
| 26 |   |   |   |   |   |   |   |   |   |
| 27 | X | X | X | X | X | X | X | X | X |
| 28 |   |   |   |   |   |   |   |   |   |

TABLE VII

Univariate/Multivariate Analysis for Prostate Cancer Progression
{N = 124 Radical Prostatectomy Specimens}
Progressors/Non-Progressors: 50/74
Statistical Analysis of JHH-1 Database using Univariately Significant STDEV & VAR Statistics for JVB Texture Features, Biomarkers,
Post Gleason, & JHH-NRV in Progression Prediction

|  | A Post GL | B JHH-NRV | C Bio-markers (n = 3)** | D2 JVB Nuclear Descriptors (n = 19)* | H JVB Nuclear Descriptors (n = 16*) Post GL | I JVB Nuclear Descriptors (n = 17)* JHH-NRV | J JVB Nuclear Descriptors (n = 15)* JHH-NRV Post GL | K JVB Nuclear Descriptors (n = 17)* Biomarkers (n = 2)**** | L JVB Nuclear Descriptors (n = 17)* Biomarkers (n = 3)** Post GL | M JVB Nuclear Descriptors (n = 17)* Biomarkers (n = 3)** JHH-NRV | N JVB Nuclear Descriptors (n = 14)* Biomarkers (n = 2)*** JHH-NRV Post GL |
|---|---|---|---|---|---|---|---|---|---|---|---|
| Positive Cutoff (p>=#) | 0.50 | 0.35 | 0.40 | 0.40 | 0.50 | 0.40 | 0.50 | 0.45 | 0.50 | 0.50 | 0.50 |
| SENSITIVITY | 78.00% | 86.00% | 62.00% | 86.00% | 86.00% | 96.00% | 98.00% | 88.00% | 88.00% | 92.00% | 98.00% |

TABLE VII-continued

Univariate/Multivariate Analysis for Prostate Cancer Progression
{N = 124 Radical Prostatectomy Specimens}
Progressors/Non-Progressors: 50/74
Statistical Analysis of JHH-1 Database using Univariately Significant STDEV & VAR Statistics for JVB Texture Features, Biomarkers,
Post Gleason, & JHH-NRV in Progression Prediction

|  | A Post GL | B JHH-NRV | C Bio-markers (n = 3)** | D2 JVB Nuclear Des-criptors (n = 19)* | H JVB Nuclear Des-criptors (n = 16*) Post GL | I JVB Nuclear Des-criptors (n = 17)* JHH-NRV | J JVB Nuclear Des-criptors (n = 15)* JHH-NRV Post GL | K JVB Nuclear Des-criptors (n = 17)* Bio-markers (n = 2)**** | L JVB Nuclear Des-criptors (n = 17)* Bio-markers (n = 3)** Post GL | M JVB Nuclear Des-criptors (n = 17)* Bio-markers (n = 3)** JHH-NRV | N JVB Nuclear Des-criptors (n = 14)* Bio-markers (n = 2)*** JHH-NRV Post GL |
|---|---|---|---|---|---|---|---|---|---|---|---|
| Pos Predictive Value | 73.58% | 78.18% | 54.39% | 76.79% | 86.00% | 94.12% | 98.00% | 81.48% | 88.00% | 95.83% | 98.00% |
| SPECIFICITY | 81.08% | 83.56% | 64.86% | 82.43% | 90.54% | 95.89% | 98.63% | 86.49% | 91.89% | 97.26% | 98.63% |
| Neg Predictive Value | 84.51% | 89.71% | 71.64% | 89.71% | 90.54% | 97.22% | 98.63% | 91.43% | 91.89% | 94.67% | 98.63% |
| % False Positives | 26.42% | 21.82% | 45.61% | 23.21% | 14.00% | 5.88% | 2.00% | 18.52% | 12.00% | 4.17% | 2.00% |
| % False Negatives | 15.49% | 10.29% | 28.36% | 10.29% | 9.46% | 2.78% | 1.37% | 8.57% | 8.11% | 5.33% | 1.37% |
| Area Under ROC Curve | 0.8262 | 0.8975 | 0.7108 | 0.9300 | 0.9462 | 0.9866 | 0.9934 | 0.9503 | 0.9589 | 0.9885 | 0.9948 |
| Significance | <0.00001 | <0.00001 | 0.0009 | <0.00001 | <0.00001 | <0.00001 | <0.00001 | <0.00001 | <0.00001 | <0.00001 | <0.00001 |

*NOTE: n = number of JVB Nuclear Descriptors which survived the model, either Std. Deviation or Variance or both statistics.
**NOTE: Surviving Biomarkers are C-DNA1, H2NFDN, and PD41-5
***NOTE: Surviving Biomarkers are C-DNA1 and H2NFDN
****NOTE: Surviving Biomarkers are H2NFDN and PD41-5

TABLE VIIa

| Feature | D1 | D2 | H | I | J | K | L | M | N |
|---|---|---|---|---|---|---|---|---|---|
| 1 | X | X |  | X | X | X | X | X | X |
| 2 | X | X | X | X | X | X | X | X | X |
| 3 | X | X | X | X | X | X | X | X | X |
| 4 | X | X | X | X | X | X | X | X |  |
| 5 |  |  |  |  |  |  |  |  |  |
| 6 |  |  |  |  |  |  |  |  |  |
| 7 | X | X | X | X |  | X | X |  | X |
| 8 | X | X |  | X | X |  |  | X | X |
| 9 |  |  |  |  |  |  |  |  |  |
| 10 | X | X | X | X | X | X | X | X | X |
| 11 | X | X | X | X | X | X | X | X | X |
| 12 |  |  |  |  |  |  |  |  |  |
| 13 |  |  |  |  |  |  |  |  |  |
| 14 | X | X | X |  | X | X | X | X |  |
| 15 | X | X | X | X |  | X | X | X | X |
| 16 |  |  |  |  |  |  |  |  |  |
| 17 | X | X |  | X | X | X | X | X |  |
| 18 |  |  |  |  |  |  |  |  |  |
| 19 |  |  |  |  |  |  |  |  |  |
| 20 |  |  |  |  |  |  |  |  |  |
| 21 |  |  |  |  |  |  |  |  |  |
| 22 | X | X |  | X | X |  |  | X | X |
| 23 | X |  |  |  |  |  |  |  |  |
| 24 | X | X | X | X | X | X | X | X | X |
| 25 |  |  |  |  |  |  |  |  |  |
| 26 | X | X | X |  |  | X | X | X |  |
| 27 |  |  |  |  |  |  |  |  |  |
| 28 | X | X | X | X |  | X | X | X |  |
| 29 | X | X | X |  |  | X | X |  | X |
| 30 | X |  | X | X | X | X |  | X | X |
| 31 | X | X | X | X |  |  | X | X |  |
| 32 |  |  |  |  |  |  |  |  |  |
| 33 |  |  |  |  |  |  |  |  |  |
| 34 | X | X | X | X | X | X | X | X | X |
| 35 | X | X | X | X | X | X | X |  | X |
| 36 |  |  |  |  |  |  |  |  |  |

In another embodiment, the ability of Her-2/neu antigenic expression to identify high risk sub-populations of well to moderately differentiated Gleason grades (2–6) as well as high Gleason grades ($\geq 7$) is clearly demonstrated in FIG. 19. Additionally, it was demonstrated that non-diploid DNA ploidy status selected out a subset of well to moderately differentiated Gleason grades (2–6) that were at risk for progression (FIG. 20).

LOGISTIC REGRESSION ORGAN CONFINEMENT MODEL

This invention also applies logistic regression to select the univariately significant variables for organ confinement (Table VIII) using the STATA™ statistical software package (STATA™ command: loogistic). Next, these univariately significant variables are multivariately assessed using backwards stepwise logistic regression (STATA™ command: swlogis) to determine which independent variables (e.g. NMD's (CMP or JVB), Gleason Score, Nuclear Roundness Variance, and biomarkers) are retained to predict organ confinement (Tables IX, Ixa, X, and Xa).

TABLE VIII

Univariate Analysis for Organ Confined Disease Status Prediction using STATA ™ Logistic Regression

| Independent Variable | Statistical Significance (p Value) |
|---|---|
| Post Operative Gleason Score | $p \leq 0.00001$ |
| Nuclear Roundness Variance* | $p = 0.0073$ |
| Best CAS-200 CMP v3.0 Nuclear Morphometric Descriptors | $p = 0.0005$ |
| Best CAS-200 JVB v1.0 Nuclear Morphometric | $p = 0.0003$ |

TABLE VIII-continued

Univariate Analysis for Organ Confined Disease Status Prediction using STATA ™ Logistic Regression

| Independent Variable | Statistical Significance (p Value) |
|---|---|
| Descriptors | |
| CAS-200 DNA Ploidy - 1 (C-DNA1) | p = 0.0703** |
| CAS-200 DNA Ploidy - 10 (C-DNA10) | p = 0.0546** |
| CAS-200 DNA Ploidy - JIE (JHHDNA10) | p = 0.0499 |
| Her-2/neu Antigenicity: Focal, Diffuse, Negative (H2NFDN) | p = 0.0023 |
| PCNA Antigenicity | p = 0.1330** |
| PD-41 Antigenicity | p = 0.0198 |

*Measured using DynaCell ™ system at Johns Hopkins Hospital
**Not Statistically Significant. Must be less than 0.0500 to be statistically significant.

TABLE IX

Univariate/Multivariate Analysis for Prostate Cancer Organ Confinement
{N = 124 Radical Prostatectomy Specimens}
Organ Confined/Non-Organ Confined: 29/95
Statistical Analysis of JHH-1 Database using Univariately Significant STDEV & VAR Statistics for CMP Texture Features, Biomarkers, Post Gleason, & JHH-NRV in Organ Confinement Prediction

| | A Post GL | B JHH-NRV | C Biomarkers (n = 3)** | D2 CMP Nuclear Descriptors (n = 10)* | H CMP Nuclear Descriptors (n = 11*) Post GL | I CMP Nuclear Descriptors (n = 13)* JHH-NRV | J CMP Nuclear Descriptors (n = 14)* Post GL | K CMP Nuclear Descriptors (n = 12)* Biomarkers (n = 2)*** | L CMP Nuclear Descriptors (n = 14)* Biomarkers (PD41:5) Post GL | M CMP Nuclear Descriptors (n = 12)* Biomarkers (n = 3)** JHH-NRV | N CMP Nuclear Descriptors (n = 14)* Biomarkers (n = 2)**** JHH-NRV Post GL |
|---|---|---|---|---|---|---|---|---|---|---|---|
| Positive Cutoff (p>=#) | 0.20 | 0.30 | 0.25 | 0.30 | 0.25 | 0.25 | 0.50 | 0.40 | 0.50 | 0.35 | 0.50 |
| SENSITIVITY | 86.21% | 58.62% | 55.17% | 72.41% | 82.76% | 82.76% | 68.97% | 68.97% | 75.86% | 75.86% | 72.41% |
| Pos Predictive Value | 35.21% | 39.53% | 34.04% | 52.50% | 54.55% | 57.14% | 83.33% | 66.67% | 78.57% | 62.86% | 75.00% |
| SPECIFICITY | 51.58% | 72.34% | 67.37% | 80.00% | 78.95% | 80.85% | 95.74% | 89.47% | 93.65% | 86.17% | 92.55% |
| Neg Predictive Value | 92.45% | 85.00% | 83.12% | 90.48% | 93.75% | 93.83% | 90.91% | 90.43% | 92.71% | 92.05% | 91.58% |
| % False Positives | 64.79% | 60.47% | 65.96% | 47.50% | 45.45% | 42.86% | 16.67% | 33.33% | 21.43% | 37.14% | 25.00% |
| % False Negatives | 7.55% | 15.00% | 16.88% | 9.52% | 6.25% | 6.17% | 9.09% | 9.57% | 7.29% | 7.95% | 8.42% |
| Area Under ROC Curve | 0.733 | 0.6618 | 0.6973 | 0.8635 | 0.9180 | 0.8833 | 0.9219 | 0.8831 | 0.9397 | 0.9028 | 0.9413 |
| Significance | <0.00001 | 0.0073 | 0.0026 | 0.0005 | <0.00001 | 0.0017 | <0.00001 | 0.0015 | <0.00001 | 0.006 | <0.00001 |

*NOTE: n = number of CMP Nuclear Descriptors which survived the model, either Std. Deviation or Variance or both statistics.
**NOTE: Surviving Biomarkers are C-DNA1, H2NFDN, and PD41-5
***NOTE: Surviving Biomarkers are H2NFDN and PD41-5
****NOTE: Surviving Biomarkers are C-DNA1 and PD41-5

TABLE IXa

| Feature | D1 | D2 | H | I | J | K | L | M | N |
|---|---|---|---|---|---|---|---|---|---|
| 1 | X | X | X | X | X | X | X | X | X |
| 2 | | | | | | | | | |
| 3 | | | | | | | | | |
| 4 | X | X | X | X | X | X | X | X | X |
| 5 | | | | | | | | | |
| 6 | X | X | X | X | X | X | X | X | X |
| 7 | | | | | | | | | |
| 8 | X | X | X | | X | | X | | X |
| 9 | | | | | | | | | |
| 10 | X | X | X | X | X | X | X | X | X |
| 11 | X | X | X | X | X | X | X | X | X |
| 12 | | | | | | | | | |
| 13 | X | | | X | X | X | X | X | X |
| 14 | X | | X | X | X | X | X | | X |
| 15 | X | X | X | X | X | X | X | X | X |
| 16 | X | X | X | X | X | X | X | X | X |
| 17 | X | | | X | X | X | X | X | X |
| 18 | | | | | | | | | |
| 19 | | | | | | | | | |
| 20 | | | | | | | | | |
| 21 | | | | | | | | | |
| 22 | X | | | X | X | X | X | X | X |
| 23 | X | | | | | | | | |
| 24 | X | X | X | X | X | X | X | X | X |
| 25 | | | | | | | | | |
| 26 | X | X | X | X | X | | X | X | X |
| 27 | X | | | | | | | | |
| 28 | | | | | | | | | |

TABLE X

Univariate/Multivariate Analysis for Prostate Cancer Organ Confinment
{N = 124 Radical Prostatectomy Specimens}
Organ Confined/Non-Organ Confined: 29/95
Statistical Analysis of JHH-1 Database using Univariately Significant STDEV & VAR Statistics for JVB Texture Features, Biomarkers,
Post Gleason, & JHH-NRV in Organ Confinment Prediction

| | A Post GL | B JHH-NRV | C Biomarkers (n = 3)** | D2 JVB Nuclear Descriptors (n = 15)* | H JVB Nuclear Descriptors (n = 15*) Post GL | I JVB Nuclear Descriptors (n = 16)* JHH-NRV | J JVB Nuclear Descriptors (n = 15)* (dropped) Post GL | K JVB Nuclear Descriptors (n = 16)* Biomarkers (n = 2)*** | L JVB Nuclear Descriptors (n = 15)* Biomarkers (n = 2)*** Post GL | M JVB Nuclear Descriptors (n = 16)* Biomarkers (n = 2)*** JHH-NRV | N JVB Nuclear Descriptors (n = 16)* Biomarkers (n = 3)** (dropped) Post GL |
|---|---|---|---|---|---|---|---|---|---|---|---|
| Positive Cutoff (p>=#) | 0.20 | 0.30 | 0.25 | 0.35 | 0.40 | 0.40 | 0.40 | 0.40 | 0.40 | 0.40 | 0.40 |
| SENSITIVITY | 86.21% | 58.62% | 55.17% | 86.21% | 79.31% | 79.31% | 79.31% | 82.76% | 93.10% | 82.76% | 93.10% |
| Pos predictive Value | 35.21% | 39.53% | 34.04% | 64.10% | 71.88% | 65.71% | 71.88 | 75.00% | 81.82% | 72.73% | 81.82% |
| SPECIFICITY | 51.58% | 72.34% | 67.37% | 85.26% | 90.53% | 87.23% | 90.53 | 91.58% | 93.68% | 90.43% | 93.68% |
| Neg Predictive Value | 92.45% | 85.00% | 83.12% | 95.29% | 93.48% | 93.18% | 93.48% | 94.57% | 97.80% | 94.44% | 97.80% |
| % False Positives | 64.79% | 60.47% | 65.96% | 35.90% | 28.13% | 34.29% | 28.13% | 25.00% | 18.18% | 27.27% | 18.18% |
| % False Negatives | 7.55% | 15.00% | 16.88% | 4.71% | 6.52% | 6.82% | 6.52% | 5.43% | 2.20% | 5.56% | 2.20% |
| Area Under ROC Curve | 0.7330 | 0.6618 | 0.6973 | 0.9143 | 0.9170 | 0.9156 | 0.9470 | 0.9336 | 0.9670 | 0.9384 | 0.9655 |
| Significance | <0.00001 | 0.0073 | 0.0026 | 0.0003 | <0.00001 | 0.0003 | <0.00001 | <0.00001 | <0.00001 | <0.00001 | <0.00001 |

*NOTE: n = number of JVB Nuclear Descriptors which survived the model, either Std. Deviation or Variance or both statistics.
**NOTE: Surviving Biomarkers are C-DNA1, H2NFDN, and PD41-5
***NOTE: Surviving Biomarkers are H2NFDN and PD41-5

TABLE Xa

| Feature | D1 | D2 | H | I | J | K | L | M | N |
|---|---|---|---|---|---|---|---|---|---|
| 1 | X | X | X | X | X | X | X | X | X |
| 2 | | | | | | | | | |
| 3 | | | | | | | | | |
| 4 | X | X | X | X | X | X | X | X | X |
| 5 | | | | | | | | | |
| 6 | X | X | X | X | X | X | X | X | X |
| 7 | | | | | | | | | |
| 8 | X | X | X | X | X | X | X | X | X |
| 9 | | | | | | | | | |
| 10 | X | X | X | X | X | X | X | X | X |
| 11 | X | X | X | X | X | X | X | X | X |
| 12 | | | | | | | | | |
| 13 | X | X | X | X | X | X | | X | X |
| 14 | X | X | X | X | X | X | X | X | X |
| 15 | X | X | X | X | X | X | X | X | X |
| 16 | X | X | X | X | X | X | X | X | X |
| 17 | X | X | X | X | X | X | X | X | X |
| 18 | | | | | | | | | |
| 19 | | | | | | | | | |
| 20 | | | | | | | | | |
| 21 | | | | | | | | | |
| 22 | X | X | X | X | X | X | X | X | X |
| 23 | X | | | | | | | | |
| 24 | X | X | X | X | X | X | X | X | X |
| 25 | | | | | | | | | |
| 26 | X | | | X | | X | X | X | X |
| 27 | | | | | | | | | |
| 28 | | | | | | | | | |
| 29 | X | | | | | | | | |
| 30 | X | X | X | X | X | X | X | X | X |
| 31 | X | X | X | X | X | X | X | X | X |
| 32 | | | | | | | | | |
| 33 | | | | | | | | | |
| 34 | | | | | | | | | |
| 35 | | | | | | | | | |
| 36 | | | | | | | | | |

TABLE Xb

JHH1 METASTATIC SUBSET
n = 13

| PCode | OC | PROG | PostGL | Ex-posure | Local | Distant | PD41 | DNA Ploidy | Her-2/neu | JVB NMD Predicted Progression Probatility | JVB NMD Predicted Progression Outcome (Cutoff = 0.40) | Total Model (Model L) Predicted Probabilities | Total Model (JVB Progression Model L) Predicted Outcome (Cutoff = 0.50) |
|---|---|---|---|---|---|---|---|---|---|---|---|---|---|
| 45  | 0 | 1 | 9 | 7 | 0 | 1 | + | Aneuploid | + | 0.9988 | 1 | 0.9645 | 1 |
| 100 | 0 | 1 | 6 | 7 | 1 | 1 | + | Aneuploid | + | 0.3499 | 0 | 0.1498 | 0 |
| 101 | 0 | 1 | 6 | 1 | 1 | 0 | + | Aneuploid | + | 0.0917 | 0 | 0.4268 | 0 |
| 105 | 0 | 1 | 8 | 8 | 1 | 0 | + | Aneuploid | + | 0.7284 | 1 | 0.9763 | 1 |
| 149 | 1 | 1 | 6 | 1 | 1 | 0 | − | Aneuploid | + | 0.9767 | 1 | 0.5812 | 1 |
| 200 | 0 | 1 | 7 | 5 | 1 | 0 | + | Aneuploid | − | 0.7355 | 1 | 0.8157 | 1 |
| 210 | 0 | 1 | 8 | 6 | 1 | 0 | + | Diploid   | + | 0.9997 | 1 | 0.9999 | 1 |
| 260 | 0 | 1 | 7 | 1 | 1 | 1 | − | Aneuploid | + | 0.8009 | 1 | 0.8254 | 1 |
| 359 | 0 | 1 | 7 | 2 | 1 | 0 | − | Diploid   | + | 1.0000 | 1 | 0.9906 | 1 |
| 410 | 0 | 1 | 7 | 4 | 0 | 1 | + | Diploid   | + | 0.6481 | 1 | 0.6127 | 1 |
| 498 | 0 | 1 | 7 | 3 | 1 | 0 | + | Diploid   | + | 0.7657 | 1 | 0.9685 | 1 |
| 699 | 0 | 1 | 8 | 3 | 1 | 0 | + | Aneuploid | + | 0.8843 | 1 | 0.9999 | 1 |
| 753 | 0 | 1 | 7 | 2 | 0 | 1 | − | Aneuploid | + | 1.0000 | 1 | 1.0000 | 1 |

OC: 1 = Organ Confined Disease, 0 = Non-Organ Confined Disease
PROG: 1 = Disease Progression, 0 = Non-Progression of Disease
PostGL: Combined Post-Operative Gleason Score
Exposure: The time in years that it took for disease progression.
Local: 1 = Metastasis to surrounding tissue (i.e. lymph nodes and seminal vesicles), 0 = No local metastasis.
Distant: 1 = Metastasis to distant site (i.e. bone marrow), 0 = No distant metastasis.
Predicted Outcomes: 1 = Prostate cancer predicted to progress, 0 = Prostate cancer predicted not to progress.

In another embodiment, the ability of PD-41 antigenic expression to identify non-organ confined disease status was evaluated. Positive PD-41 antigenic expression was found in 67 of 95 (71%) patients with non-organ confined disease. Additionally, Her-2/neu antigenic expression was also shown to strongly correlate to non-organ confined disease status. Positive Her-2/neu antigenic expression was found in 80 of 95 (84%) patients with non-organ confined disease.

Finally, a select subgroup of patients that developed fatal metastatic disease (n=13) were a evaluated for DNA ploidy, PD-41 and Her-2/neu antigenic expression (Table Xb). DNA aneuploidy was observed in 9 of 13 (69%) and positive PD-41 antigenic expression was found in 9 of 13 (69%) patients that recurred with fatal metastatic disease. Additionally, Her-2/neu antigenic expression was shown to strongly correlate to fatal metastatic disease. Positive Her-2/neu antigenic expression was found in 12 of 13 (92%) patients that recurred with fatal metastatic disease. These data clearly support the potential value of these biomarkers for early identification of patients at high risk for fatal metastatic disease.

METHODS TO OBTAIN PATIENT-SPECIFIC RESULTS

Logistic Regression Method—STATA™ provides a command (logit, an estimated maximum-likelihood logit model) that provides the weighted coefficients for the statistically significant independent variables used in the multivariate model and the model constant. The general formulas for calculating the predictive index and predictive probability are as follows:

Predictive Index $(xb)=(\beta_0+\beta_1 \text{var}(1)+\beta_2 \text{var}(2)+ - - - +\beta_n \text{var}(n))$ Predictive Probability $(p)=e^{xb}/(1+e^{xb})$ Where:

$\beta_0$=Formula Constant $\beta_1$ through $\beta_n$=Weight factors for variables 1 through n var(1) through var(n)=Independent variables being used in logistic regression model.

The final calculation of the predictive probability provides a patient-specific value, between 0 and 1, for the probability of a specific outcome (e.g. progression or organ confined disease status). The threshold value (cutoff) for the predicted probability is selected based upon the results of the ROC curves. Table XI illustrates patient specific NMD and multi-parameter (combined) predictive probabilities calculated using this method.

TABLE XI

Use of Logistic Regression (logit) to Predict Patient-Specific Outcomes

| Case I.D. | PD41-5 | C-DNA1 | H2NFDN | PostGL | Morphometry Predictive Probability | Combined Parameters Predictive Probabilities | Predicted Outcome (Cutoff: 0.50) |
|---|---|---|---|---|---|---|---|
| 33 | + | Diploid | Focal | 5 | 0.14 | 0.02 | 0 |
| 34 | − | Ab: >S + G2M | Diffuse | 7 | 0.92 | 0.93 | 1 |
| 149 | − | Aneuploid | Focal | 6 | 0.98 | 0.58 | 1 |
| 9952 | − | Hypodiploid | Diffuse | 4 | 0.09 | 0.00 | 0 |

Neural Networks—The first network configuration to be considered was a standard multilayer sigmoidal network with a single hidden layer. The neural network input layer consisted of either 15, 28, or 30 input nodes to accommodate the input data set of either 15, 28, or 30 measurements (NMD's and Gleason Score). The activation function in each hidden layer and output layer neuron is sigmoid. Different network configurations (number of hidden layer neurons) with various training termination conditions were tested. FIG. 29 illustrates the neural network configuration used in this study. It was found, for the given training set, that the neural network classifier works best with 20 hidden layer neurons and when the training is terminated at approximately 1000 iterations.

The second network configuration tested consisted of a single hidden layer as well. However, the non-linearity function used was the sinusoidal function (proprietary Hybrid network). The output layer neurons still used the sigmoidal transfer function. It had the same structure as the first network (see FIG. 29). A number of different frequencies were tested to find the best combination. The best frequency was found to be F=0.2.

All networks (standard and hybrid with 15, 28, or 30 inputs) were tested using the ten different combinations of randomly selected test (18) and training (106) cases. The threshold value (cutoff) used in all cases was 0.5. Table XII summarizes the results using the standard sigmoidal neural networks applied to the n=124 patient sample described in this invention (Tables XIIa, b, & c). Notable is the fact that this network degrades as the number of input features is increased from 15 to 28 to 30. Please note that the 28 and 30 feature networks did not undergo pre-selection using logistic regression methods. The best performing network was the one labeled "15 Input Features", where the features were pre-selected based upon statistical significance using logistic regression methods. Therefore, the use of statistical methods to pre-select statically significant features improves network performance. Also it is evident from the variation in the predictive rates among the ten trained networks that if the number of patients is increased, the performance of the network should be significantly improved.

TABLE XII

Sigmoidal Neural Network Comparisons: JHH-1 (n = 124)

| | Progression Predictive Rates | | |
|---|---|---|---|
| Network # | 15 Feature NN | 28 Feature NN | 30 Feature NN |
| 1 | 78% | 61% | 67% |
| 2 | 83% | 61% | 61% |
| 3 | 89% | 50% | 50% |
| 4 | 67% | 83% | 67% |
| 5 | 67% | 72% | 72% |
| 6 | 83% | 78% | 67% |
| 7 | 89% | 78% | 72% |
| 8 | 78% | 78% | 72% |
| 9 | 72% | 78% | 78% |
| 10 | 89% | 72% | 72% |
| Mean | 79% | 71% | 68% |
| Standard Error | 3% | 3% | 2% |
| Median | 81% | 75% | 70% |
| Mode | 78% | 78% | 72% |
| Standard Deviation | 9% | 10% | 8% |
| Variance | 1% | 1% | 1% |

TABLE XIIa

Sigmoidal Neural Network: 15 Input Features

| Network # | Predictive Rate | Total Error | % Error Progressors | % Error Non-Progressors |
|---|---|---|---|---|
| 1 | 78% | 22% | 33% | 11% |
| 2 | 83% | 17% | 33% | 0% |
| 3 | 89% | 11% | 22% | 0% |
| 4 | 67% | 33% | 55% | 11% |
| 5 | 67% | 33% | 55% | 11% |
| 6 | 83% | 17% | 22% | 11% |
| 7 | 89% | 11% | 22% | 0% |
| 8 | 78% | 22% | 33% | 11% |
| 9 | 72% | 28% | 33% | 22% |
| 10 | 89% | 11% | 11% | 11% |
| Mean | 80% | 21% | 32% | 9% |
| Standard Error | 3% | 3% | 4% | 2% |
| Median | 81% | 20% | 33% | 11% |
| Mode | 89% | 11% | 33% | 11% |
| Standard Deviation | 9% | 9% | 14% | 7% |
| Variance | 1% | 1% | 2% | 0% |

TABLE XIIb

Sigmoidal Neural Network: 28 Input Features

| Network # | Predictive Rate | Total Error | % Error Progressors | % Error Non-Progressors |
|---|---|---|---|---|
| 1 | 61% | 39% | 55% | 22% |
| 2 | 61% | 39% | 55% | 22% |
| 3 | 50% | 50% | 67% | 33% |
| 4 | 83% | 17% | 33% | 0% |
| 5 | 72% | 28% | 44% | 11% |
| 6 | 78% | 22% | 33% | 11% |
| 7 | 78% | 22% | 33% | 11% |

TABLE XIIb-continued

Sigmoidal Neural Network: 28 Input Features

| Network # | Predictive Rate | Total Error | % Error Progressors | % Error Non-Progressors |
|---|---|---|---|---|
| 8 | 78% | 22% | 33% | 11% |
| 9 | 78% | 22% | 44% | 0% |
| 10 | 72% | 28% | 44% | 11% |
| Mean | 71% | 29% | 44% | 13% |
| Standard Error | 3% | 3% | 4% | 3% |
| Median | 75% | 25% | 44% | 11% |
| Mode | 78% | 22% | 33% | 11% |
| Standard Deviation | 10% | 10% | 12% | 10% |
| Variance | 1% | 1% | 1% | 1% |

TABLE XIIc

Sigmoidal Neural Network: 30 Input Features

| Network # | Predictive Rate | Total Error | % Error Progressors | % Error Non-Progressors |
|---|---|---|---|---|
| 1 | 67% | 33% | 44% | 22% |
| 2 | 61% | 39% | 67% | 11% |
| 3 | 50% | 50% | 67% | 33% |
| 4 | 67% | 33% | 67% | 0% |
| 5 | 72% | 28% | 44% | 11% |
| 6 | 67% | 33% | 44% | 22% |
| 7 | 72% | 28% | 44% | 11% |
| 8 | 72% | 28% | 33% | 22% |
| 9 | 78% | 22% | 44% | 0% |
| 10 | 72% | 28% | 44% | 11% |
| Mean | 68% | 32% | 50% | 14% |
| Standard Error | 2% | 2% | 4% | 3% |
| Median | 70% | 31% | 0% | 11% |
| Mode | 72% | 28% | 0% | 11% |
| Standard Deviation | 8% | 8% | 12% | 10% |
| Variance | 1% | 1% | 2% | 1% |

Table XIII illustrates the results for the Hybrid neural network using the n=124 patient sample described in this invention (Tables XIIIa, b, & c). The same observations as made for the standard sigmoidal network above apply to the Hybrid neural network. In conclusion, the use of appropriately trained standard or Hybrid neural networks can be used to predict patient specific outcomes (e.g. progression or organ confined disease status).

Classification and Regression Trees (CART)—Application of recursive partitioning methods using the SYSTAT CART™ for DOS v1.02 (Evanston, Ill.) software program was performed. This method is another example of a non-parametric statistical classifier. The use of this method yields similar classification results using the well defined patient sample (n=124), and can generate a patient specific outcome using a trained CART. Those experienced in the art of non-parametric statistical classifiers realize that several other such methods exist and can be applied to achieve this same end.

TABLE XIII

Hybrid Neural Network Comparisons: JHH-1 (n = 124)

| | Progression Predictive Rates | | |
|---|---|---|---|
| Network # | 15 Feature NN | 28 Feature NN | 30 Feature NN |
| 1 | 67% | 72% | 67% |
| 2 | 67% | 56% | 67% |
| 3 | 83% | 56% | 56% |
| 4 | 67% | 56% | 67% |
| 5 | 72% | 67% | 78% |
| 6 | 89% | 72% | 72% |
| 7 | 89% | 67% | 78% |
| 8 | 78% | 72% | 67% |
| 9 | 72% | 72% | 67% |
| 10 | 78% | 67% | 78% |
| Mean | 76% | 68% | 70% |
| Standard Error | 3% | 1% | 2% |
| Median | 75% | 67% | 67% |
| Mode | 67% | 67% | 67% |
| Standard Deviation | 9% | 4% | 7% |
| Variance | 1% | 0% | 0% |

TABLE XIIIa

Hybrid Neural Network: 15 Input Features

| Network # | Predictive Rate | Total Error | % Error Progressors | % Error Non-Progressors |
|---|---|---|---|---|
| 1 | 67% | 33% | 44% | 22% |
| 2 | 67% | 33% | 55% | 11% |
| 3 | 83% | 17% | 22% | 11% |
| 4 | 67% | 33% | 44% | 22% |
| 5 | 72% | 28% | 44% | 11% |
| 6 | 89% | 11% | 22% | 0% |
| 7 | 90% | 11% | 22% | 0% |
| 8 | 78% | 22% | 33% | 11% |
| 9 | 72% | 28% | 33% | 22% |
| 10 | 78% | 22% | 22% | 22% |
| Mean | 76% | 24% | 34% | 13% |
| Standard Error | 3% | 3% | 4% | 3% |
| Median | 75% | 25% | 33% | 11% |
| Mode | 67% | 33% | 22% | 22% |
| Standard Deviation | 9% | 9% | 12% | 9% |
| Variance | 1% | 1% | 1% | 1% |

TABLE XIIIb

Hybrid Neural Network: 28 Input Features

| Network # | Predictive Rate | Total Error | % Error Progressors | % Error Non-Progressors |
|---|---|---|---|---|
| 1 | 72% | 28% | 33% | 22% |
| 2 | 56% | 44% | 55% | 33% |
| 3 | 56% | 44% | 67% | 22% |
| 4 | 56% | 44% | 67% | 22% |
| 5 | 67% | 33% | 44% | 22% |
| 6 | 72% | 28% | 44% | 11% |
| 7 | 67% | 33% | 55% | 11% |
| 8 | 72% | 28% | 33% | 22% |
| 9 | 72% | 28% | 44% | 11% |
| 10 | 67% | 33% | 55% | 11% |
| Mean | 66% | 34% | 50% | 19% |
| Standard Error | 2% | 2% | 4% | 2% |
| Median | 67% | 33% | 50% | 22% |
| Mode | 67% | 28% | 55% | 11% |
| Standard Deviation | 7% | 7% | 12% | 7% |
| Variance | 1% | 1% | 1% | 1% |

TABLE XIIIc

Hybrid Neural Network: 30 Input Features

| Network # | Predictive Rate | Total Error | % Error Progressors | % Error Non-Progressors |
|---|---|---|---|---|
| 1 | 67% | 33% | 44% | 22% |
| 2 | 67% | 33% | 44% | 22% |
| 3 | 56% | 44% | 78% | 11% |
| 4 | 67% | 33% | 55% | 11% |
| 5 | 78% | 22% | 33% | 11% |
| 6 | 72% | 28% | 33% | 22% |
| 7 | 78% | 22% | 22% | 22% |
| 8 | 67% | 33% | 44% | 22% |
| 9 | 67% | 33% | 55% | 11% |
| 10 | 78% | 22% | 33% | 11% |
| Mean | 70% | 30% | 44% | 17% |
| Standard error | 2% | 2% | 5% | 2% |
| Median | 67% | 33% | 44% | 17% |
| Mode | 67% | 33% | 44% | 22% |
| Standard Deviation | 7% | 7% | 16% | 6% |
| Variance | 0% | 0% | 2% | 0% |

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 28A and FIG. 28B. DNA Classification scheme for prostate image analysis. Normal range: Diploid: S–Hase+ G2M<10% of cells studies; Out of normal range: Hypodiploid: DNA Index<0.70 >S+G2M: 11–21% of cells studies (includes hyperploidy); Abnormal range>S+G2M: >22% of cells studied; aneuploid: >10% of cells studied; tetraploid: >16% of cells studied.

DETAILED DESCRIPTION

Figure 1A:
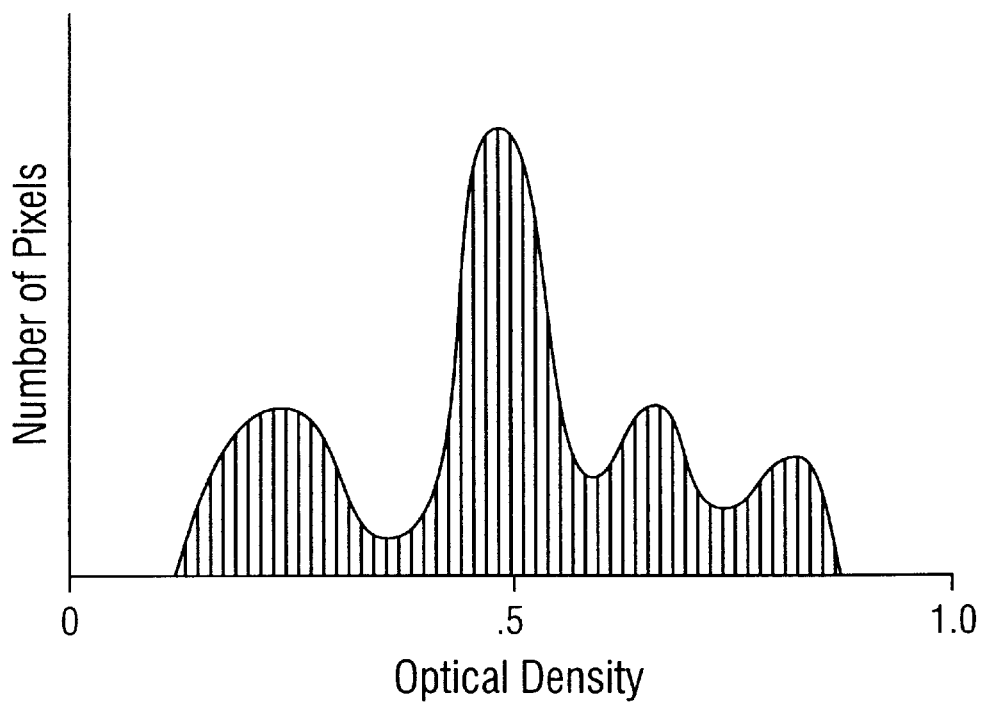
FIG. 1A and FIG. 1B. Normalization plot of each individual pixel optical density (gray level), divided into eight equally frequent gray-level ranges (optical density ranges); each range containing an equal number of pixels.
Figure 1B:
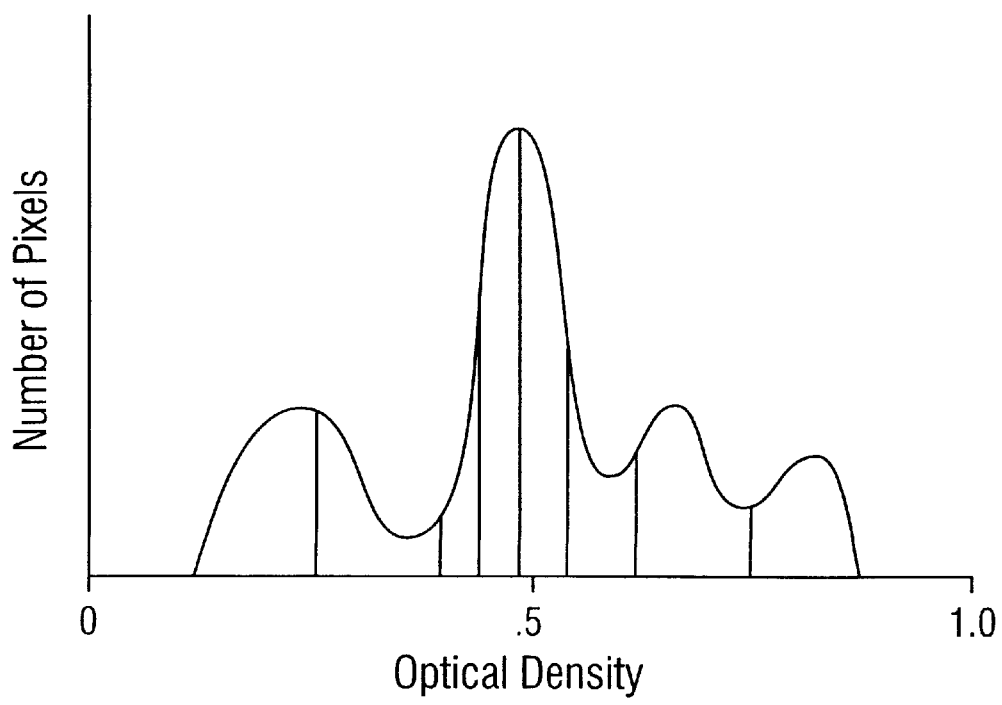
Figure 2:
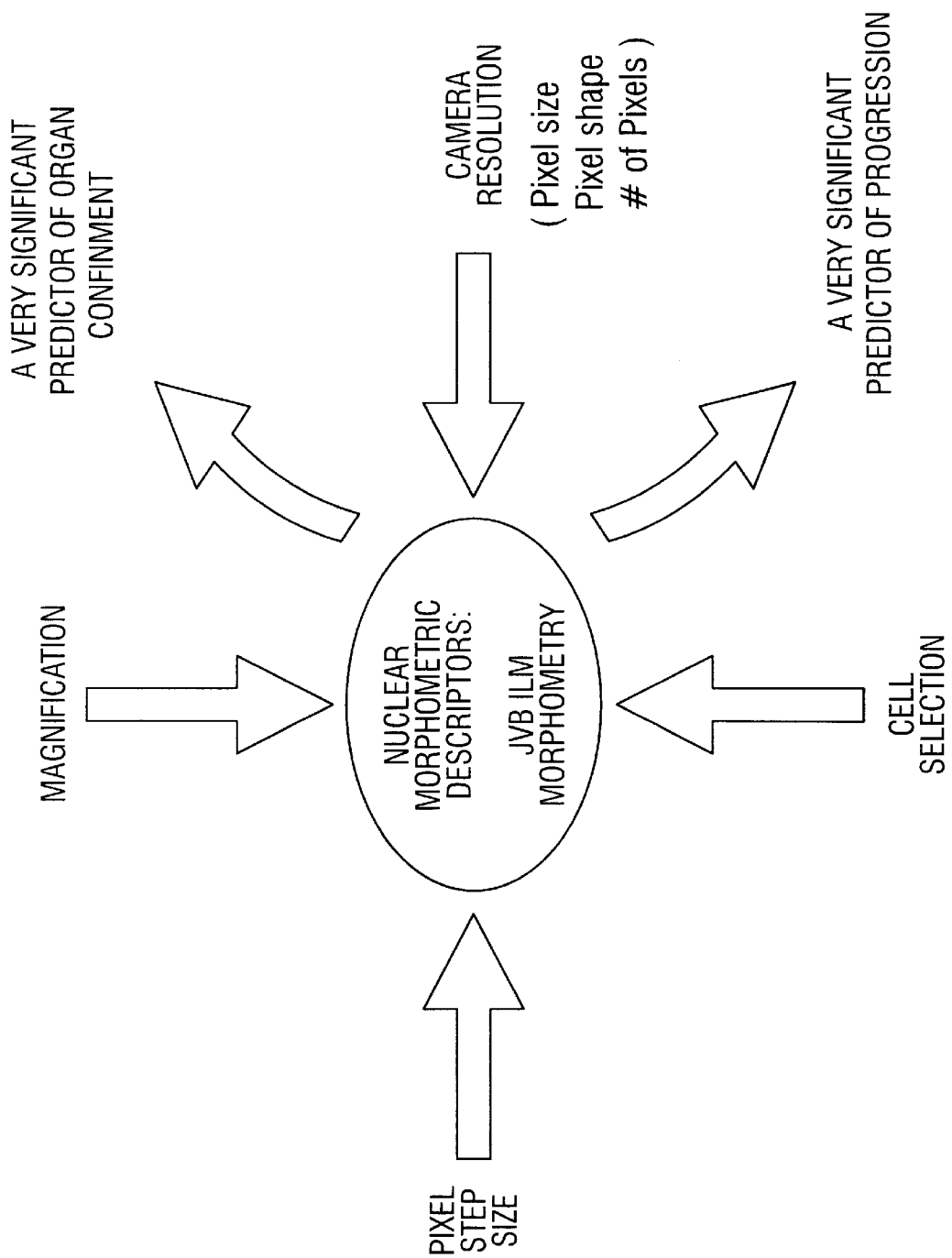
FIG. 2. Parameters including cell selection, magnification, camera resolution (pixel size, pixel shape and number of pixels), and Markovian step size that can significantly alter nuclear morphometric descriptor outputs.
Figure 3:
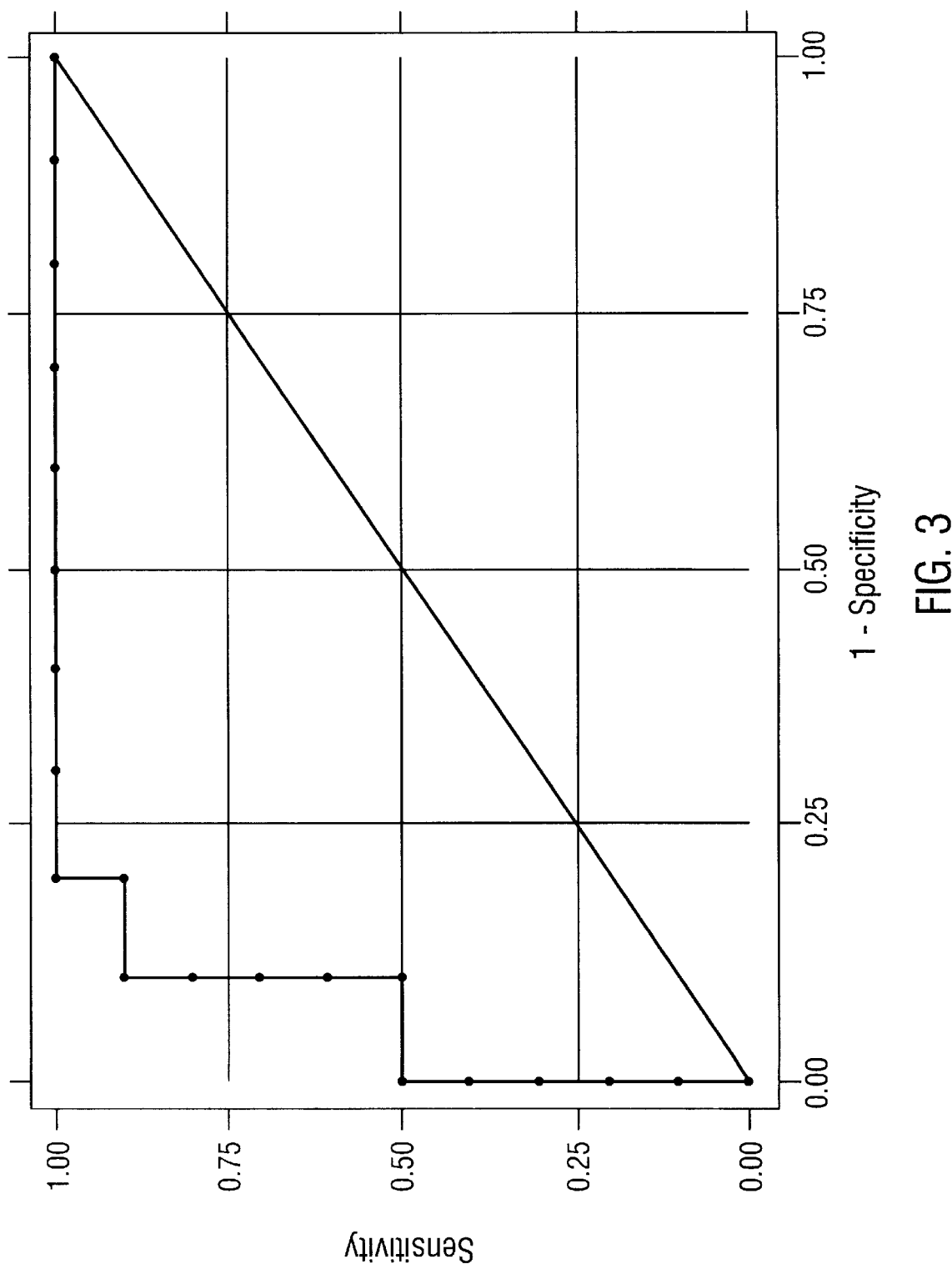
FIG. 3. Identification of progressors (subset of 20 cases) using standard deviation and variance of best CMP 40× nuclear morphometic descriptors. This figure shows the predictive power using the combined CMP NMD's measured with a 40× objective. Using 7 different CMP NMD's, a ROC curve was produced with an area under the curve of 94%.
Figure 4:
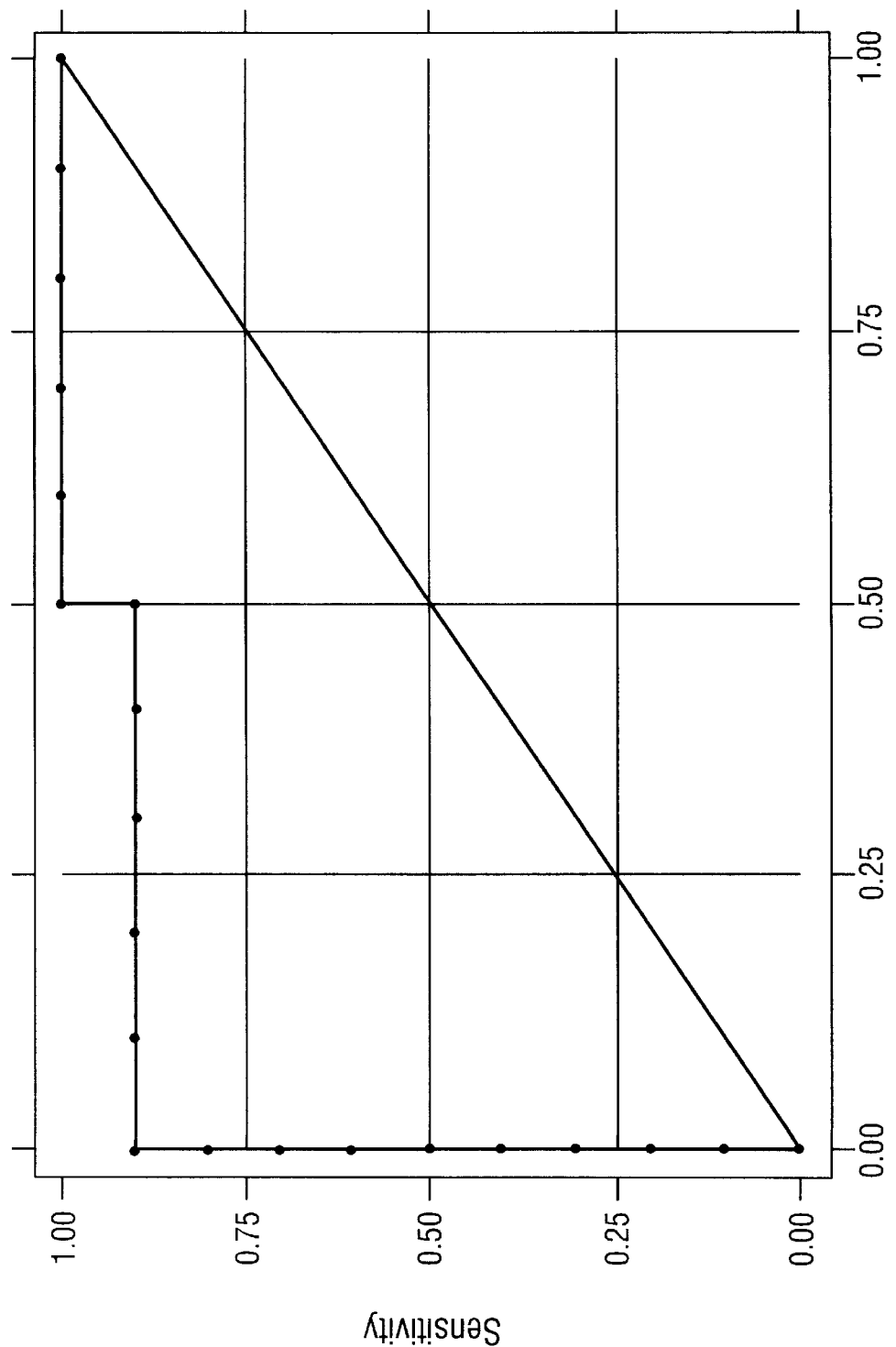
FIG. 4. Identification of progressors (subset of 20 cases) using standard deviation and variance of best JVB 40× nuclear morphometric descriptors. This figure shows the predictive power using the combined JVB NMD's measured with a 40× objective. Using 8 different JNB NMD's, a ROC curve was produced with an area under the curve of 95%.
Figure 5:
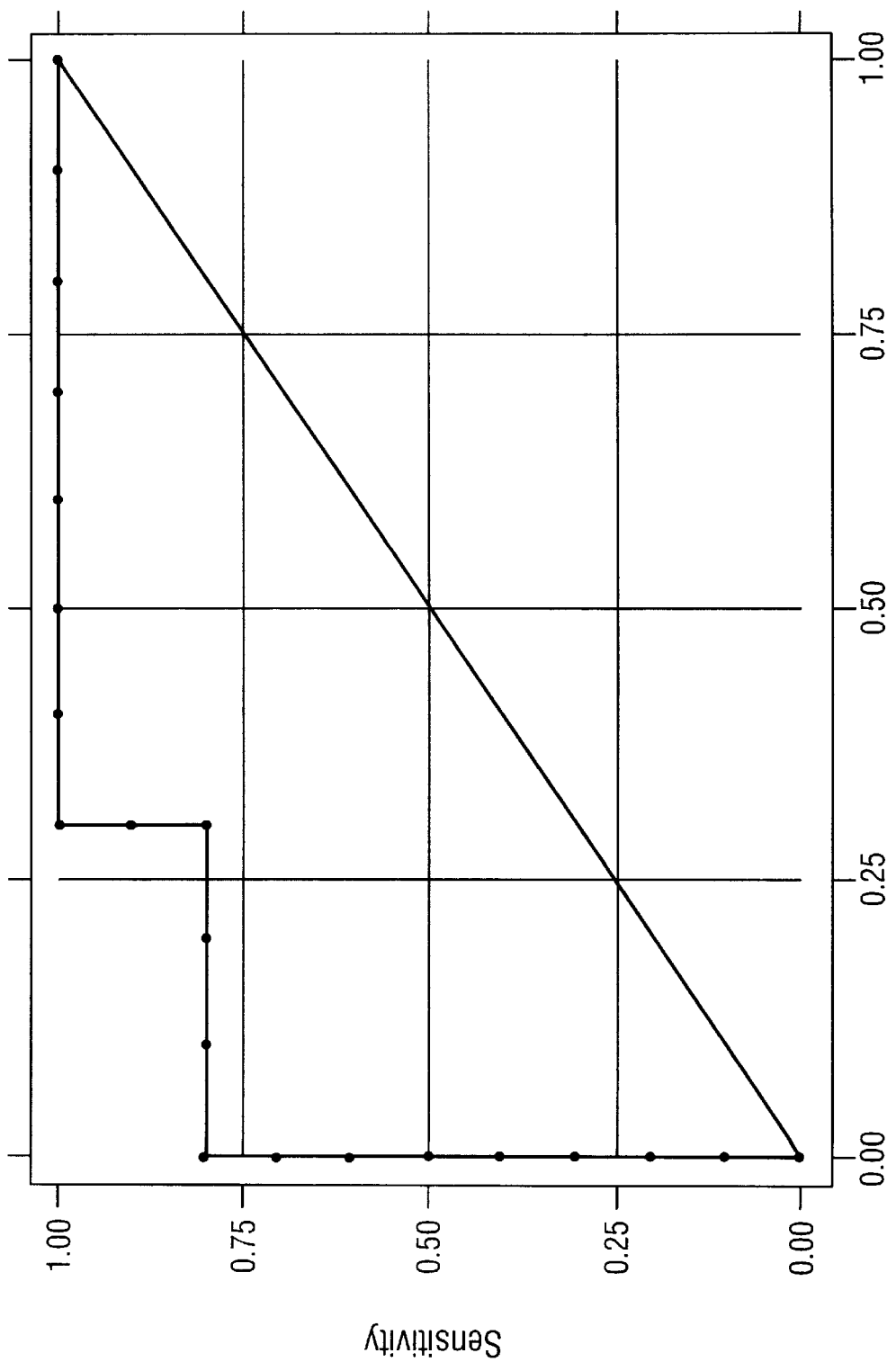
FIG. 5. Identification of progressors (subset of 20 cases) using standard deviation and variance of best CMP 63× nuclear morphometric descriptors. This figure shows the predictive power using the combined CMP NMD's measured with a 63× objective. Using 6 different CMP NMD'S, a ROC curve was produced with an area under the curve of 94%.
Figure 6:
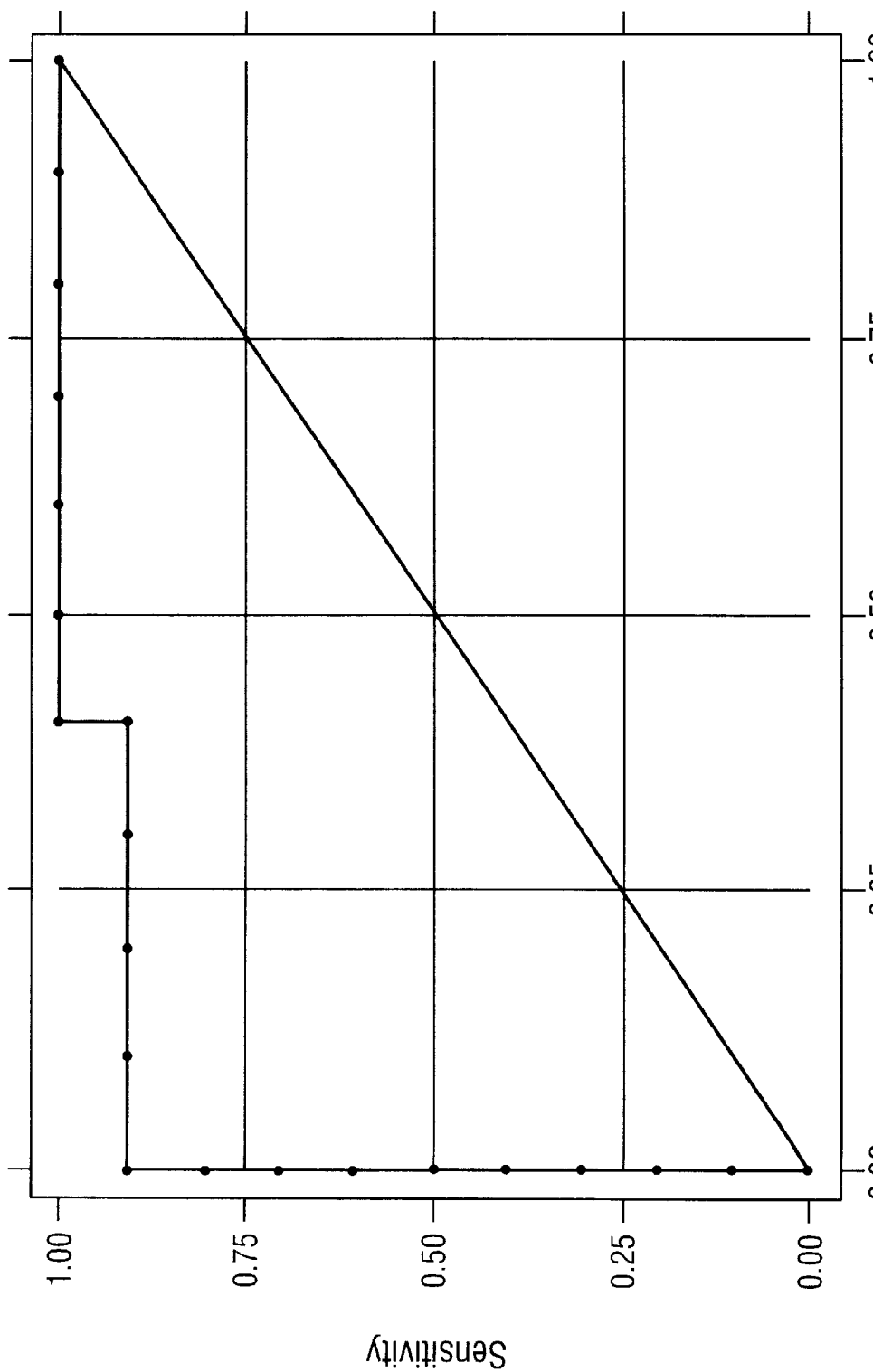
FIG. 6. Identification of progressors (subset of 20 cases) using standard deviation and variance of best JVB 63× nuclear morphometric descriptors. This figure shows the predictive power using the combined JVB NMD's measured with a 63× objective. Using 5 different JVB NMD's, a ROC curve was produced with an area under the curve of 96%.
Figure 7:
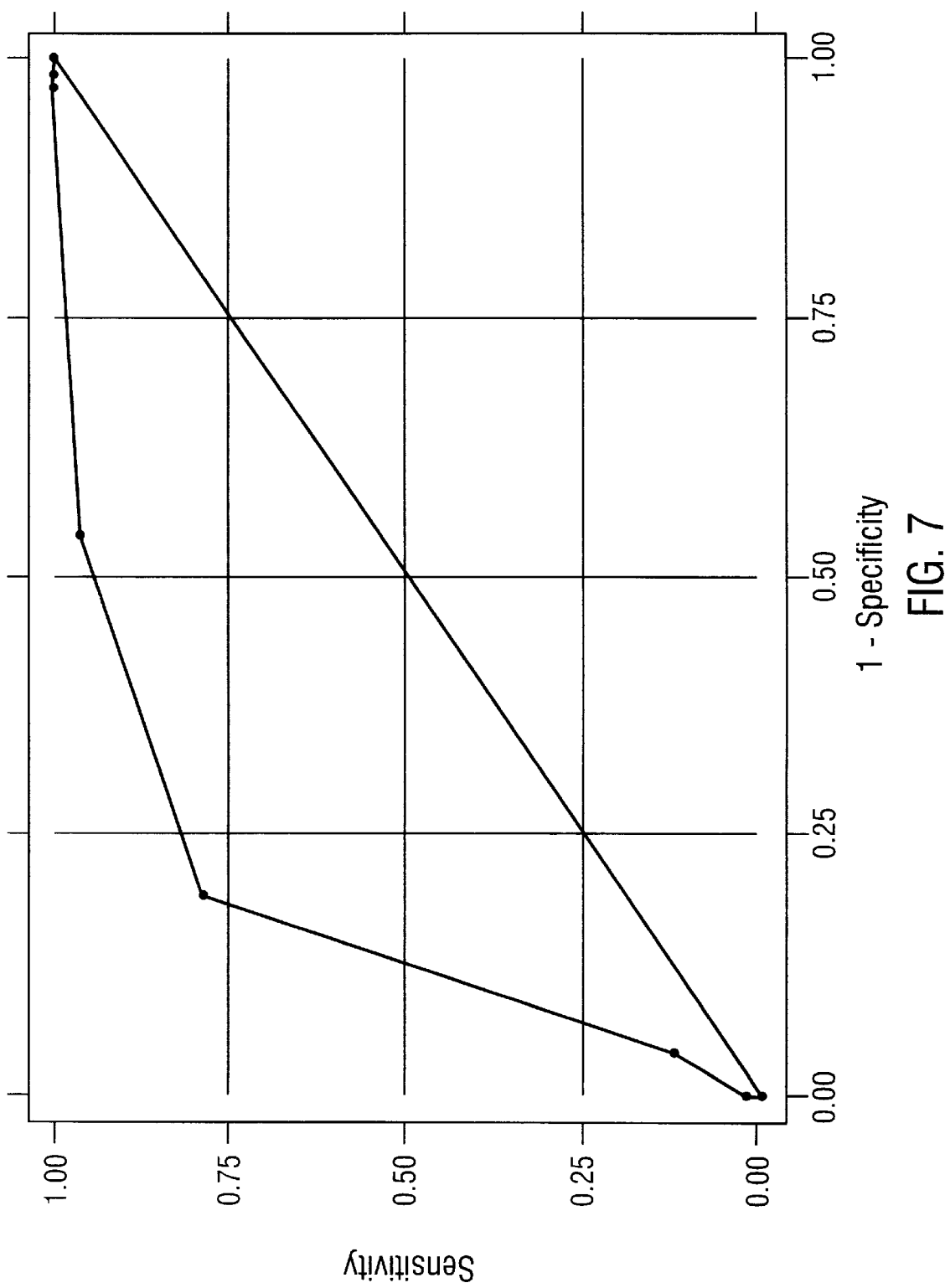
FIG. 7. Post-operative Gleason score significance in the prediction of prostate cancer progression. This figure illustrates the predictive power of Post Operative Gleason Score as a single independent variable to predict progression. A ROC curve was produced with an area under the curve of 82.62%. Please refer to Colummrn A of Table VI.
Figure 8:
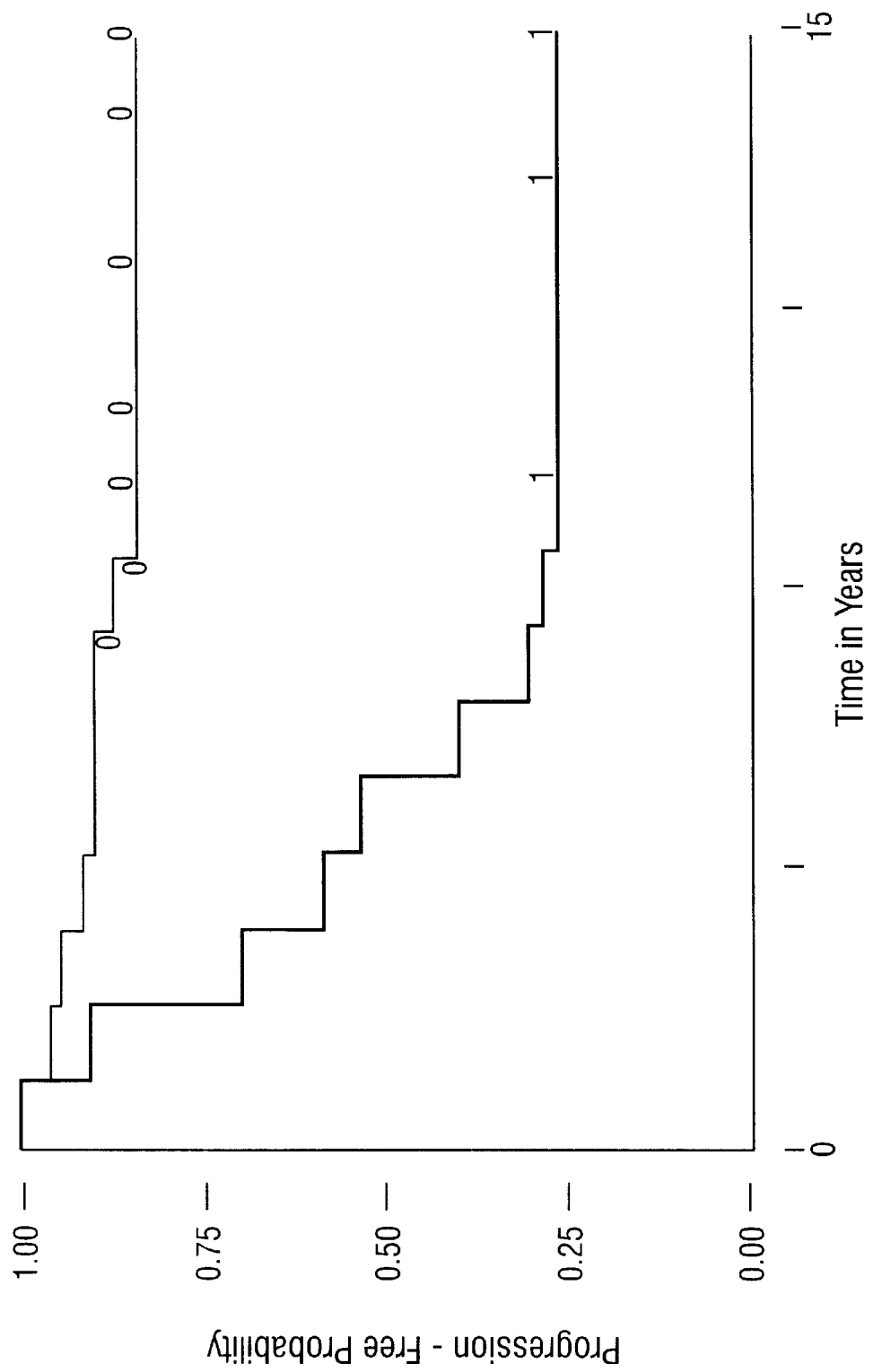
FIG. 8. Post-operative Gleason score significance in the prediction of prostate cancer progression (0=predicted not to progress; 1=predicted to progress). This figure demonstrates the ability of the Post Operative Gleason Score alone to stratify progressors and non-progressors using a Kaplan-Meier Survival Recurrence) Curve. This is the pathologic standard against which all models are tested.
Figure 9:
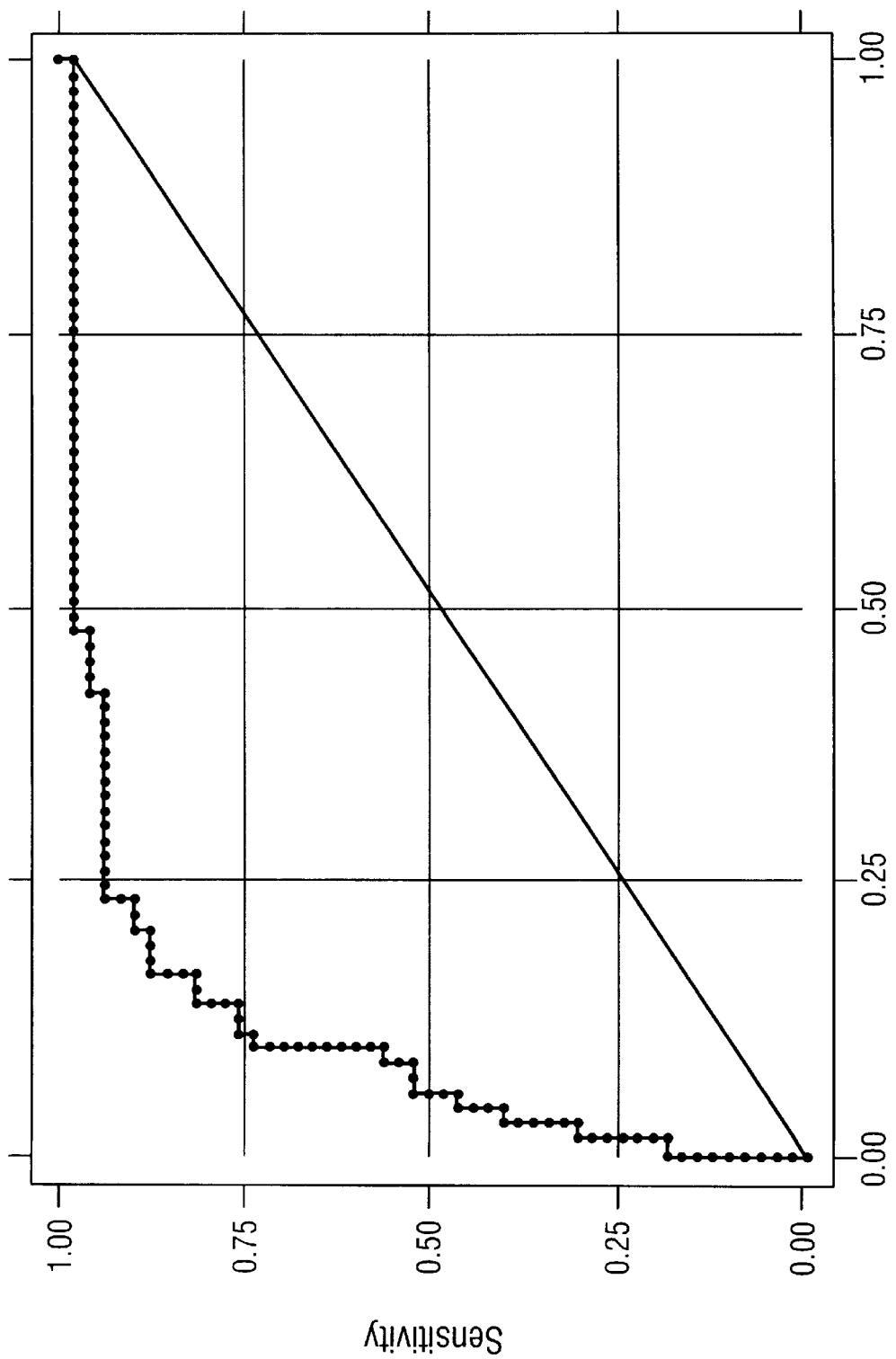
FIG. 9. Nuclear roundness variance significance in the prediction of prostate cancer progression. This figure illustrates the predictive power of Nuclear Roundness Variance (as measured by the DynaCell System at 1 00×) to predict progression. A ROC curve was produced with an area under the curve of 89.75%. Please refer to Column B of Table VI.
Figure 10:
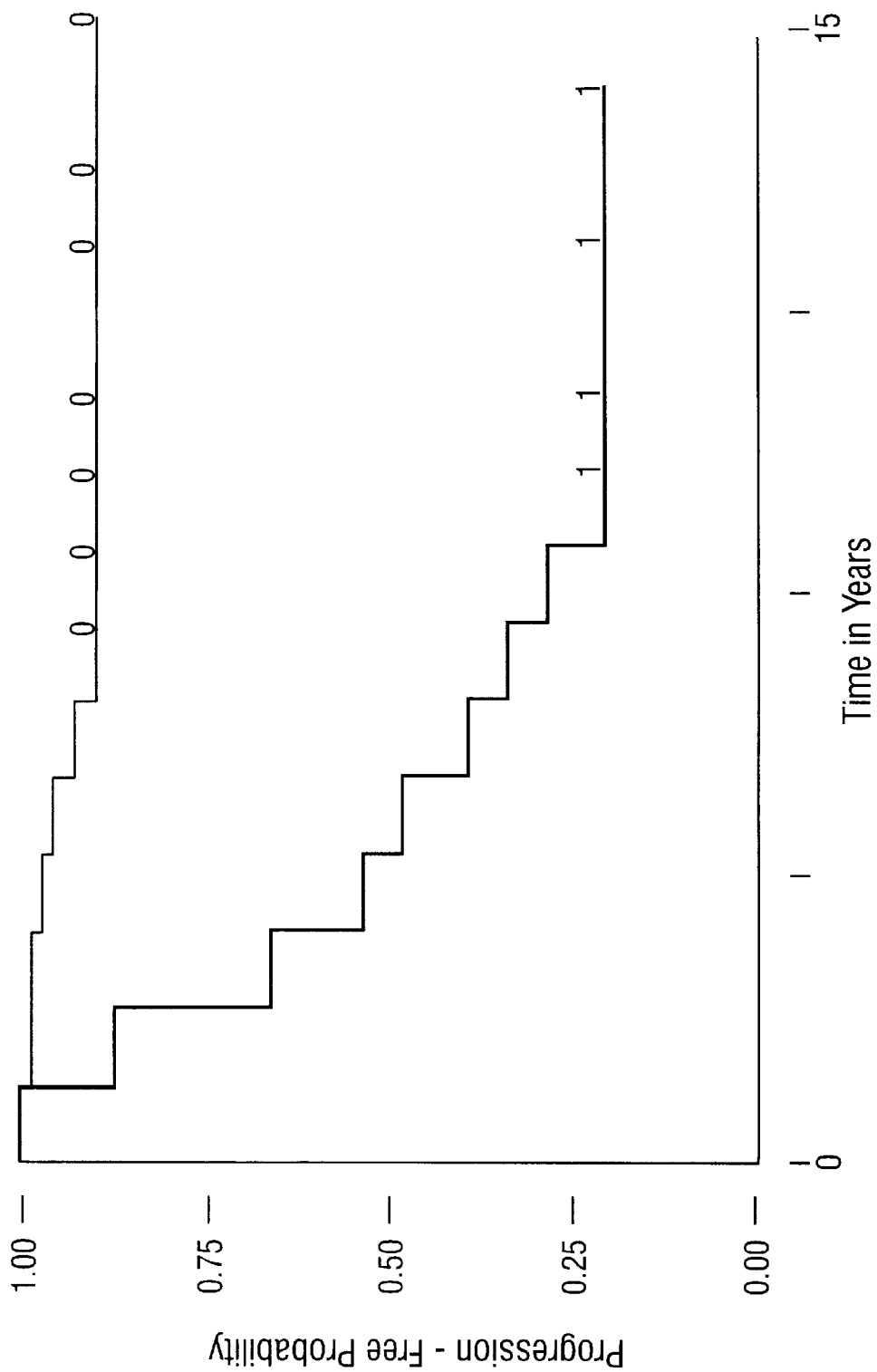
FIG. 10. Nuclear roundness variance significance in the prediction of prostate cancer progression (0=predicted not to progress; 1–predicted to progress). This figure demonstrates the ability of Nuclear Roundness Variance alone to stratify progressors and non-progressors using a Kaplan-Meier Survival (Recurrence) Curve.
Figure 11:
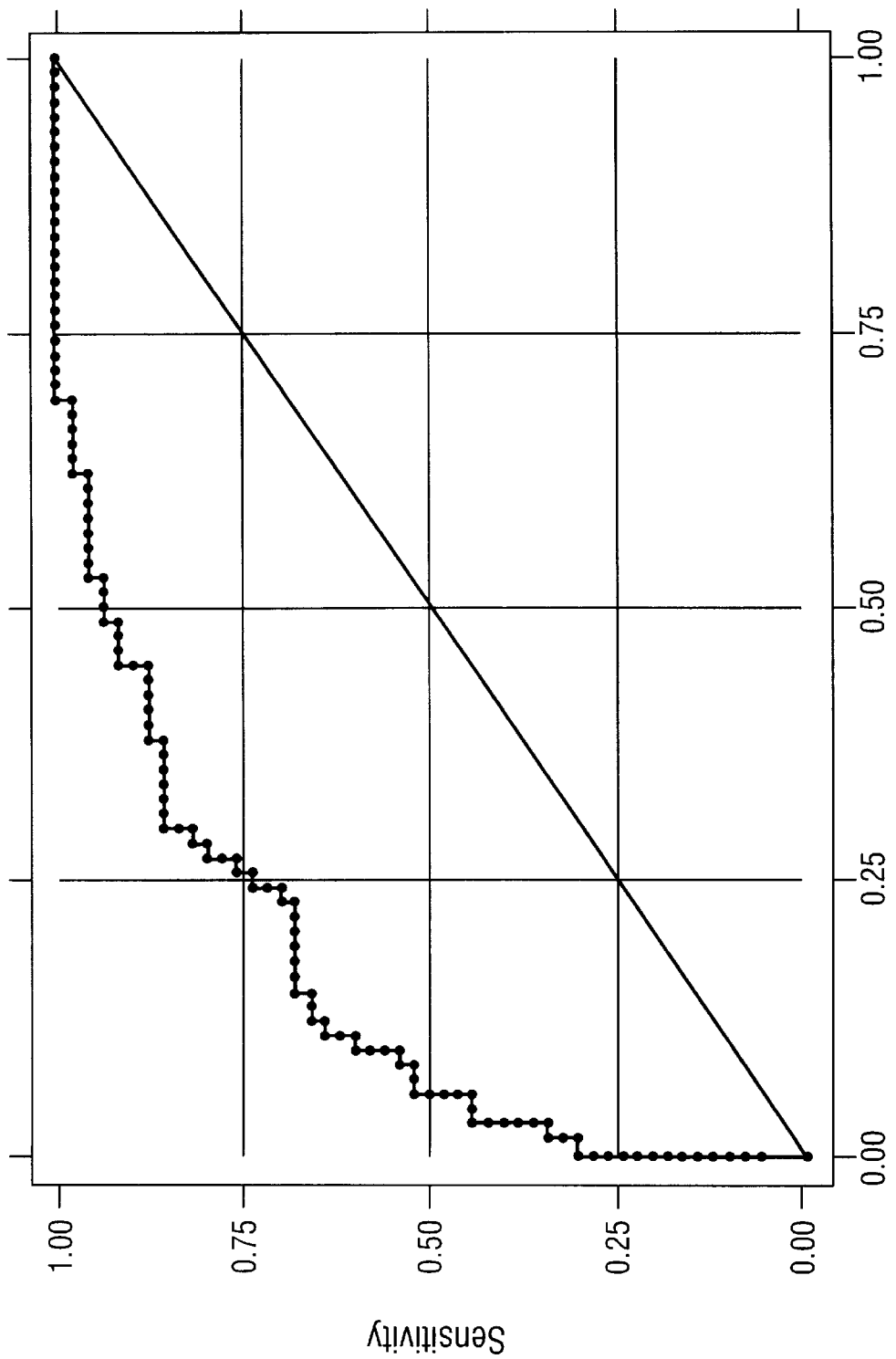
FIG. 11. 12 CMP nuclear descriptors found to be significant in the prediction of prostate cancer progression. This figure illustrates the predictive power of the 12 CMP NMD's to predict progression. A ROC curve was produced with an area under the curve of 85.57%. Please refer to Colurm D2 of Table VI.
Figure 12:
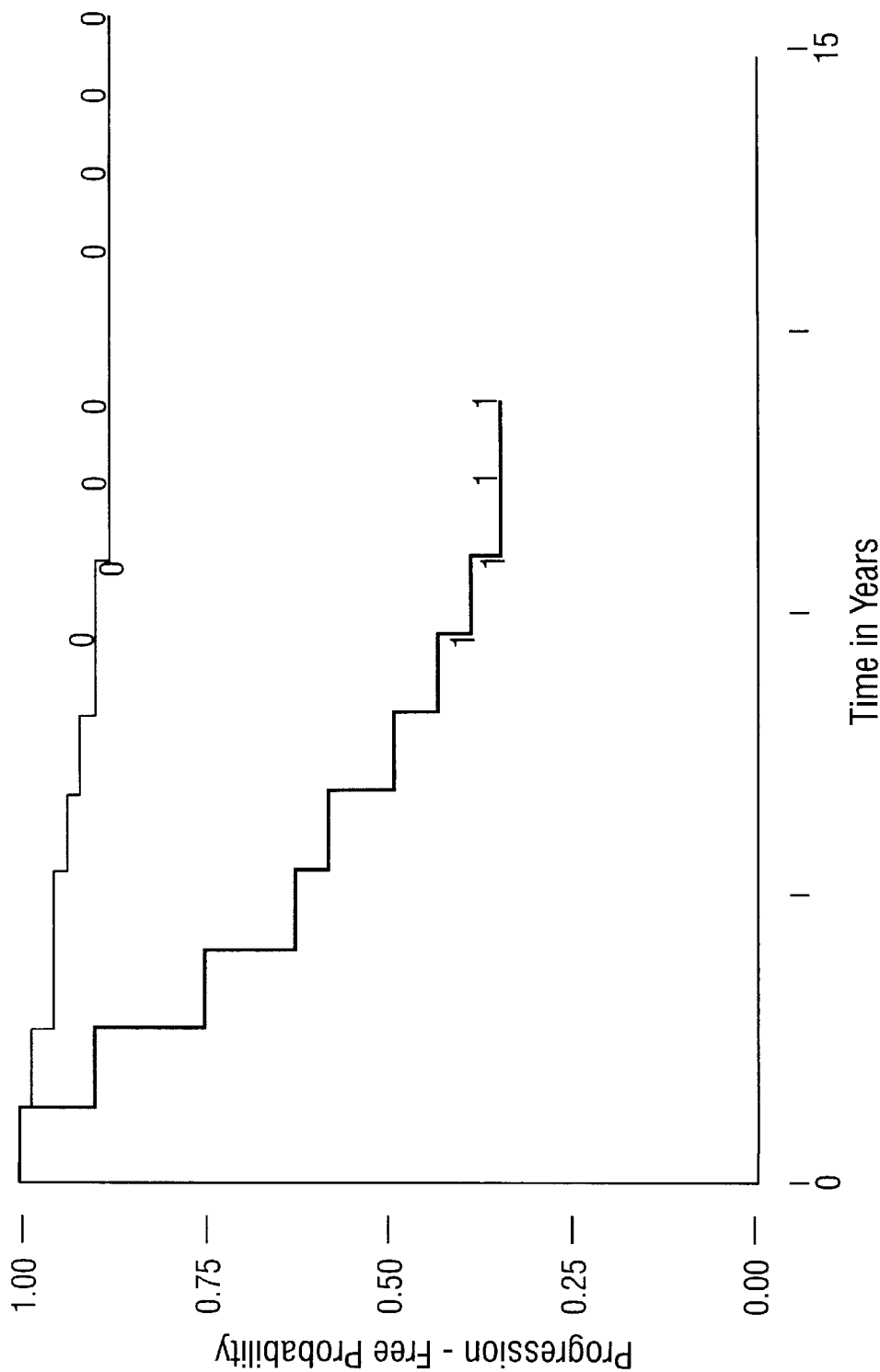
FIG. 12. 12 CMP nuclear descriptors found to be significant in the prediction of prostate cancer progression (0=predicted not to progress; 1=predicted to progress). This figure demonstrates the ability of the 12 CMP NMD's to stratify progressors and non-progressors using a Kaplan-Meier Survival (Recurrence) Curve.
Figure 13:
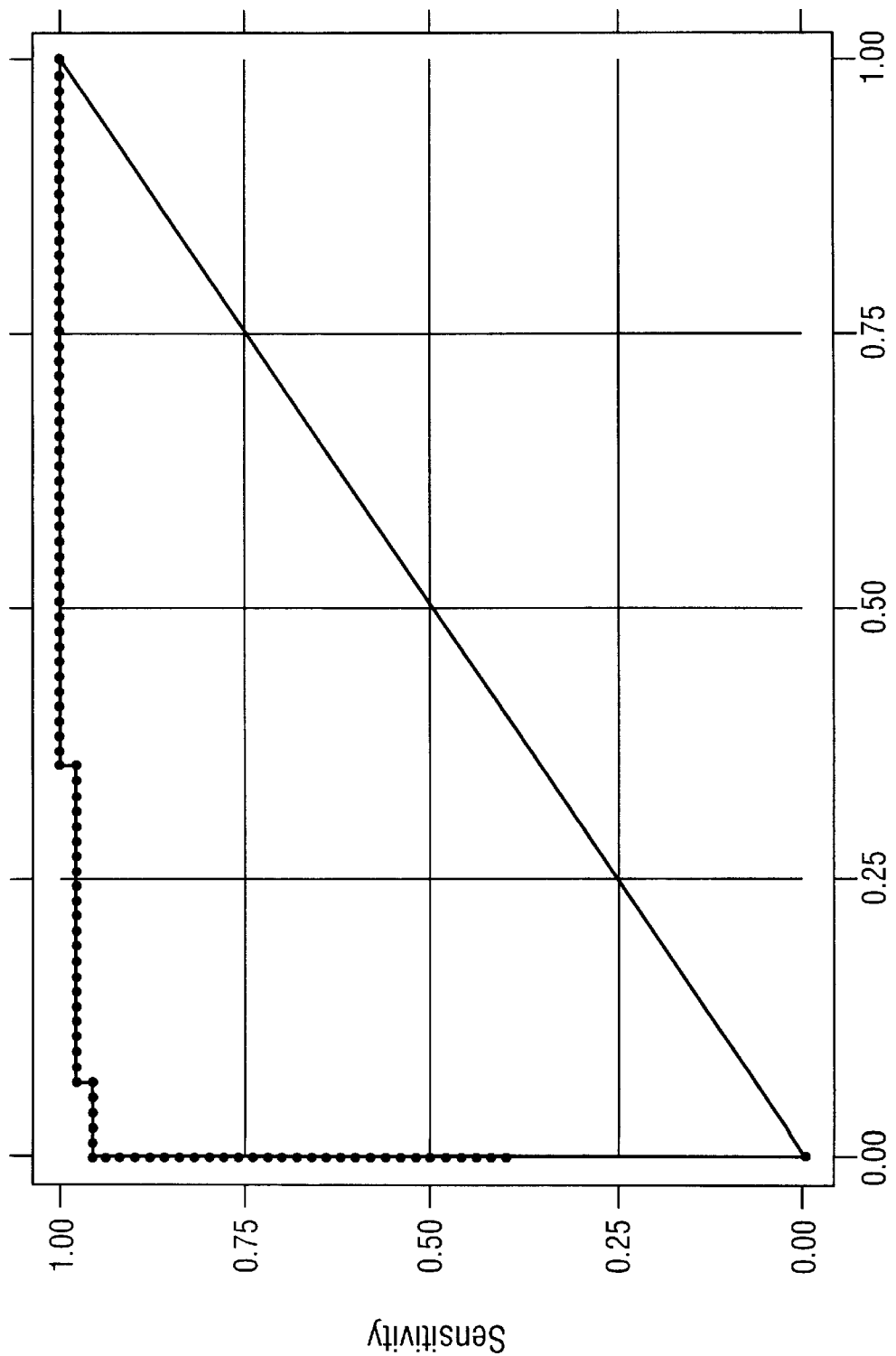
FIG. 13. 13 CMP nuclear descriptors, Her-2/neu staining, nuclear roundness variance, and post-op Gleason found to be significant in the prediction of prostate cancer progression. This figure illustrates the predictive power of the 13 CMP NMD's, 1 biomarker, NRV, and Gleason Score combined to predict progression. A ROC curve was produced with an area under the curve of 99.15%. Please refer to Column N of Table VI.
Figure 14:
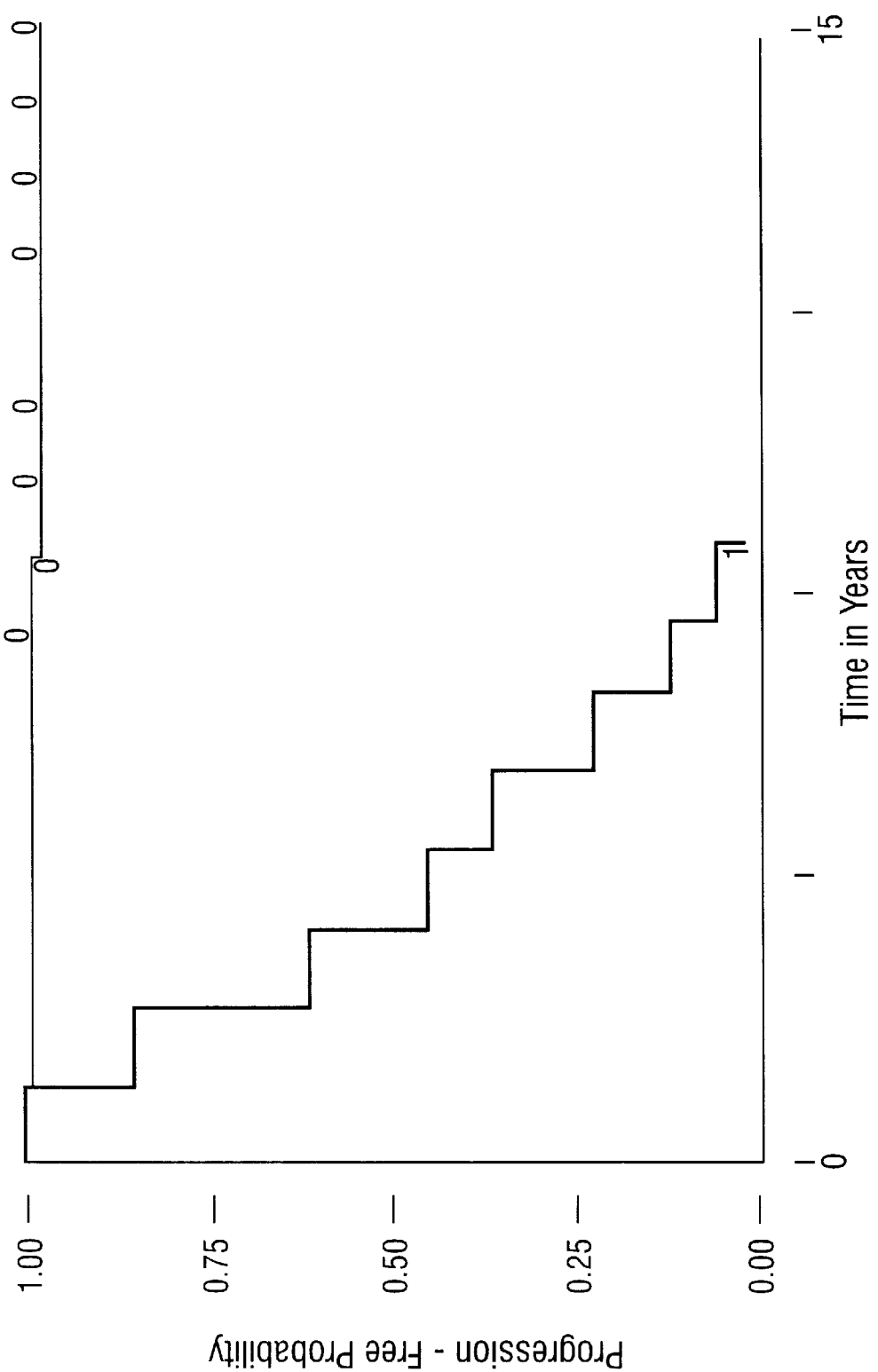
FIG. 14. 13 CMP nuclear descriptors, Her-2/neu staining, nuclear roundness variance, and post-op Gleason found to be significant in the prediction of prostate cancer progression (0=predicted not to progress; 1=predicted to progress). This figure demonstrates the ability of the 13 CMP NMD's, 1 biomarker, NRV, and Gleason Score combined to stratify progressors and non-progressors using a Kaplan-Meier Survival (Recurrence) Curve.
Figure 15:
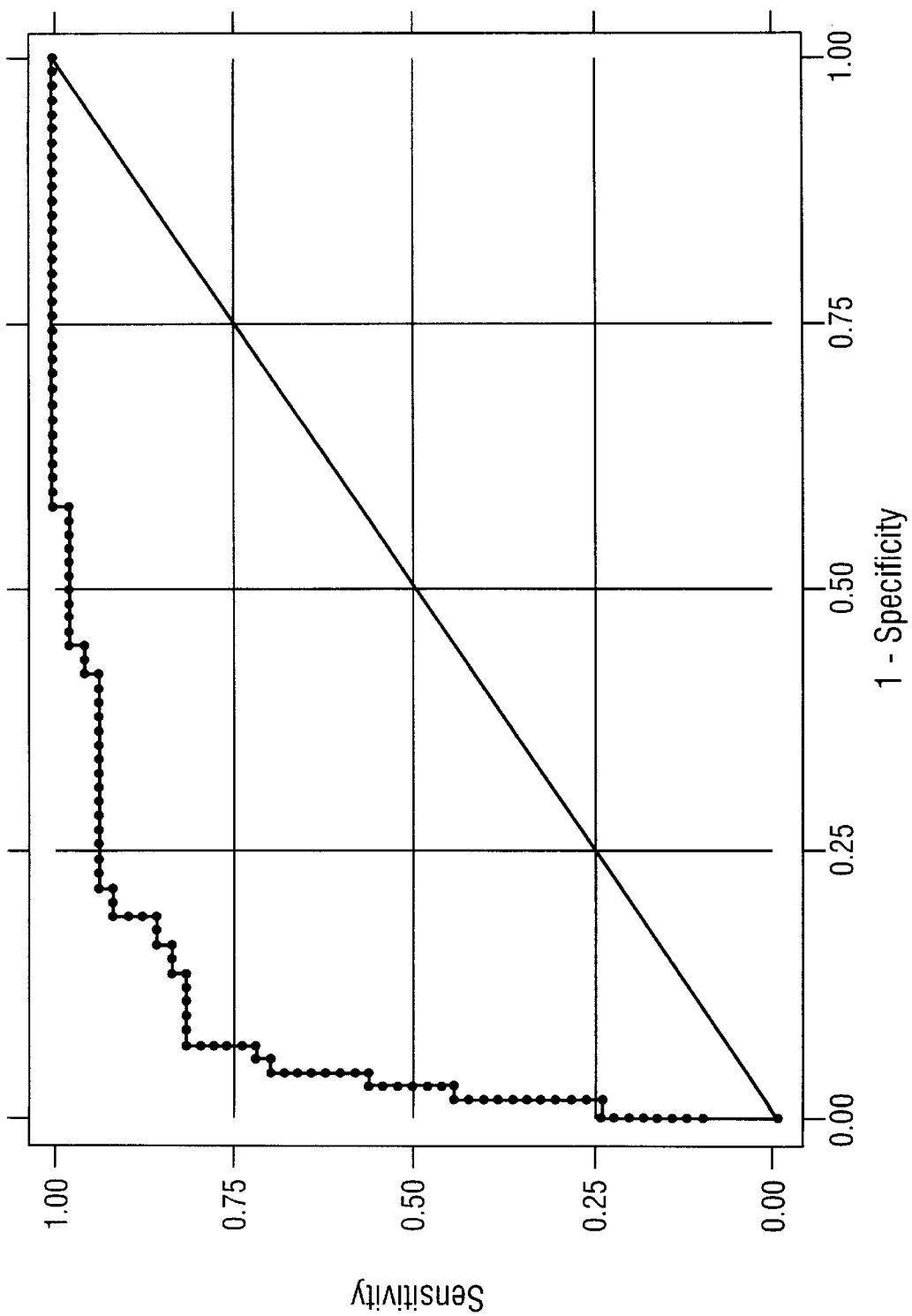
FIG. 15. 19 JVB nuclear descriptors found to be significant in the prediction of prostate cancer progression. This figure illustrates the predictive power of the 19 JVB NMD's to predict progression. A ROC curve was produced with an area under the curve of 93%. Please refer to Column D2 of Table VII. Also, please note the difference in the number of features required for JVB NMD's as well as an increase the predictive power of the model as compared to CMP NMD's in FIG. 10.
Figure 16:
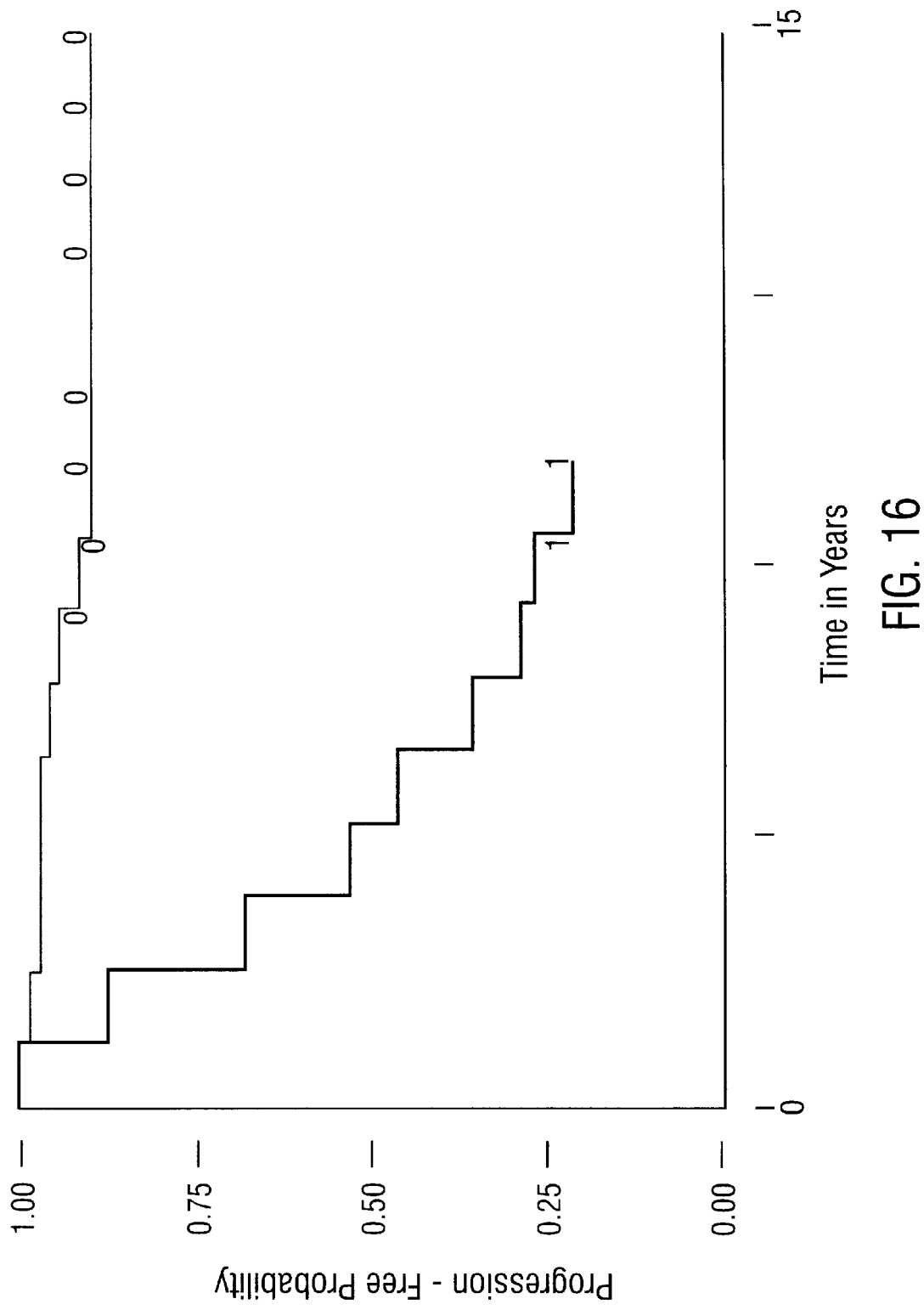
FIG. 16. 19 JVB nuclear descriptors found to be significant in the prediction of prostate cancer progression (0=predicted not to progress; 1=predicted to progress). This figure demonstrates the ability of the 19 JVB 3 NMD's to stratify progressors and non-progressors using a Kaplan-Meier Survival (Recurrence) Curve. Please note the difference in the ability of JVB NMD's to stratify progressors and non-progressors as compared to CMP NMD's in FIG. 11.
Figure 17:
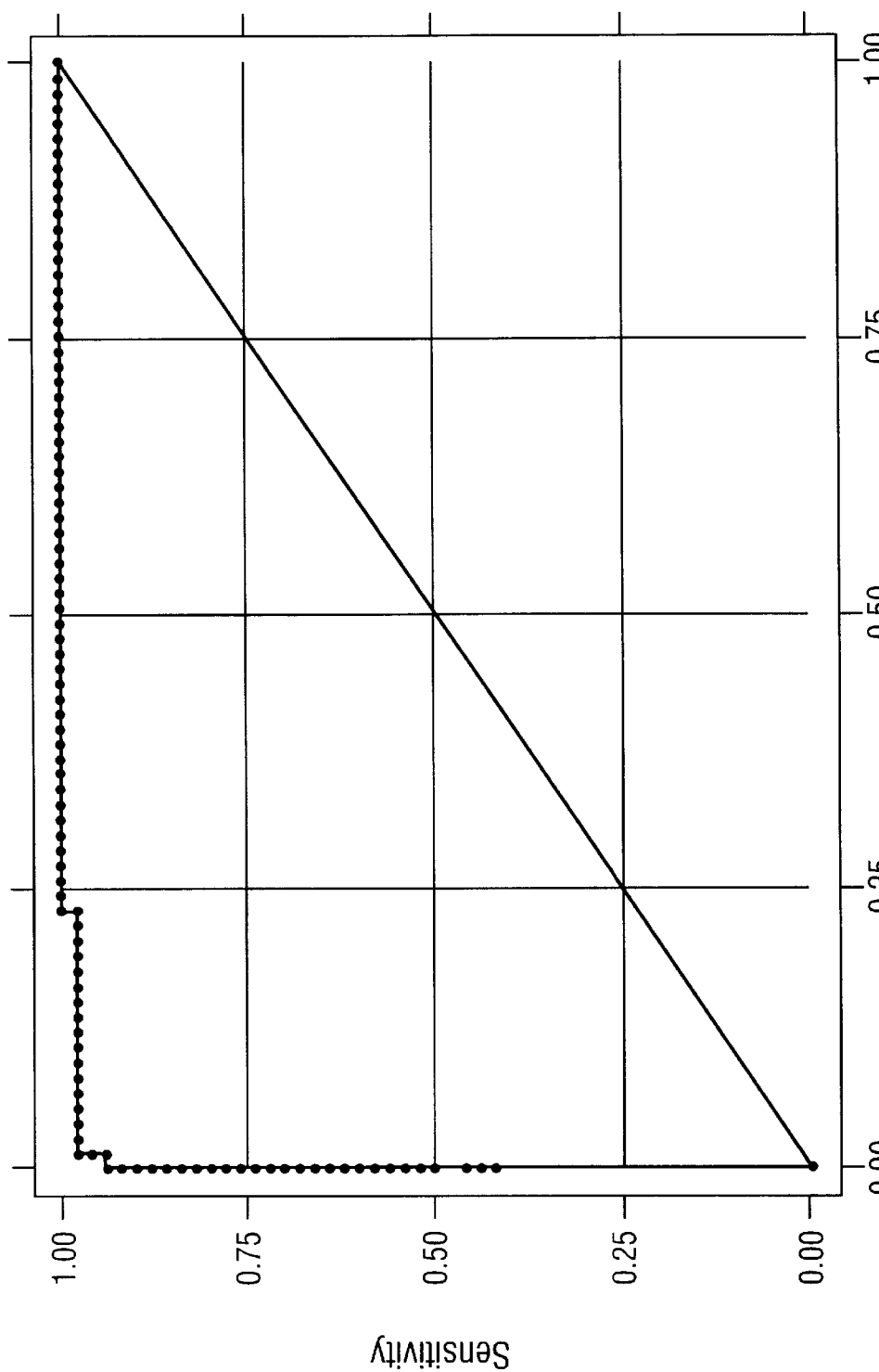
FIG. 17. 14 JVB nuclear descriptors, 2 biomarkers, nuclear roundness variance, and post-op Gleason found to be significant in the prediction of prostate cancer progression. This figure illustrates the predictive power of the 14 JVB NMD's, 2 biomarkers, NRV, and Gleason Score combined to predict progression. A ROC curve was produced with an area under the curve of 99.48%. Please refer to Column N of Table VII.
Figure 18:
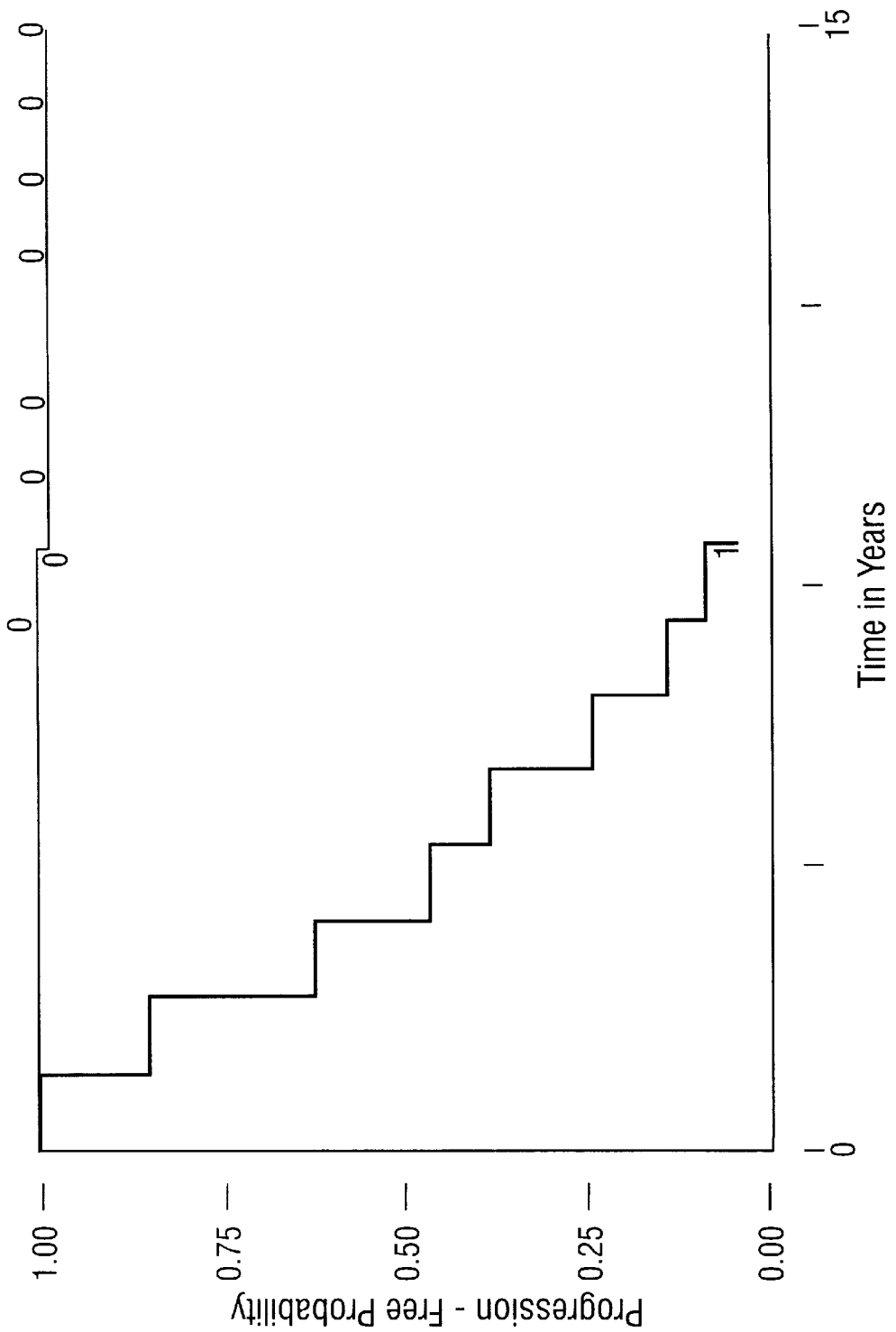
FIG. 18. 14 WB nuclear descriptors, 2 biomarkers, nuclear roundness variance, and post-op Gleason found to be significant in the prediction of prostate cancer progression (0=predicted not to progress; 1=predicted to progress). This FIG. demonstrates the ability of the 14 JVB NMD's, 2 biomarkers, NRV, and Gleason Score combined to stratify progressors and non-progressors using a Kaplan-Meier Survival (Recurrence) Curve.
Figure 19:
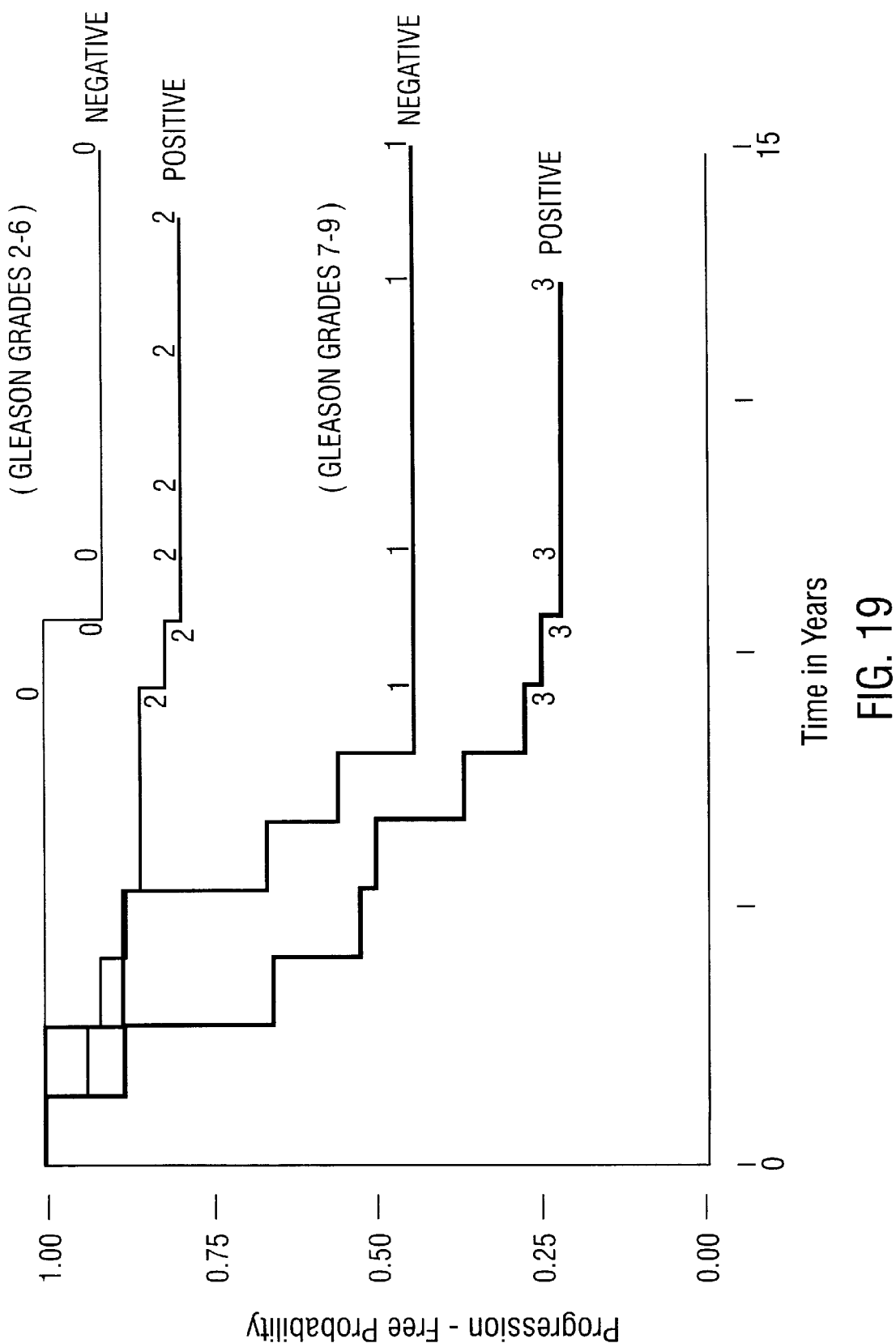
FIG. 19. Stratification of progressors among well to moderately differentiated prostate cancers using Her-2/neu antigenic expression (Kaplan-Meier Survival (Recurrence) Curve).
Figure 20:
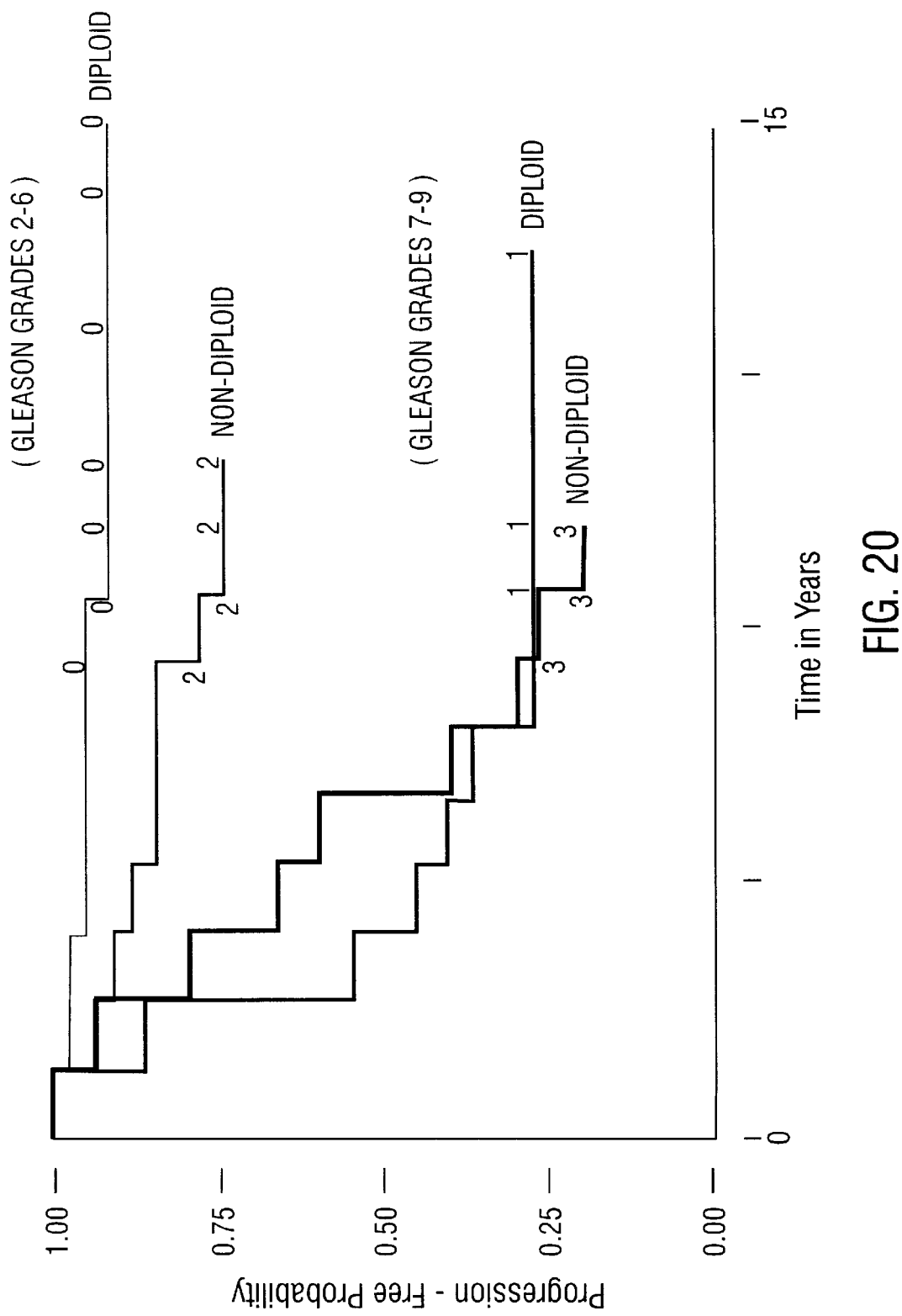
FIG. 20. Stratification of progressors among well to moderately differentiated prostate cancers using DNA ploidy cytometry (Kaplan-Meier Survival (Recurrence) Curve).
Figure 21:
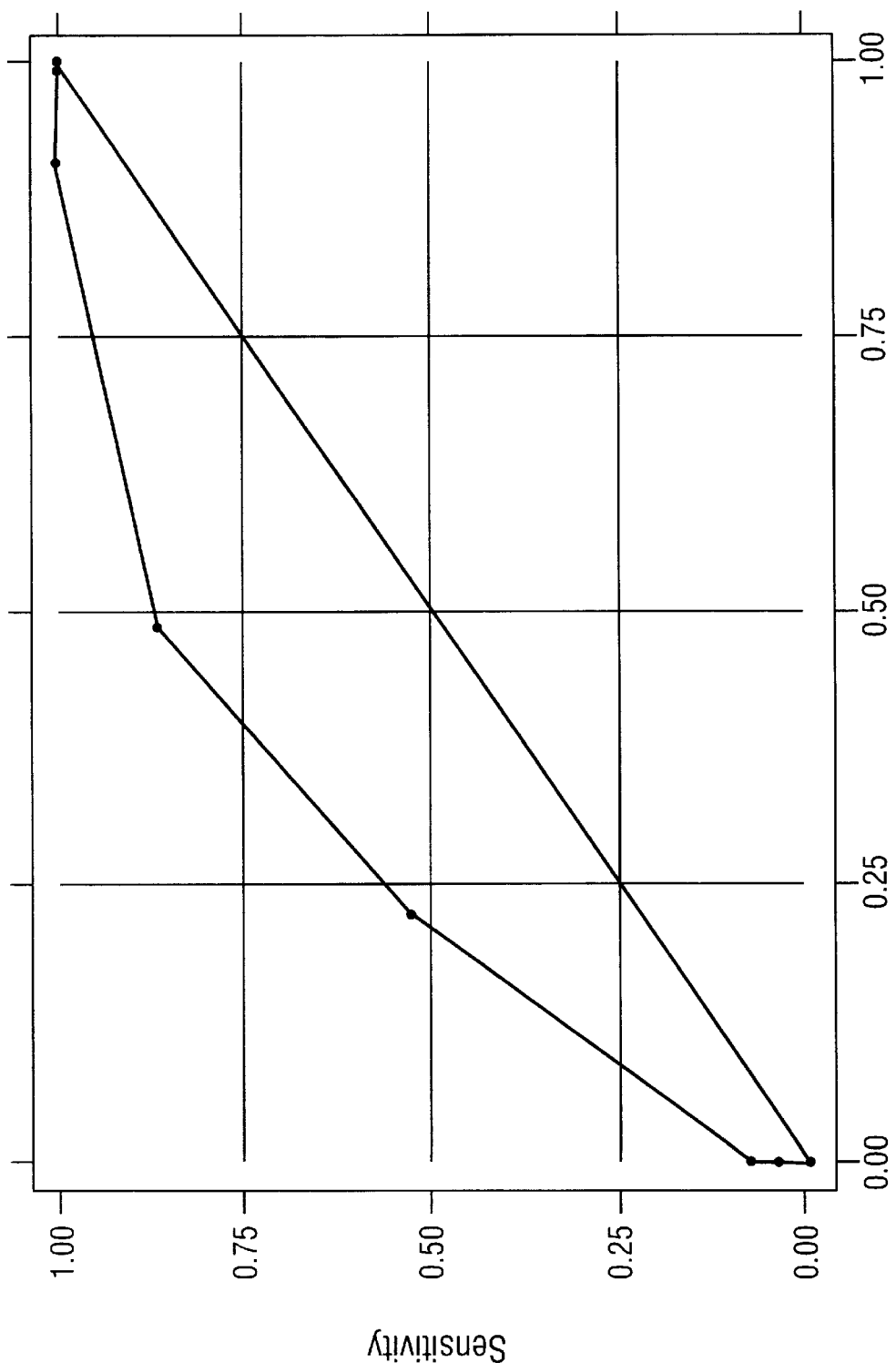
FIG. 21. Post-operative Gleason score significance in the prediction of organ confinement status. This figure illustrates the predictive power of Post Operative Gleason Score to predict organ confined disease status A ROC curve was produced with an area under the curve of 73.3%. Please refer to Column A of Table IX. Note the lower predictive value of this independent variable as compared to the same variable used to predict progression (see FIG. 6).
Figure 22:
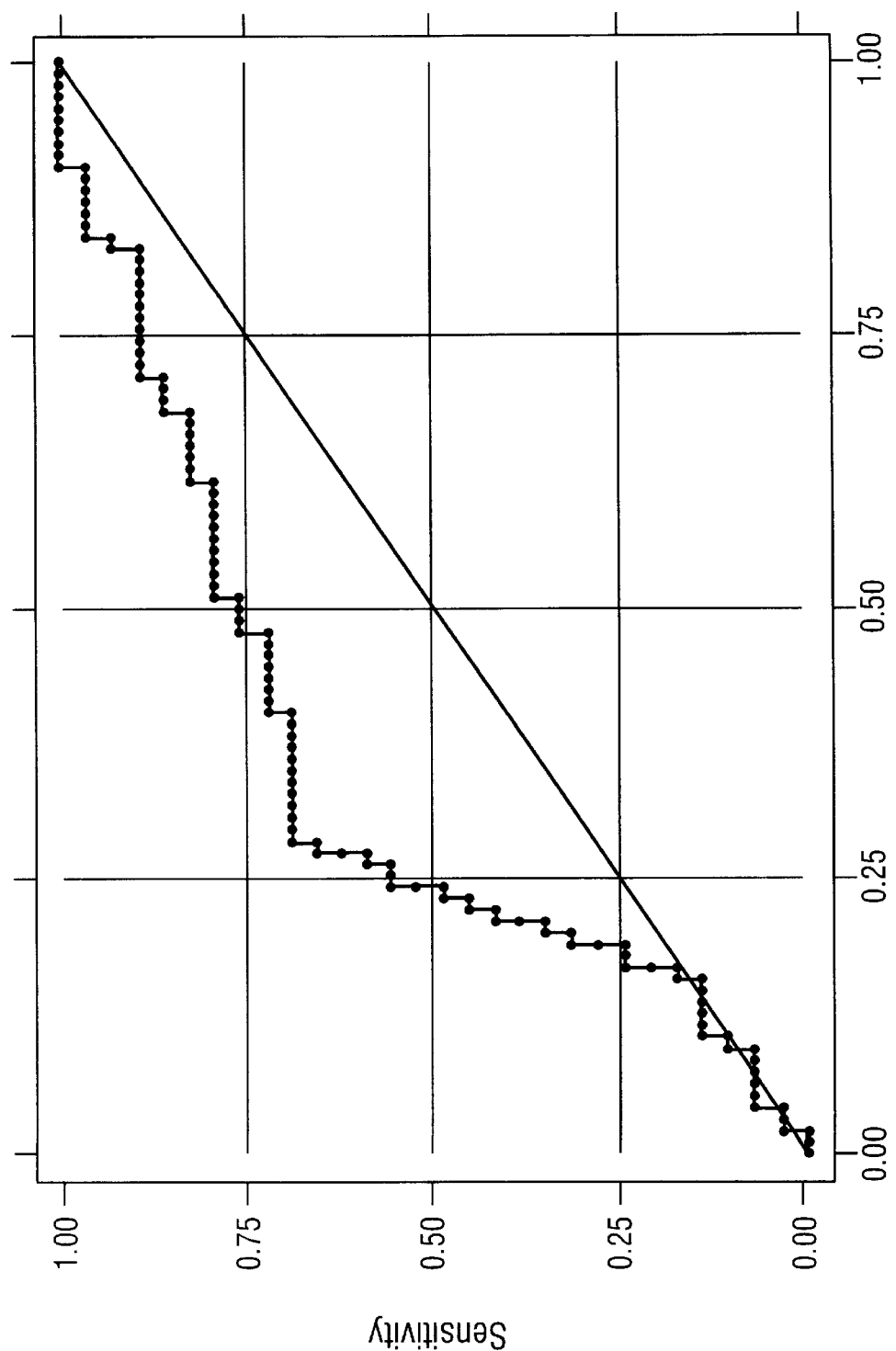
FIG. 22. Nuclear roundness variance significance in the prediction of organ confinement status. This figure illustrates the predictive power of Nuclear Roundness Variance to predict organ confined disease status. A ROC curve was produced with an area under the curve of 66.18%. Please refer to Column B of Table IX. Once again note the much lower predictive value of this independent variable compared to its contribution in prediction progression (see FIG. 9).
Figure 23:
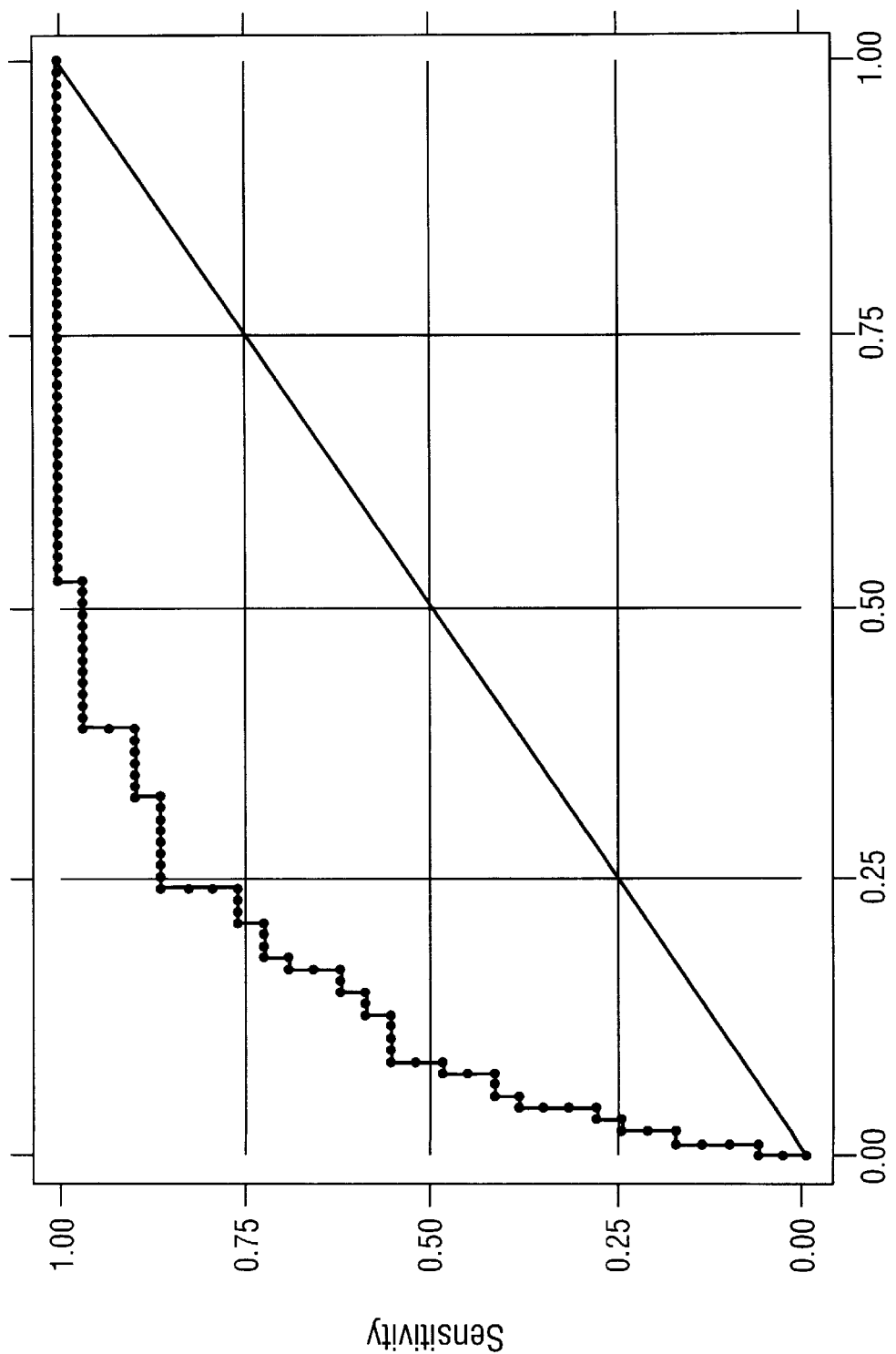
FIG. 23. 10 CMP nuclear descriptors found to be significant in the prediction of organ confinement status. This figure illustrates the predictive power of the 10 CMP NMD's to predict organ confined disease status. A ROC curve was produced with an area under the curve of 86.35%. Please refer to Column D2 of Table IX. Note the significant improvement of the CMP NMD's alone as compared to NRV alone (FIG. 22) in the prediction of organ confined disease status.
Figure 24:
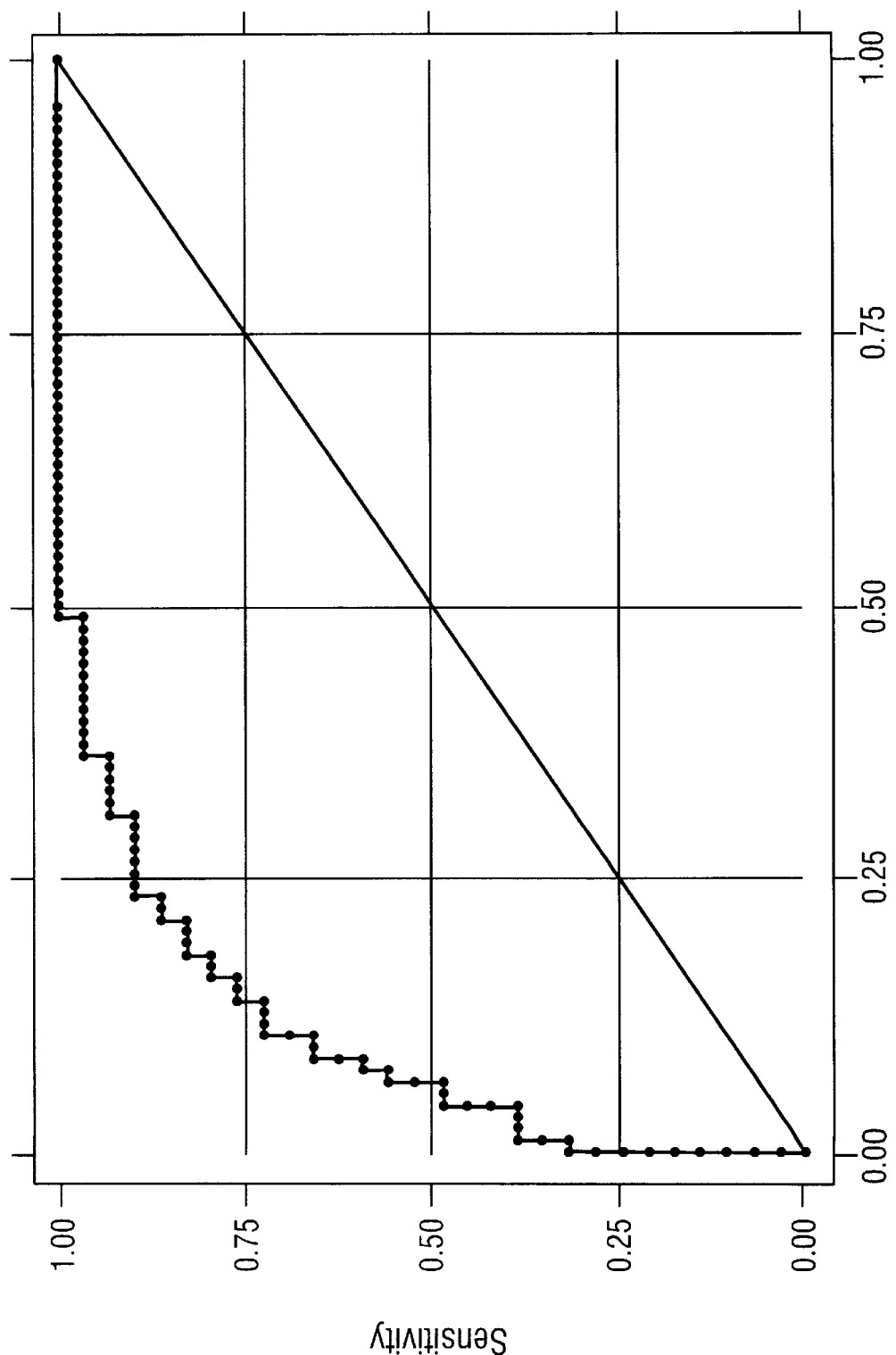
FIG. 24. 12 CMP nuclear descriptors, 3 biomarkers, and nuclear roundness variance found to be significant in the prediction of organ confinement status. This figure illustrates the predictive power of the 12 CMP NMD's, 3 biomarkers, and NRV to predict organ confined disease status. A ROC curve was produced with an area under the curve of 90.28%. Please refer to Column M of Table IX.
Figure 25:
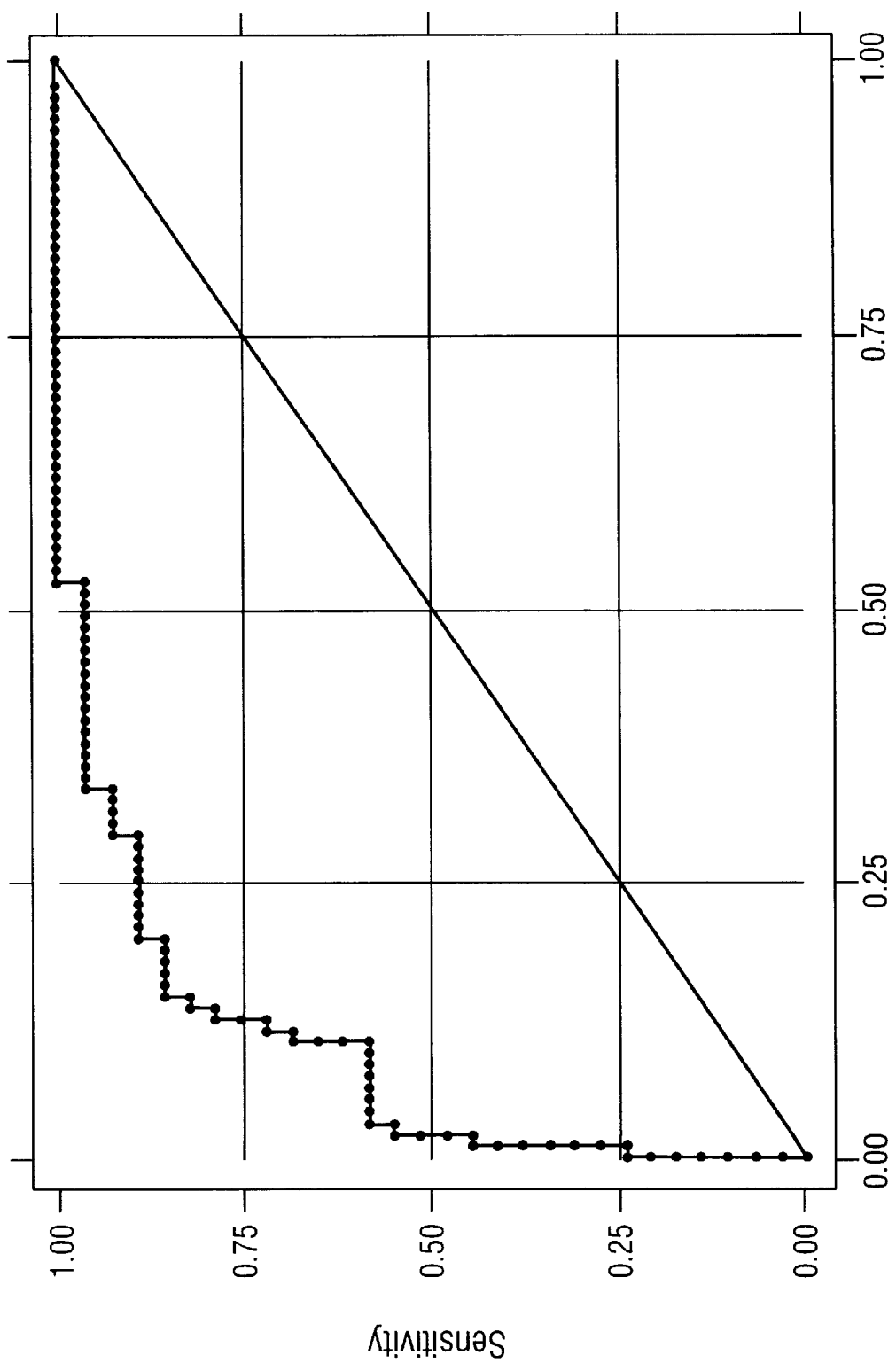
FIG. 25. 15 JVB nuclear descriptors found to be significant in the prediction of organ confinement status. This figure illustrates the predictive power of the 15 JVB NMD's to predict organ confined disease status. A ROC curve was produced with an area under the curve of 91.43%. Please refer to Column D2 of Table X. Note the improvement of predictive power when using JVB NMD's alone as compared to CMP NMD's alone (FIG. 22) in the prediction of organ confined disease status.
Figure 26:
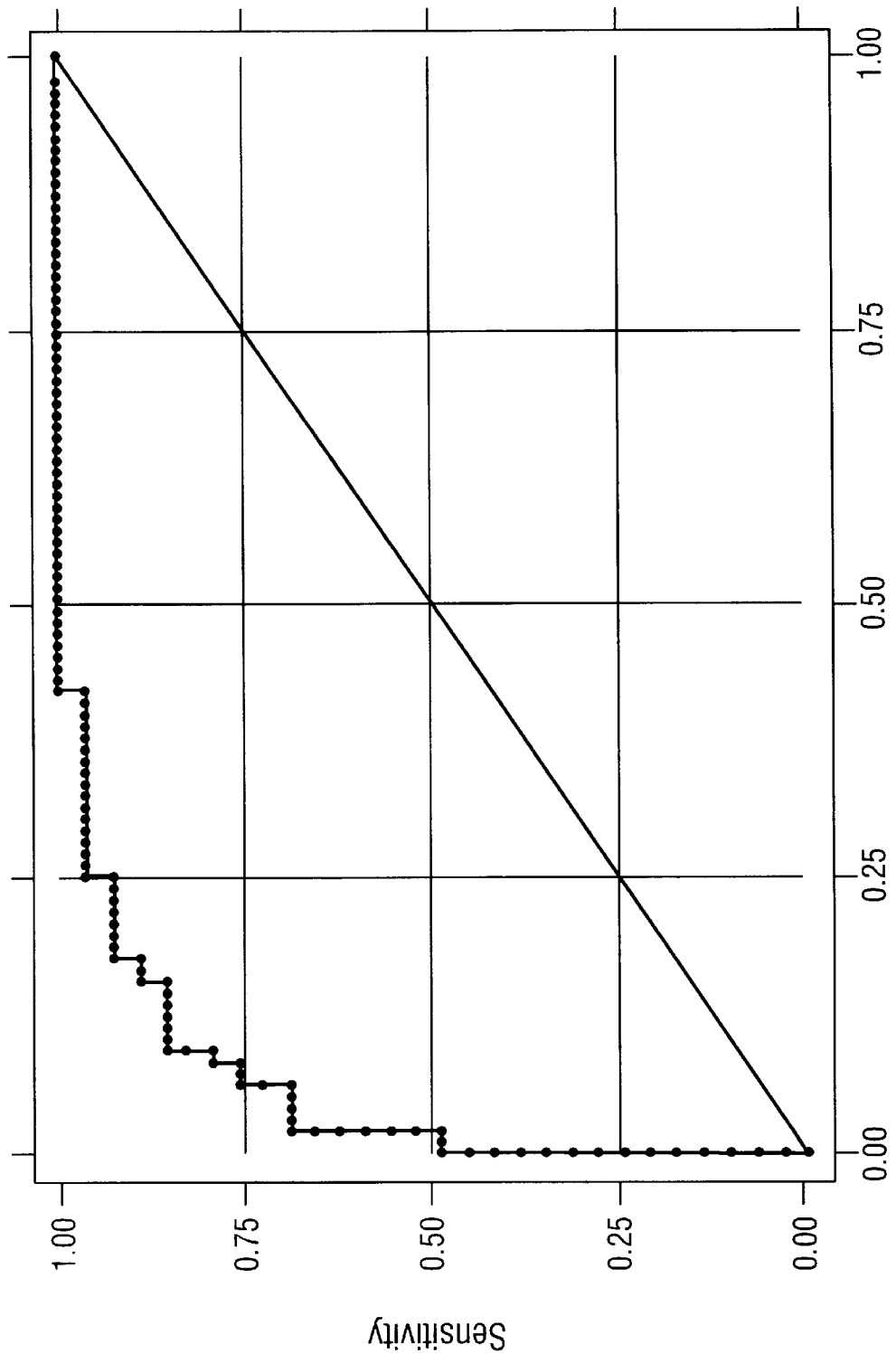
FIG. 26. 15 JVB nuclear descriptors and post-op Gleason found to be significant in the prediction of organ confinement status. This figure illustrates the predictive power of the 15 JVB NMD's and Post Operative Gleason score to predict organ confined disease status. A ROC curve was produced with an area under the curve of 94.7%. Please refer to Column H of Table X.
Figure 27:
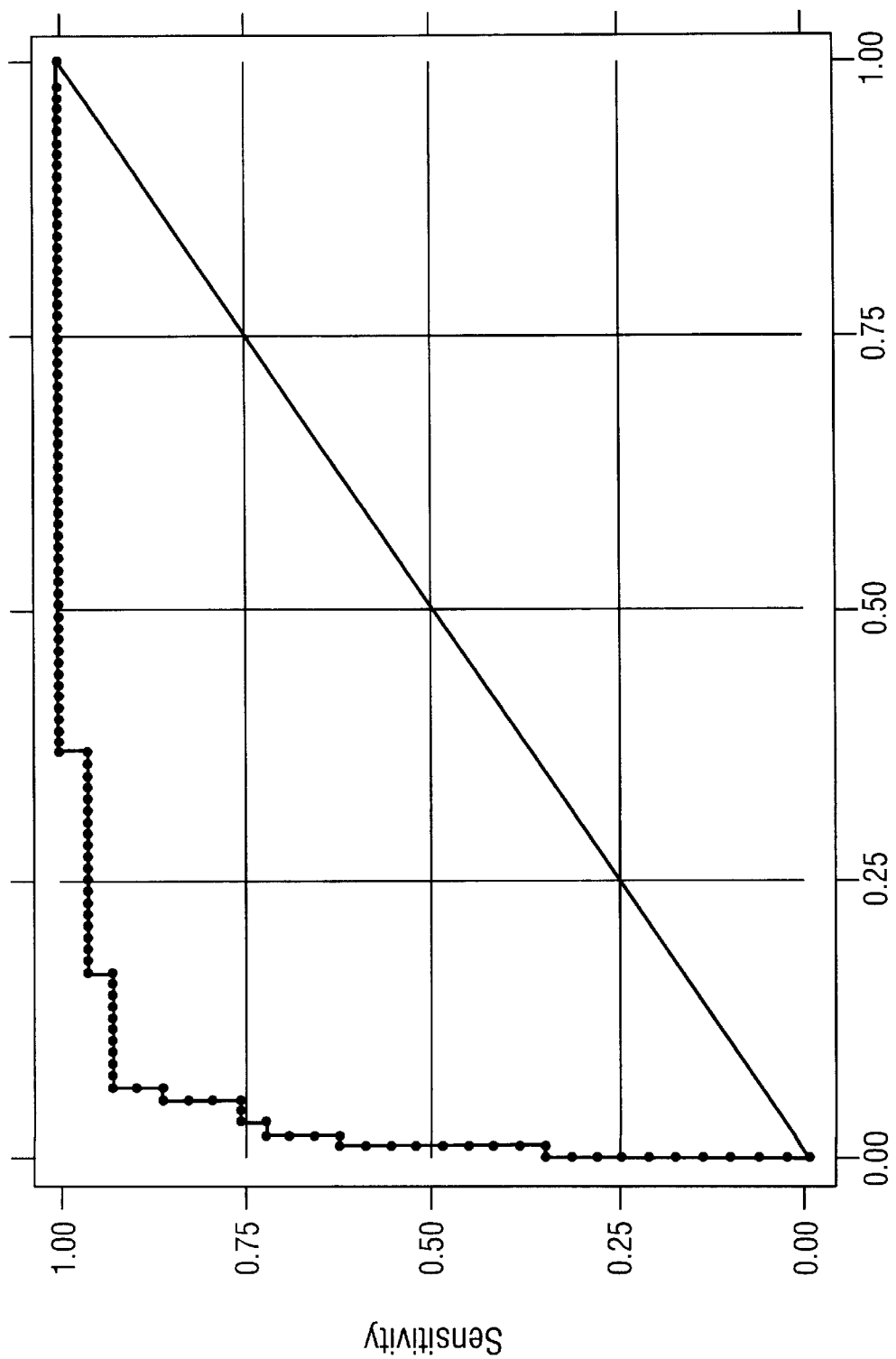
FIG. 27. 16 JVB nuclear descriptors, 3 biomarkers, nuclear roundness variance (DROPPED), and post-op Gleason found to be significant in the prediction of organ confinement status. This figure illustrates the predictive power of the 16 JVB NMD's, 3 biomarkers, and Post Operative Gleason score to predict organ confined disease status- A ROC curve was produced with an area under the curve of 96.55%. Please refer to Column N of Table X. Note that NRV was dropped as a significant independent variable in this model.

The invention, in its broadest sense, is a method for predicting organ confined disease status or the potential for progression of prostate cancer following radical surgery using either non-parametric statistical analysis methods or neural networks. The parameters assessed by these methods include, but are not limited to, cellular biomarkers and nuclear morphometric descriptors. The invention provides a method to collect nuclear images and extract all relevant shape, size, Markovian texture, and DNA content features important to construction of a mathematical method that gives a single predictive probability for prostate cancer progression or organ localization, with or without pathological grading. The texture features utilized in the present invention are set forth in Table I (CMP v3.0) and Table II (JVB v1.0). It is recognized that in predicting the probability of prostate cancer progression and organ localization, prognostic variable factors other than those listed may be used within the scope and spirit of the present invention.

Also embodied in the present invention is the use of a trained neural network to provide a single predictive probability for prostate cancer progression or organ localization given any number of inputs. The multi-layer perceptron network of the present invention is a feed-forward network with one or more hidden layers of neurons between the input and output layers. Using this architecture, many shortcomings of the single layer perceptron are avoided. However, because of the added complexity, the convergence theorem and weight adjustment procedure suggested by Rosenblatt is not applicable. An alternate procedure called "back propagation" has been independently developed by Werbos (Werbos, Ph.D. Thesis, Harvard University, 1974), Parker (Parker, Innovation Report, 581–664, File 1, Office of Technology Licensing, Stanford University, October, 1982), and Rumelhart (see Rumelhart et al., Parallel Distributed Processing Explorations in the Microstructures of Cognition Vol. 1, Foundations, MIT Press, Cambridge, Mass., 1988). This procedure is effective and allows for efficient use of multi-layer perceptrons. But the procedure does not guarantee convergence to the global minima at all times. Also, it requires a large number of training iterations in order to learn a given set of transformations.

Because of the problems associated with back propagation, it is of interest to modify the weight adjustment procedure and/or the model developed by Rosenblatt to enable single-layer perceptrons to solve problems such as XOR problems. In this work, a modified perceptron is utilized. The modified perceptron used is a multiple threshold perceptron that is capable of solving XOR problems. This modified perceptron is obtained by changing the non-linearity function. Unlike previous efforts in developing multiple threshold perceptrons, the perceptron of the present invention is capable of handling both binary and analog inputs. The procedure requires fewer number of iterations to develop appropriate input to output transformations when compared to back propagation.

For the purposes of this invention, the following clinical and pathological staging criteria is used. The use of other criteria does not depart from the scope and spirit of the invention.

TO—No evidence of Prostatic tumor.

T1—Clinically inapparent tumor, non-palpable nor visible by imaging.
  T1a—Tumor is incidental histologic finding with three or fewer microscopic foci. Non-palpable, with 5% or less of TURP chips (trans-urethral resected prostate tissue) positive for cancer.
  T1b—Tumor is incidental histologic finding with more than three microscopic foci. Non-palpable, with greater then 5% of TURP chips (trans-urethral resected prostate tissue) positive for cancer.
  T1c—Tumor is non-palpable, and is found in one or both lobes by needle biopsy diagnosis.

T2—Tumor is confined within the prostate.
  T2a—Tumor present clinically or grossly, limited to the prostate, tumor 1.5 cm or less in greatest dimension, with normal tissue on at least three sides. Palpable, half of 1 lobe or less.
  T2b—Tumor present clinically or grossly, limited to the prostate, tumor more than 1.5 cm in greatest dimension, or in only one lobe. Palpable, greater than half of 1 lobe but not both lobes.
  T2c—Tumor present clinically or grossly, limited to the prostate, tumor more than 1.5 cm in greatest dimension, and in both lobes. Palpable, involves both lobes.

T3—Tumor extends through the prostatic capsule. T3a—
  Palpable tumor extends unilaterally into or beyond the prostatic capsule, but with no seminal vesicle or lymph node involvement. Palpable, unilateral capsular penetration.
  T3b—Palpable tumor extends bilaterally into or beyond the prostatic capsule, but with no seminal vesicle or lymph node involvement. Palpable, bilateral capsular penetration.
  T3c—Palpable tumor extends unilaterally and or bilaterally beyond the prostatic capsule, with seminal vesicle and/or lymph node involvement. Palpable, seminal vesicle or lymph node involvement.

T4—Tumor is fixed or invades adjacent structures other than the seminal vesicles or lymph nodes.
  T4a—Tumor invades any of: bladder neck, external sphincter, rectum.
  T4b—Tumor invades levator muscles and/or is fixed to pelvic wall.

The following examples are included to demonstrate preferred embodiments of the invention. It should be appreciated by those of skill in the art that the techniques disclosed in the examples that follow represent techniques discovered by the inventor to function well in the practice of the invention, and thus can be considered to constitute preferred modes for its practice. However, those of skill in the art should, in light of the present disclosure, appreciate that many changes c an be made in the specific embodiments that are disclosed and still obtain a like or similar result without departing from the spirit and scope of the invention.

EXAMPLE I

DNA Staining Procedure Using CAS Quantitative DNA Staining Kit (Elmhurst, Ill.; Catalog #102300-01)

Preparation of Feulgen Stain Solution:

Place 90 ml of Type I $H_2O$ in a volumetric flask and add 10 ml of 1N HCL. Place a stir bar in a 125 ml Erlenmeyer flask and add the above solution. Add 1 vial of DNA stain reagent to the flask while stirring the solution. Place a rubber stopper in the flask, and stir the contents for at least 1 hour. This Feulgen stain solution should be filtered through a Whatman No. 1 filter immediately before staining of the specimen.

Preparation of Feulgen Rinse Solution:

Place 285 ml of Type I $H_2O$ in a 500 ml graduated cylinder and add 15 ml of 1N HCL. Pour this solution into a 500 ml bottle. Immediately before rinsing, place 1 vial of DNA rinse reagent into the bottle and mix the contents by swirling. This solution is stable for 2–3 hours.

Preparation of Calibration Slides:

To prepare the control cells, place two (2) CAS calibration slides (Elmhurst, Ill.; Catalog #102202–00) in 10% neutral buffered formalin for 30 minutes at room temperature. The calibration slides are touch-prep rat hepatocytes that have a known shape, size, and DNA amount. Next, rinse the CAS calibration slides in running deionized $H_2O$ for 5 minutes.

Preparation of Tissue Samples:

The 5 $\mu$m formalin fixed, paraffin embedded, tissue sections are first placed on Probe-On™ Plus microscope slides. Place the slides in Hemo-De for 1 minute at 45° C., and then drain the Hemo-De from the slides with the aid of absorbent paper. This step is repeated three (3) more times.

Next, place the specimen slides in absolute ethanol for 1 minute at room temperature, and then drain the alcohol from the slides with the aid of absorbent paper. Repeat this step one (1) more time.

Finally, place the specimen slides in PBS (pH 7.6) with 0.1% Triton X-100 for 10 seconds at room temperature, and then drain the PBS from the slides with the aid of absorbent paper. Repeat this step one (1) more time.

Feulgen Staining Procedure:

Place the slides (CAS calibration slides and specimen slides) in 5N HCL for 1 hour at room temperature. Next, place all of the slides in the Feulgen stain solution for 1 hour at room temperature (stir while staining). Drain the Feulgen stain solution and rinse the slides in the Feulgen rinse solution for 30 seconds at room temperature, followed by rinsing the slides in Feulgen rinse solution for 5 minutes at room temperature, followed by rinsing the slides in Feulgen rinse solution for 10 minutes at room temperature. The slides are then rinsed in running deionized $H_2O$ for 5 minutes. Destaining is done in 1 acid alcohol for 5 minutes at room temperature. This is followed by dipping the slides in 95% ethanol 10 times, followed by dipping the slides in absolute ethanol 10 times, followed by finally dipping the slides in xylene 10 times. Place a cover slip on the slides using a toluene or xylene based mounting media.

EXAMPLE II

Collection and Processing of CAS-200 CMP v3.0 Nuclear Morphometric Descriptors (40× Objective)

The morphometry data from the radical prostatectomy specimens is captured using the Cell Measurement Program v3.0 (CMP v3.0) software from a CAS-200 Image Analysis System. First, a study is set up in CMP v3.0 using the QDA Morphology Mode. The QDA Morphology Mode of CMP v3.0 allows the measurement of the Sum O.D., size, shape, cell class, and the 22 Markovian texture features (a step size of 1 was used in this invention) for each cell (see Table I), as well as the generation of a DNA histogram through the use of the QDA v3.0 software program on the CAS-200 Image Analysis System. Once the study is set up, the CMP v3.0 program (under the QDA Morphology Mode) activates the QDA v3.0 program, and the optical system is calibrated using the CAS calibration slides that were stained with the specimen slides. At least 20 calibration cells are measured, with a calibration peak percent coefficient of variation (% C.v.) of less than 2.0%. (NOTE: If the % C.V. is greater than 2.0%, a problem has occurred in the staining process.) Next, at least 125 cancer cells are analyzed using the method described in Example IV, and the cell nuclear images captured from each 5 μm Feulgen stained tissue section, with all of the sum O.D., size, shape, and Markovian texture measurements being saved to a CMP v3.0 vector (*.VEC) file. The nuclear cell images and DNA content information are saved to a QDA v3.0 listmode (*.ILM) file. The CMP vector file (*.VEC) is then converted to a Lotus 1-2-3 file (*.WK1) using the CMP Exporting Utility (a feature of the CMP v3.0 software). The DNA content information contained in the listmode file is extracted with specially written software and saved to a comma delimited text file. The Lotus 1-2-3 file (*.WK1) is then transferred to a 486 PC equipped with Windows v3.1 and Excel v5.0 for Windows, and an Excel v5.0 macro file is used to convert the Lotus 1-2-3 file (*.WK1) into separate Excel v5.0 files (*.XLS) for each case, each file containing the following information for every cell captured from that particular specimen: the sum O.D, size, shape, cell class, 22 Markovian texture features, and DNA content; (referred to collectively as CMP Nuclear Morphometric Descriptors, or CMP NMD's). Each Excel v5.0 file (*.XLS) also contains the means, standard deviations, variances, minima, and maxima for each CMP NMD. In addition, the macro creates a summary file containing the above statistics for each sMP NMD from every case.

EXAMPLE III

Collection and Processing of JVB ILM Morphometry v1.0 Nuclear Morphometric Descriptors The morphometry data from radical prostatectomy specimens is captured from the saved listmode files (*.ILM) using the JVB ILM Morphometry v1.0 software program, which allows the measurement and calculation of up to 36 different features. The listmode files (*.ILM) are created using the QDA v3.0 software from a CAS-200 Image Analysis System. The optical system is calibrated using the CAS calibration slides that were stained with the specimen slides by measuring at least 20 calibration cells, with a calibration peak percent coefficient of variation (% C.V.) of less than 2.0%. (NOTE: If the % C.V. is greater than 2.0%, a problem has occurred in the staining process.) Next, at least 125 cancer cells are analyzed using the method described in Example IV, and the cell nuclear images captured from each 5 μm Feulgen stained tissue section. The DNA content information and cell nuclear images are saved to a listmode (*.ILM) file. The listmode files (*.ILM) are then transferred to a 486 PC equipped with Windows v3.1 and Excel v5.0 for Windows, and converted using the JVB ILM Morphometry v1.0 program into 36 measurements (collectively referred to as JVB Nuclear Morphometric Descriptors, or JVB NMD's), which are contained in a Microsoft Access Database file (*.MDB). These 36 measurements include the sum O.D., size, shape, DNA content, 22 Markovian texture features, and nuclear shape features (see Table II). The Microsoft Access Database file (*.MDB) is then converted to an ASCII comma delimited file (*.CSV) using a conversion feature of the JVB ILM Morphometry v1.0 program. Finally, using Excel v5.0, an Excel v5.0 macro file is used to convert the ASCII comma delimited file (*.CSV) into separate Excel v5.0 files (*.XLS) for each case, each file containing the JVB NMD's for every cell captured from that particular specimen. Each Excel v5.0 file (*.XLS) also contains the means, standard deviations, variances, minima, and maxima for each JVB NMD. In addition, the macro creates a summary file containing the above statistics for each JVB NMD from every case.

EXAMPLE IV

Cancer Cell Selection Method

The inventors used a cell selection process for the radical prostatectomy specimens that seemed to introduce the least amount of bias and took into account the heterogeneity of prostate cancer tumors. The tumor area must first be identified by an expert pathologist. Once the tumor area(s) have been identified, a minimum of 25 image fields and a maximum of 5-6 cells per image field must then be analyzed and the cell nuclear images captured. The cells selected may not be overlapping, and they may not contain any "holes", which is the result of an improper background threshold setting. Sample the entire circled tumor area. The best way to do this is to mentally partition the circled tumor area into four separate quadrants, and then measure a minimum of 6-7 image fields per quadrant. In each quadrant, select image fields from the "worst" (e.g. Highest grade) cancer areas. (NOTE: The "worst" area in each quadrant may vary from low grade, well differentiated cancer to high grade, poorly differentiated cancer. Just be sure to measure from the "worst" area in each of the four quadrants.) Once you have collected the required number of cells, save the DNA information and nuclear images to a listmode file.

EXAMPLE V

Analysis of CAS-200 DNA Histograms

The DNA histograms were interpreted and classified by three different methods by the consensus of five individuals.

Figure 28A:
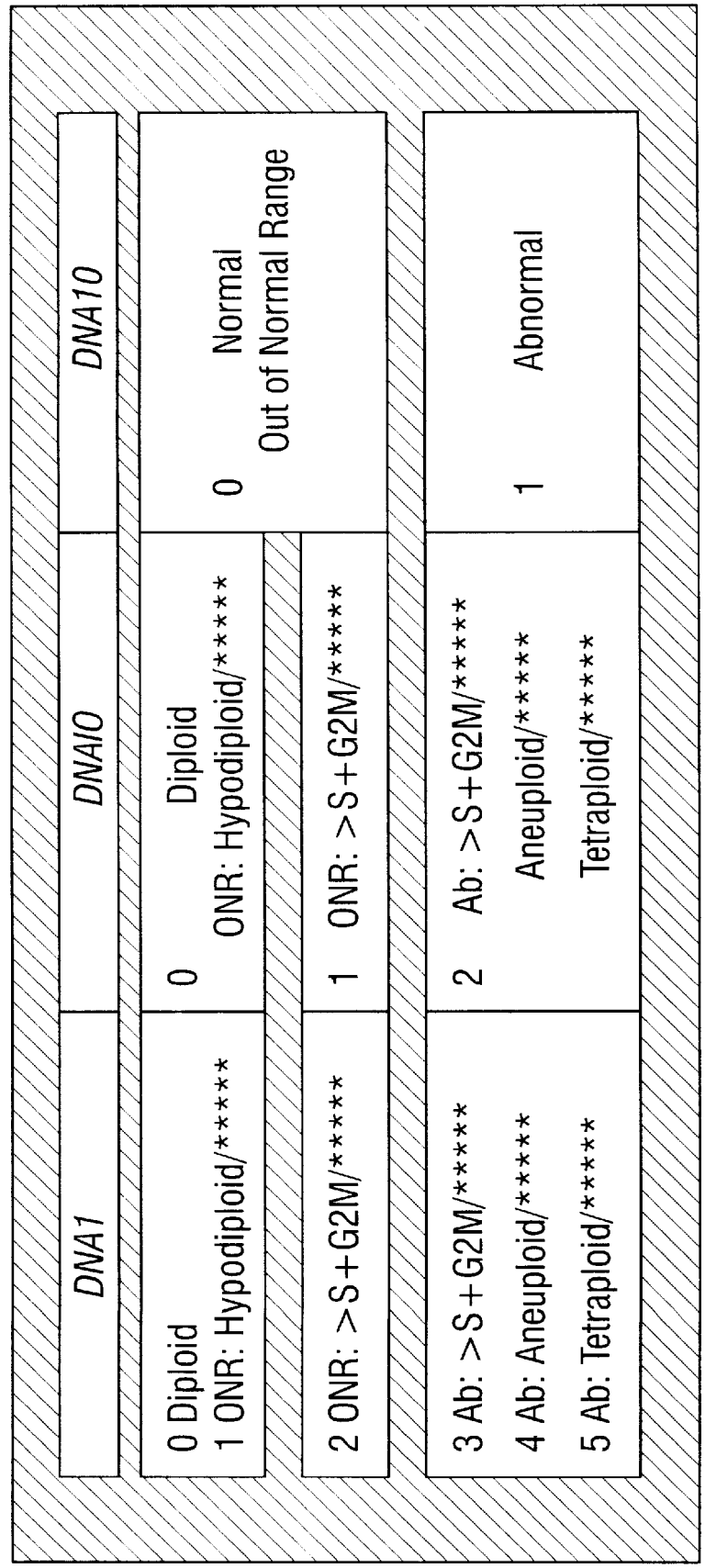
Figure 29:
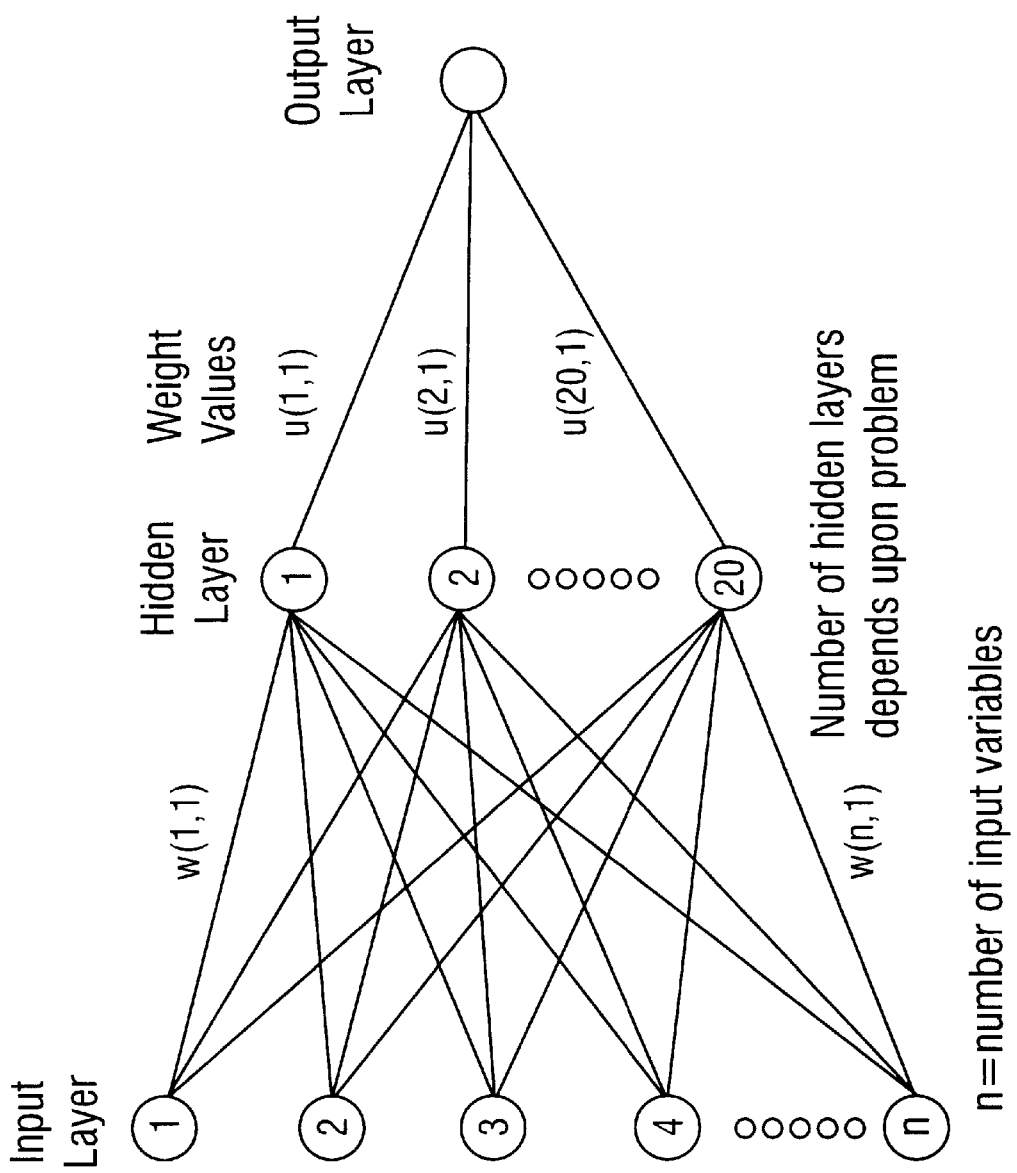
FIG. 29—Neural network configuration.

The three different methods employed cut-offs based upon the results of a DNA Consensus meeting held at Prautz Neck, ME in 1992 (Shankey, T. V. et al. Cytometry 14:497–500, 1993). The histograms were interpreted by four different individuals, and a consensus DNA ploidy classification agreed upon. The classification methods are as follows: (See FIG. 28A and FIG. 28B)

DNA-1=(0) Diploid; (1) ONR: Hypodiploid; (2) ONR: >S+G2M (11–21%); (3) Abnormal: >S+G2M ($\geq$21%); (4) Abnormal: Aneuploid; and (5) Abnormal: Tetraploid DNA-IO=(0) Diploid and ONR: Hypodiploid; (1) ONR: >S+G2M (11–21%); (2) Abnormal: >S+G2M (≧21%), Aneuploid, and Tetraploid DNA-10=(0) Normal and Out of Normal Range; (1) Abnormal The three different methods employed cut-offs determined by the inventors. The histograms were interpreted, and the classification methods are as follows:

JHHDNA=(0) Diploid; (1) Tetraploid; (2) Aneuploid

JHHDNA10=(0) Diploid; (1) Non-Diploid (i.e. Tetraploid and Aneuploid)

JHH%>2N=Percentages of S-Phase and Tetraploid fractions combined from ploidy determinations.

For statistical analysis, each classification scheme coded every subclass as a result for each patient (i.e. CDI DNA Ploidy: Diploid=0, Hypodiploid=1, ONR: >S+G2M=2, Tetraploid=5, Normal=0, Abnormal=1; JHH DNA Ploidy: Diploid=0, Tetraploid=1, Non-Diploid=1, etc.). The JHH%>2N classification method used the percentage as a result for each patient. These coded results were used for statistical analysis.

EXAMPLE VI

Nuclear Roundness Factor Measurement and Calculation of Variance

Definition of Nuclear Roundness Factor

The nuclear roundness factor represents a dimensionless, size-invariant shape descriptor that is based on the ratio of the calculated radius for the measured perimeter divided by the calculated radius for the measured area of the nucleus. This descriptor yields a low value of 1.00 for a perfect circle and increases as the shape of the nucleus deviates from circularity. In mathematical terms:

Perimeter $(P)=2\pi r_p$ and Area $(A)=\pi r_a^2$

Solve Equations for the Radius $(r_p)=(P)/(2\pi)$ and $(r_a)=\sqrt{A/\pi}$

Substitute Radius Equations into Nuclear Roundness Factor Equation

Nuclear Roundness Factor $(NRF)=r_p/r_a=((P))(2\pi))/(\sqrt{A/\pi})$

The variance in the nuclear roundness (NRV) was calculated using the following formula:

$$(NRV) \text{ Variance} = \sum_{j=1}^{j=n} (Y_j - Y)^2 / n$$

n=Number of cells measured
j=The $j^{th}$ cell
$Y_j$=The nuclear roundness factor of the $j^{th}$ cell
Y=The average or mean nuclear roundness factor for all of the cells Measurement of Nuclear Roundness using the DynaCELL™ System Histologic tissue sections (5–6 μm) were cut from re-embedded paraffin blocks of radical prostatectomy specimens. Multiple sections were cut (thirty sections per specimen), and one set of slides from each specimen were stained with Hematoxylin and Eosin (Sakura Diversified Stainer, Model DRS-601) and Feulgen stain (Cell Analysis Systems, Elmhurst, Ill.). The H&E staining procedure was performed on sections #1, 10, 20, and 30 for purposes of pathology review to confirm the presence of cancer for additional biomarker studies. All pathologic radical prostatectomy specimens were assigned Gleason scores (sum). The nuclear roundness factor measurements were performed using the H&E sections. A total of 150 cancerous nuclei from the primary tumor were analyzed with a Zeiss inverted IM microscope (Carl Zeiss, Inc., Thornwood, N.Y.) equipped with a Zeiss Planochromatic 100× oil emersion objective, giving a total magnification of 2440×. The nuclear images were digitized and analyzed with the DynaCELL™ Motility Morphometry Measurement workstation (JAW Associates, Inc., Annapolis, Md.). In this invention, the nuclear roundness variance measurement is the only calculation used from the DynaCELL™ Motility Morphometry Measurement software.

EXAMPLE VII

Utilization of Increased Magnification (63×) to Reduce the Number of NMD's Required to Predict Progression Using a subset of the original patient sample (10 progressors and 10 non-progressors), measurements were conducted as in Examples II & III, except that instead of using the normal 40× objective, a 63× objective lens was used. The data and statistics obtained using the 63× objective were analyzed and compared to the data and statistics obtained using the 40× objective. Table III summarizes the results of the statistical analysis using the 40× and 63× data to predict prostate cancer progression in the subset of 20 patients. Please note that the total number of NMD's required to predict an outcome is decreased as the magnification increases (Table III; also see FIGS. 3–6), as well as significant changes in the actual individual NMD's utilized in the model.

EXAMPLE VIII

Immunochemical Staining for Her-2/neu (c-erbB2)

Her-2-neu (c-erbB2) monoclonal antibody (Ab-3, OP-15) was provided by Oncogene Sciences Inc. (Uniondale, N.Y.) as a gift. The SuperSensitive MultiLink™ kit (BioGenex Inc., Ca.), which employs the strep-avidin biotin complex (ABC) alkaline phosphatase (AP) labelling method, was used for monoclonal antibody detection. All staining was performed with the MicroProbe™ manual staining system (Fisher Scientific, Pittsburgh, Pa.) that utilizes capillary action vertical staining principles. Incubation for the monoclonal antibody was 4° centigrade overnight. Briefly, the staining procedure includes first preparing the immunostaining reagents as follows:

Immunostaining Reagent Preparation

PBS pH 7.6 with 0.1% Triton X-100

Place 450 ml of Type I $H_2O$ into a 500 ml graduated cylinder. Then add one envelope of Coulter PBS Buffer Reagent (Coulter Source, Marietta, Ga.) to the type I water while stirring. Adjust the pH to 7.6 with approximately 20 drops of 1 N NaOH (a plastic transfer pipet is useful in adding the NaOH). Pipette 500 μl of Triton X-100 to the solution. Next, Adjust the volume of the solution to 500 ml with Type I $H_2O$.

PBS pH 7.6 with 0.5% Triton X-100

Place 450 ml of Type I $H_2O$ into a 500 ml graduated cylinder. Then add one envelope of Coulter PBS Buffer Reagent to the type I water while stirring. Adjust the pH to 7.6 with approximately 20 drops of 1 N NaOH (a plastic transfer pipet is useful in adding the NaOH). Pipette 2.5 ml of Triton X-100 to the solution. Adjust the volume of the solution to 500 ml with Type I H₂O.

1M Levamisole Stock Solution

Measure 241 mg (0.241 g) of levamisole (Sigma) using an analytic balance. Place the levamisole into a 1.5 ml microcentrifuge tube containing 1 ml of Type I H₂O. Mix the contents with the aid of a vortex mixer. Store the solution at 4° C. until it is used.

5% Nonfat dry milk with PBS pH 7.6 0.1% Triton X-100, 0.05% thimerosal

Place 5 grams of nonfat dry milk in a Erlenmeyer flask containing 100 ml PBS pH 7.6 with 0.1% Triton® X-100. Then, add 0.05 g of thimerosal and mix the solution by stirring. Store 5 ml aliquots of the solution at −80° C. Upon thawing, the solution should be stored at 4° C. Do not use this solution if it has been stored at 4° C. for longer than 5 days.

0.5% Nonfat dry milk with PBS pH 7.6 0.1% Triton X-100

Pipette 100 µl 5.0% nonfat dry milk with PBS pH 7.6 0.1% Triton X-100, 0.05% thimerosal into a 1.5 ml microcentrifuge tube or 10 ml test tube containing 900 µl of PBS pH 7.6 with 0.1% Triton X-100. Mix the solution with the aid of a vortex. The solution should be stored at 4° C. Do not use this solution if it has been stored at 4° C. for longer than 5 days.

C-Neu, Her-2/Neu (1:40)

Pipette 875 µl of PBS pH 7.6 with 0.1% Triton X-100 into a 1.5 ml microcentrifuge tube or 10 ml test tube. Pipette 100 µl 5.0% nonfat dry milk with PBS pH 7.6 with 0.1% Triton X-100 to the tube and mix the solution with the aid of a vortex. Then, pipette 25 µl of C-Neu (ab-3) to the tube and mix with the aid of a vortex. The antibody should be added last to the solution.

Normal Mouse Serum Control (1:1000)

Pipette 899 µl of PBS pH 7.6 with 0.1% Triton X-100 into a 1.5 ml microcentrifuge tube or 10 ml test tube. Pipette 100 µl 5.0% nonfat dry milk with PBS ph 7.6 with 0.1% Triton X-100 to the tube and mix the solution with the aid of a vortex. Pipette 1 µl Normal Mouse Serum (Dako) to the solution and mix with the vortex. The normal mouse serum should be added last to the solution.

Mouse IgG1 Isotypic Control (1:200)

Pipette 895 µl of PBS pH 7.6 with 0.1% Triton X-100 into a 1.5 ml microcentrifuge tube or 10 ml test tube. Pipette 100 µl 5.0% nonfat dry milk with PBS ph 7.6 with 0.1% Triton X-100 to the tube and mix the solution with the aid of a vortex. Pipette 5 µl Mouse IgG1 Isotypic Control (Coulter) to the solution and mix with the vortex. The Mouse IgG1 Isotypic Control should be added last to the solution.

2°Ab (Biotinylated anti-mouse IgG, Multilink)

Comes premixed in the BioGenex Large Volume Multi-Link Kit

Label (Streptavidin/Alkaline Phosphatase)

Comes premixed in the BioGenex Large Volume Multi-Link Kit

Fast Red Chromogen Solution

Pipette 5 µl of 1.0 M Levamisole to the 5 ml vial of Naphthol Phosphate in Tris Buffer. Add one Fast Red Tablet to the solution and vortex until the tablet is completely dissolved. This solution must be used immediately after preparation. *Levamisole is added to the Fast Red Solution to block endogenous alkaline phosphatase activity.

The Her-2/neu antigenicity was then scored. The scoring method assessed the amount of staining area within the "dotted cancer zone" as either negative (0), focal (1), or diffuse (2), and the intensity of the staining was scored as 0–4+, ranging from negative (0) to strong red color (4+) resulting from the AP red substrate reaction (see FIG. 28A and FIG. 28B).

EXAMPLE IX

Immunochemical Staining for PD-41

The PD-41 (Prostate Mucin Antigen) monoclonal antibody was provided by Dr. George Wright at Eastern Virginia Medical School under a materials transfer agreement. The SuperSensitive MultiLink™ kit (BioGenex Inc., Ca.), which employs the strep-avidin biotin complex (ABC) alkaline phosphatase (AP) labelling method, was used for monoclonal antibody detection. All staining was performed with the MicroProbe™ manual staining system (Fisher Scientific, Pittsburgh, Pa.) that utilizes capillary action vertical staining principles. Incubation for the monoclonal antibody was 370 centigrade for 15 minutes. Briefly, the staining procedure includes first preparing the immunostaining reagents as in Example X, except with the following changes:

Immunostaining Reagent Preparation

PD-41 (15 µg/ml)

Place 800 µl of PBS pH 7.6 with 0.1% Triton X-100 in a 1.5 ml microcentrifuge tube. Add 100 µl 50 milk to the tube and mix the contents with the aid of a vortex mixer. Then, add 100 µl of PD-41 to the tube and mix the contents with the aid of a vortex mixer.

CAS Red Chromogen Solution

Add 900 µl of Type I H₂O to a 1.5 ml microcentrifuge tube. Add the 1 µl of 1 M levamisole to the tube. Then, add 100 µl of CAS red substrate concentrate and mix the contents with the aid of a vortex mixer. Add 45 µl of CAS red chromogen concentrate (always add this ingredient last) to the solution and mix the contents with the aid of a vortex mixer. This solution must be used immediately after preparation.

The PD-41 antigenicity was then scored. The scoring method employed the number of positive staining ducts divided by the total number of ducts in the "dotted cancerous zone". The percentages of positively staining ducts was used as a patient result.

PD-41 Background

Monoclonal antibody PD-41, a mouse $IgG_{1k}$, was first described by Beckett et al. (Beckett, ML, Lipford, GB, Haley, Cl, Schellhammer, PF and Wright, GL. Monoclonal Antibody PD41 Recognizes an Antigen Restricted to Prostate Adenocarcinomas. Cancer Res. 51:1326–1333, 1991) by its reactivity to an prostate adenocarcinoma-restricted mucoprotein known as prostate mucin antigen (PMA). The target PMA, an O-linked oligosaccharide-associated protein with a molecular weight of >400 kd in prostate cancer patient seminal plasma, has not been demonstrated to recognize mucins at other organ sites. Wright et al. (Wright, GL, Beckett, ML et al. Mucins as biomarkers of prostate carcinoma. J. Urol. 149:450A, 1993) demonstrated immunoperoxidase immunoreactivity of PD-41 with in 100% of primary, 71% of metastatic carcinomas and under 1% of normal and benign prostatic tissues, including BPH.

An independent study of 95 prostate needle core biopsy paraffin-embedded sections showed PD-41 reactivity in ductal epithelia and/or prostatic glandular secretions within 56% (53/95) of prostate tumor specimens (Marley, GM, Veltri, RW, Patton, KP and Wright, GL. Histochemical Expression of a Unique Prostate Mucin Antigen from Core Biopsies. Proc. Amer. Assoc. Cancer Res. 34:28, 1993). When Gleason score or DNA ploidy were employed as stratification parameters, PD-41 proved to be an independent factor of prognostic value. Clinical follow-ups of 61% of this cohort confirmed that PD-41 expression acted as an independent marker of tumor aggressiveness (Veltri, RW et al., recent CDI unpublished data).

EXAMPLE X

The Patient Sample

A group of one hundred and twenty-four (124) patients with localized prostate cancer were used in this study. The sample was optimized for the evaluation of tumor progression. The patients had clinically localized prostate cancer and were followed for evidence of progression based upon one or more of the following events: a detectable post-operative prostate specific antigen (PSA) level, local recurrence, evidence of metastasis following radical prostatectomy, or death. The patient sample had been clearly defined for pre-operative Gleason grades, post-operative Gleason grades, clinical and pathological stage, organ disease confinement, focal or established capsular penetration, and surgical margin status. None of these patients had any seminal vesicle or lymph node invasion. The demographics of the patient sample is illustrated in Table IV.

EXAMPLE XI

Statistical Analysis—Logistic Regression

The logistic regression statistical analysis of the data was performed using the STATA™ v3.1 (Stata Corporation, College Station, Tex.) statistical analysis software program. This invention applied logistic regression to every independent parameter (e.g. NMD's, biomarkers, NRV, Gleason scores, etc.) first to select the univariately significant variables for progression or organ confined disease status (Table V & VIII) using the STATA™ statistical software package (STATA™ command: logistic). Statistical significance consisted of p values $\leq 0.05$. Next, the univariately significant independent variables were multivariately assessed using backwards stepwise logistic regression (STATA™ command: swlogis) to determine which independent variables (e.g. NMD's (CMP or JVB), Gleason Score, Nuclear Roundness Variance, and biomarkers) were aggregately significant in the prediction of progression or organ confined disease status (Tables VI, VIa, VII, VIIa, IX, IXa, X, & Xa). The software program generated Receiver Operator Characteristic (ROC) curves with investigator selected cutoff, resulting in optimized sensitivity, specificity, positive predictive values, and negative predictive values (see above listed tables and FIGS. 7–27). Kaplan-Meier actuary plots were also generated for the progression analysis.

STATA™ also provides a command (logit, an estimated maximum-likelihood logit model) that provides the weighted coefficients for the statistically significant independent variables used in the multivariate model as well as the model constant. The general formulas for calculating the predictive index and predictive probability are as follows:

Predictive Index $(xb) = (\beta_0 + \beta_1 var(1) + \beta_2 var(2) + \text{ - - - } + \beta_n var(n))$ Predictive Probability $(p) = e^{xb}/(1+e^{xb})$ Where:
$\beta_0$=Formula Constant;
$\beta_1$ through $\beta_n$=Weight factors for variables 1 through n;
var(1) through var(n)=Independent variables being used in logistic regression model.

The final calculation of the predictive probability provides a patient-specific value, between 0 and 1, for the probability of a specific outcome (e.g. progression or organ confined disease status). The threshold value (cutoff) for the predicted probability is selected based upon the results of the ROC curves. Equation 2 gives an example using the weighted formula.

Equation 2:

Formula for Progression Predicted Probability of JVB Morphometry Features Alone

Predictive Index:

$$\begin{aligned}
\text{Morphometry } x_j b = & (-61.2378) + (-0.7827881)(stdev1) + \\
& (3.209138)(stdev2) + (13.90239)(stdev4) + \\
& (-1381.354)(stdev7) + (11.52351)(stdev8) + \\
& (-1.18553)(stdev10) + (-0.603529)(stdev11) + \\
& (0.6900095)(stdev14) + (1254.563)(stdev15) + \\
& (2964.96)(stdev17) + (2.370112)(stdev24) + \\
& (505.4493)(stdev26) + (-7.731191)(stdev28) + \\
& (84.19147)(stdev31) + (-28.88644)(stdev34) + \\
& (0.01796)(var1) + (-0.0390615)(var2) + \\
& (7.529075)(var3) + (-45.39564)(var4) + \\
& (12174.49)(var7) + (-18176.55)(var15) + \\
& (-26895.28)(var17) + (-2.079085)(var22) + \\
& (1.093606)(var28) + (2180.479)(var29) + \\
& (1.959982)(var34) + (-7.559859)(var35)
\end{aligned}$$

Predictive Probability:

Morphometry $P_j = \exp(x_j b)/(1+\exp(x_j b))$, where
- $x_j$=The (row) vector of independent variables of the $j^{th}$ observation, (i.e., the independent variable value).
- b=The corresponding estimated parameter (column) vector, (i.e., the weight factor associated with that particular independent variable).
- $P_j$=Predicted probability of a positive outcome for the $j^{th}$ observation.

EXAMPLE XII

Application of Neural Networks

The multilayer feed forward perceptron with error back propagation training method is chosen for this work. The back propagation method is a gradient based learning procedure, but has the drawback of local optimum. Studies show sigmoid activation function, which is often used with neural network, is not necessarily the optimal choice. It has been suggested in certain classes of problems that the use of sinusoidal or gaussian activation functions reduce the training time substantially. In this work, both sigmoid and sinusoidal activation functions are studied.

In a multilayer neural network, hidden layers are of particular importance. How well the network approximates the discriminate surface to a large degree depends on the number of hidden neurons. Allowing too few or too many parameters to be used in the training will lead to under or over fitting. Therefore, efforts have been made to identify the optimal number of hidden neurons.

The neural network (NN) software program of the present invention has a single hidden layer. Morphometry data from the radical prostatectomy samples was analyzed, and a total of 28 NMD's were extracted. Backwards stepwise logistic regression analysis of the data utilizing the STATA™ software showed that only 14 of the NMD's were multivariately significant. (NOTE: The 30 feature network used all 28 NMD's, post operative Gleason score, as well as the perimeter and nuclear roundness variance calculated using the CAS-200). Using the data sets of 15, 28, and 30 measurements, two different network types were trained, a standard multilayer sigmoidal type with a single hidden layer, and a hybrid network previously described. Further utilization of the data used for training these networks within the scope of the invention will result in networks with greater accuracy.

All of the methods disclosed and claimed herein can be made and executed with undue experimentation in light of the present disclosure. While the methods of this invention have been described in terms of preferred embodiments, it will be apparent to those of skill in the art that variations may be applied to the methods, and in the steps or in the sequence of steps of the method described herein without departing from the concept, spirit, and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope, and concept of the invention as defined by the appended claims.

The following is the Microsoft Excel v5.0 source code for the macro program used to convert the CMP v3.0 vector files as set forth in Example II.

CMP Macro Source Code

```
'CMP Macro
'Macro recorded 6/16/94 by Craig Miller
'
'Keyboard Shortcut: Ctrl+c
'
Sub CMP()
    MsgBox "To run this macro, you must first convert the listmode files using the CDI.BP IMPORT.40X program in CORTEX. If you have not done this, please select the file named END.XLS"
OpenLine:
    MsgBox "Open the *.WK1 Vector file which you wish to separate, or end the macro by selecting the END.WK1 file"
    ChDrive "F"
    ChDir "F:\USERS\MCM\40X"
    OpenFile = Application.GetOpenFilename("Lotus 1-2-3 (*.wk1), *.wk1")
    Workbooks.Open Filename:=OpenFile
    FileLength = Len(OpenFile)
    SearchStr = "X "
    Period = InStr(OpenFile, SearchStr)
    OpenFile1 = Mid(OpenFile, Period + 2)
    FileLength1 = Len(OpenFile1)
    SearchStr1 = "."
    Period1 = Instr(OpenFile1, SearchStr1)
    OpenFile2 = Left(OpenFile1, Period1 - 1)
    CASENUM = Range("A2").Value
'If there are no values in the file, end the macro. If data is present, proceed
    If CASENUM = Then GoTo LastLine Else GoTo FormatLine
FormatLine:
    Application.ScreenUpdating = False
    Cells.Select
    With Selection
        .HorizontalAlignment = xlCenter
        .VerticalAlignment = xlBottom
        .WrapText = False
        .Orientation = xlHorizontal
    End With
    With Selection.Font
        .Name = "Times New Roman"
        .FontStyle = "Regular"
        .Size = 10
        .Strikethrough = False
        .Superscript = False
        .Subscript = False
        .OutlineFont = False
        .Shadow = False
        .Underline = xlNone
        .ColorIndex = xlAutomatic
    End With
    Columns("B:C").Select
    Selection.Delete Shift:=xlToLeft
    Columns("E:G").Select
    Selection.Insert Shift:=xlToRight
    Columns("A:AE").Select
    Selection.Cut
    Workbooks.Open Filename:="C:\CRAIG\MACROS\WK1CNVRT.BLK"
    ActiveSheet.Paste
```

| CMP Macro Source Code |
|---|

```
Range("B:D,H:AD").Select
Selection.NumberFormat = "0.000000"
Range("E:G").Select
Selection.NumberFormat = "0.00"
Columns ("A:AE").Select
Selection.EntireColumn.AutoFit
With Selection.Borders(xlLeft)
   .Weight = xlThin
   .ColorIndex = xlAutomatic
End With
With Selection.Borders (xlRight)
   .Weight = xlThin
   .ColorIndex = xlAutomatic
End With
With Selection.Borders (xlTop)
   .Weight = xlThin
   .ColorIndex = xlAutomatic
End With
With Selection.Borders (xlBottom)
   .Weight = xlThin.
   .ColorIndex = xlAutomatic
End With
Selection.BorderAround LineStyle:=xlNone
Range ("A2").Select
Application.ScreenUpdating = True
ChDrive "F"
ChDir "F:\USERS\MCM\40X\CMP"
   With ActiveWorkbook
      .Title = ""
      .Subject = ""
      .Author = "Craig Miller"
      .Keywords = ""
      .Comments = ""
   End With
ActiveWorkbook.SaveAs Filename:=OpenFile2, FileFormat:=xlNormal, _
   Password:="", WriteResPassword:="", ReadOnlyRecommended.= _
   False, CreateBackup:=False
Application.ScreenUpdating = False
CASENUM = Range("A2").Value
While CASENUM <> ""
'Select all cells pertaining to this particular case
   Application.ScreenUpdating = False
   y = 3
      While Cells(y, 1) = CASENUM
         y = y + 1
      Wend
'Select the cells for one case, copy them to a blank CMP template, _
   and delete the first and last row (blank rows from template).
      Range(Cells(2, 1), Cells(y - 1, 31)).Select
      Selection.Copy
      Workbooks.Open Filename: = "C:\CRAIG\MACROS\CASCMP.BLK"
      Selection.Insert Shift:=xlDown
      Rows("3:3").Select
      Application.CutCopyMode = False
      Selection.Delete Shift:= xlUp
      y = 3
         While Cells(y, 1) = CASENUM
            y = y + 1
         Wend
      Range (Cells (y, 1), Cells (y, 31)).Select
      Selection.Delete Shift:= xlUp
'Make the first column the cell number
      Range ("A1").Select
      ActiveCell.FormulaR1C1 = "Cell"
      Range ("A3").Select
      ActiveCell.FormulaR1C1 = "1"
      Range ("A4").Select
      ActiveCell.FormulaR1C1 = "2"
      Set Source = Range(Cells(3, 1), Cells(4, 1))
      Set FILL = Range(Cells(3, 1), Cells(y - 1, 1))
      Source.AutoFill destination:=FILL
'Sort all of the cells according to first the Area and second the Shape
   Set CELLDATA = Range(Cells(3, 1), Cells(y - 1, 31))
      CELLDATA.Sort Key1:=Range ("C3"), Order1:=xlAscending, Key2:=Range _
         ("D3"), Order2:=xlAscending, Header:=xlGuess, OrderCustom:=1, _
         MatchCase:=False, Orientation:=xlTopToBottom
      Columns("E:E").Select
```

-continued

CMP Macro Source Code

```
    Selection.Delete Shift:=xlToLeft
'Select the position where the DNA and perimeter information will be _
  pasted, and open the DNA file created in CORTEX having the same name
  as the *.ILM file.
    Range.("E3").Select
    CASENUM = Trim(CASENUM)
    ChDrive "F"
    ChDir "F:\USERS\MCM\PFS"
    Workbooks.OpenText Filename:=CASENUM, Origin: = _
      xlWindows, StartRow:=2, DataType:=xlDelimited, TextQualifier _
      :=xlDoubleQuote, ConsecutiveDelimiter:=False, Tab:=False, _
      Semicolon:=False, Comma:=True, Space:=False, Other:=False, _
      FieldInfo:=Array(Array(1, 1), Array(2, 1), Array(3, 1), Array(4, 1))
'Determine the number of cells present and calculate the perimeter for
  each cell
    I = 1
      While Cells(I, 1) > 0
        I = I + 1
      Wend
    Set Source = Cells(1, 5)
    Set FILL = Range(Cells(1, 5), Cells(I - 1, 5))
    Range("E1").Select
    ActiveCell.FormulaR1C1 = "=SQRT(RC[-4] *RC[-3])"
    Source.AutoFill destination:=FILL
    Range(Cells(1, 5), Cells(I - 1, 5)).Select
    Selection.Copy
    Selection.PasteSpecial Paste:=xlValues1 Operation:=xlNone, _
      SkipBlanks:=False, Transpose:=False
    Application.CutCopyMode = False
'Sort the cells according to first the Area and second the Shape
    Rows ("1:1").Select
    Selection.Sort Key1:=Range ("A1"), Order1:=xlAscending, Key2:=Range _
      ("B1"), Order2:=xlAscending, Header:=xlGuess, OrderCustom:=1, _
      MatchCase:=False, Orientation:=xlTopToBottom
'Copy and paste the DNA and Perimeter data to the full database and _
  format the selection
    Range(Cells(1, 4), Cells(I - 1, 5)).Select
    Selection.Copy
    Windows ("CASCMP.BLK").Activate
    ActiveSheet.Paste
    Application.CutCopyMode = False
    With Selection.Font
      .Name = "Times New Roman"
      .Fontstyle = "Regular"
      .Size = 10
      .Strikethrough = False
      .Superscript = False
      .Subscript = False
      .OutlineFont = False
      .Shadow = False
      .Underline = xlNone
      .ColorIndex = xlAutomatic
    End With
    With Selection
      .HorizontalAlignment = xlCenter
      .VerticalAlignment = xlBottom
      .WrapText = False
      .Orientation = xlHorizontal
    End With
    With Selection.Borders (xlLeft)
      .Weight = xlThin
      .ColorIndex = xlAutomatic
    End With
    With Selection.Borders (xlRight)
      .Weight = xlThin
      .ColorIndex = xlAutomatic
    End With
    With Selection.Borders (xlTop)
      .Weight = xlThin
      .ColorIndex = xlAutomatic
    End With
    With Selection.Borders (xlBottom)
      .Weight = xlThin
      .ColorIndex = xlAutomatic
    End With
    Selection.BorderAround LineStyle:=xlNone
'Enter the column headings for the DNA and Perimeter columns
```

-continued

| CMP Macro Source Code |
|---|

```
    Range ("E1").Select
    ActiveCell.FormulaR1C1 = "Pg"
    Range("E2").Select
    ActiveCell.FormulaR1C1 = "DNA"
    Range ("F1").Select
    ActiveCell.FormulaR1C1 = "CAS"
    Range ("F2").Select
    ActiveCell.FormulaR1C1 = "Perimeter"
    Application.Goto Reference:="Stats"
    Selection.Copy
    Selection.PasteSpecial Paste:=xlValues, Operation:=xlNone, _
    SkipBlanks:=False, Transpose:=False
    Application.CutCopyMode = False
    Columns ("F:F").Select
    Selection.Cut
    Columns ("AE:AE").Select
    Selection.Insert Shift:=xlToRight
    Selection.NumberFormat = "0.000000"
    Range(Cells(3, 5), Cells(y – 1, 5)).Select
    Selection.NumberFormat = "0.00"
    Sheets("CMP Blank").Select
    Sheets("CMP Blank").Name = CASENUM
'Sort the cell data according to the Cell Number and save the workbook _
    with the same filename as the *.ILM file
    Set CELLDATA = Range(Cells(3, 1), Cells(y – 1, 30))
    CELLDATA.Sort Keyl:=Range ("A3"), Orderl:=xlAscending, Header:=xlGuess, _
        OrderCustom:=1, MatchCase:=False, Orientation:=xlTopToBottom
    Cells(1, 1).Select
    With ActiveWorkbook
        .Title = ""
        .Subject = ""
        .Author = "Craig Miller"
        Keywords = ""
        .Comments = ""
    End With
    ChDir "F:\USERS\MCM\40X\CMP"
    ActiveWorkbook.SaveAs Filename:=CASENUM, FileFormat:=xlNormal _
        , Password:="", WriteResPassword:="", ReadOnlyRecommended:= _
        False, CreateBackup:=False
'Select the Statistical Calculations, paste them to a blank spreadsheet, _
    and cut and copy all of the values to a single row.
    Range(Cells(y + 2, 1), Cells(y + 6, 30)).Select
    Selection.Cut
    Workbooks.Add Template:="Workbook"
    ActiveSheet.Paste
    Range("A").Formula = CASENUM
    Range ("B2:AD2").Select
    Selection.Cut
    Range ("AE1").Select
    ActiveSheet.Paste
    Range ("B3:AD3").Select
    Selection.Cut
    Range ("BH1").Select
    ActiveSheet.Paste
    Range ("B4:AD4").Select
    Selection.Cut
    Range ("CK1").Select
    ActiveSheet.Paste
    Range ("B5:AD5").Select
    Selection.Cut
    Range ("DN1").Select
    ActiveSheet.Paste
    Rows ("1:1").Select
    Selection.Copy
'Paste the statistics for the case into the summary file
    Workbooks.Open Filename:="F:\USERS\MCM\40X\SUM-OD.CMP"
    Selection.Insert Shift:=xlDown
    Application.CutCopyMode = False
    ActiveWorkbook.Save
    ActiveWindow.Close
    ActiveWorkbook Saved = True
    ActiveWindow.Close
    ActiveWorkbook.Saved = True
    ActiveWindow.Close
    ActiveWorkbook.Saved = True
    ActiveWindow.Close
    Selection.Delete Shift:=xlUp
```

-continued

| CMP Macro Source Code |
|---|

```
    Range ("A2").Select
    Application.ScreenUpdating = True
'Continue looping the macro until all of the cases contained in this vector _
    file have been separated and no data is left in the vector file.
    CASENUM = Range("A2").Value
    Wend
'If there is more than one vector file the separate, open the next file
    ActiveWorkbook.Saved = True
    ActiveWindow.Close
    ActiveWorkbook.Saved = True
    ActiveWindow.Close
    GoTo OpenLine
'End the macro and refresh the screen
LastLine:
    ActiveWorkbook.Saved = True
    ActiveWindow.Close
    Application.ScreenUpdating = True
End Sub
```

The following is a flowchart and the source code listing of a computer program for the DNA content information import as set forth in Example II.

Import.40X Flow Diagram
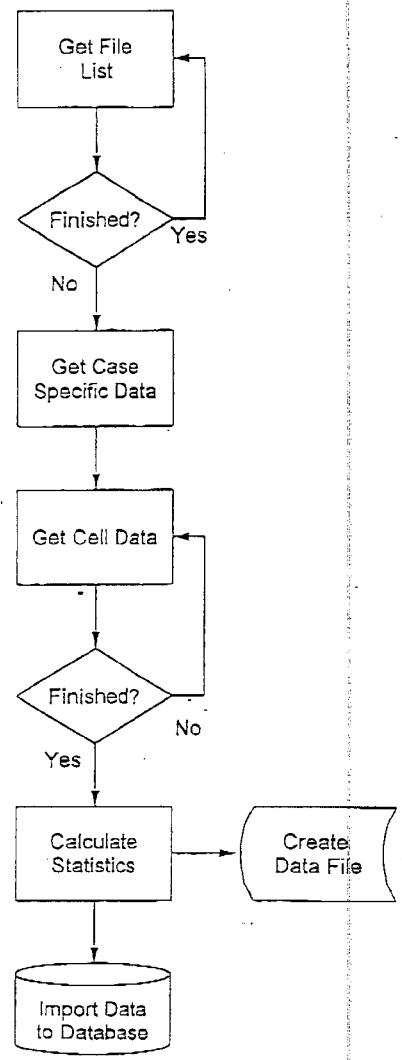

The following is the Microsoft Excel v5.0 source code for the macro program used to convert the JVB v1.0 database files as set forth in Example III.

VB Macro Source Code

```
'
' JVB Macro
' Macro recorded 6/24/94 by Craig Miller
'
' Keyboard Shortcut: Ctrl+j
'
Sub JVB()
OpenLine:
    MsgBox "Open the ILM Morphometry *.CSV file which you wish to separate, or end the macro by selecting the END.CSV file"
    ChDrive "C"
    ChDir "C:\IMAGING.JVB\FILES\STUDY.ILM"
    OpenFile = Application.GetOpenFilename("Text (*.csv), *.csv")
    Workbooks.Open Filename:=OpenFile
    FileLength = Len(OpenFile)
    SearchStr = "M\"
    Period = InStr(OpenFile, SearchStr)
    OpenFile1 = Mid(OpenFile, Period + 2)
    FileLength1 = Len(OpenFile1)
    SearchStr1 = "."
    Period1 = InStr(OpenFile1, SearchStr1)
    OpenFile2 = Left(OpenFile1, Period1 - 1)
    CASENUM = Range("B2").Value
' If there are no values in the file, end the macro. If data is present, proceed
    If CASENUM = "" Then GoTo LastLine Else GoTo FormatLine
FormatLine:
    Application.ScreenUpdating = False
    Cells.Select
    With Selection
        .HorizontalAlignment = xlCenter
        .VerticalAlignment = xlBottom
        .WrapText = False
        .Orientation = xlHorizontal
    End With
    Columns("A:A").Select
    Selection.Delete Shift:=xlToLeft
    Columns("I:I").Select
    Selection.Cut
    Columns("B:B").Select
    Selection.Insert Shift:=xlToRight
    Columns("D:D").Select
    Selection.Cut
    Columns("AL:AL").Select
    Selection.Insert Shift:=xlToRight
    Columns("F:N").Select
    Selection.Cut
    Columns("AL:AL").Select
    Selection.Insert Shift:=xlToRight
    Columns("AH:AH").Select
    Selection.Cut
    Columns("AB:AB").Select
    Selection.Insert Shift:=xlToRight
    Columns("A:A").Select
    Selection.NumberFormat = "@"
    Columns("B:AK").Select
    Selection.NumberFormat = "0.000000"
    Selection.EntireColumn.AutoFit
    Columns("E:E").NumberFormat = "0.00"
    Columns("AB:AB").NumberFormat = "0"
    Columns("AD:AD").NumberFormat = "0.00"
    Columns("AE:AE").NumberFormat = "0.00"
    Range("A2").Select
    Application.ScreenUpdating = True
    ChDrive "F"
    ChDir "F:\USERS\MCM\40X"
        With ActiveWorkbook
            .Title = ""
            .Subject = ""
            .Author = "Craig Miller"
            .Keywords = ""
```

-95-

'VB Macro Source Code

```
            .Comments = ""
        End With
    ActiveWorkbook.SaveAs Filename:=OpenFile2, FileFormat:=xlNormal, _
        Password:="", WriteResPassword:="", ReadOnlyRecommended:= _
        False, CreateBackup:=False
    Application.ScreenUpdating = False
    CASENUM = Range("A2").Value
    While CASENUM <> ""
        Application.ScreenUpdating = False
' Select all cells pertaining to this particular case
        y = 3
        While Cells(y, 1) = CASENUM
            y = y + 1
        Wend
' Select the cells for one case, copy them to a blank JVB template, _
    and delete the first and last row (blank rows from template).
        Range(Cells(2, 1), Cells(y - 1, 37)).Select
        Selection.Copy
        Workbooks.Open Filename:="C:\CRAIG\MACROS\JVBCMP.BLK"
        Selection.Insert Shift:=xlDown
            With Selection.Font
                .Name = "Times New Roman"
                .FontStyle = "Regular"
                .Size = 10
                .Strikethrough = False
                .Superscript = False
                .Subscript = False
                .OutlineFont = False
                .Shadow = False
                .Underline = xlNone
                .ColorIndex = xlAutomatic
            End With
            With Selection
                .HorizontalAlignment = xlCenter
                .VerticalAlignment = xlBottom
                .WrapText = False
                .Orientation = xlHorizontal
            End With
            With Selection.Borders(xlLeft)
                .Weight = xlThin
                .ColorIndex = xlAutomatic
            End With
            With Selection.Borders(xlRight)
                .Weight = xlThin
                .ColorIndex = xlAutomatic
            End With
            With Selection.Borders(xlTop)
                .Weight = xlThin
                .ColorIndex = xlAutomatic
            End With
            With Selection.Borders(xlBottom)
                .Weight = xlThin
                .ColorIndex = xlAutomatic
            End With
        Selection.BorderAround LineStyle:=xlNone
        Columns("A:AK").EntireColumn.AutoFit
        Rows("3:3").Select
        Application.CutCopyMode = False
        Selection.Delete Shift:=xlUp
        y = 3
        While Cells(y, 1) = CASENUM
            y = y + 1
        Wend
        Range(Cells(y, 1), Cells(y, 37)).Select
        Selection.Delete Shift:=xlUp
' Make the first column the cell number
        Range("A1").Select
        ActiveCell.FormulaR1C1 = "Cell"
        Range("A3").Select
        ActiveCell.FormulaR1C1 = "1"
```

-96-

'VB Macro Source Code

```
        Range("A4").Select
        ActiveCell.FormulaR1C1 = "2"
            Set Source = Range(Cells(3, 1), Cells(4, 1))
            Set FILL = Range(Cells(3, 1), Cells(y - 1, 1))
        Source.AutoFill destination:=FILL
        Sheets("JVBCMP").Select
        CASENUM = Trim(CASENUM)
        Sheets("JVBCMP").Name = CASENUM
        Range("A1").Select
        ChDir "F:\USERS\MCM\40X"
            With ActiveWorkbook
                .Title = ""
                .Subject = ""
                .Author = "Craig Miller"
                .Keywords = ""
                .Comments = ""
            End With
        ActiveWorkbook.SaveAs Filename:=CASENUM, FileFormat:=xlNormal, _
            Password:="", WriteResPassword:="", ReadOnlyRecommended:= _
            False, CreateBackup:=False
' Select the Statistical Calculations, paste them to a blank spreadsheet, _
    and cut and copy all of the values to a single row.
        Range(Cells(y + 2, 1), Cells(y + 6, 37)).Select
        Selection.Copy
        Selection.PasteSpecial Paste:=xlValues, Operation:=xlNone, _
        SkipBlanks:=False, Transpose:=False
        Selection.Cut
        Workbooks.Add Template:="Workbook"
        ActiveSheet.Paste
        Range("A1").Formula = CASENUM
        Range("B2:AK2").Select
        Selection.Cut
        Range("AL1").Select
        ActiveSheet.Paste
        Range("B3:AK3").Select
        Selection.Cut
        Range("BV1").Select
        ActiveSheet.Paste
        Range("B4:AK4").Select
        Selection.Cut
        Range("DF1").Select
        ActiveSheet.Paste
        Range("B5:AK5").Select
        Selection.Cut
        Range("EP1").Select
        ActiveSheet.Paste
        Rows("1:1").Select
        Selection.Copy
' Paste the statistics for the case into the summary file
        Workbooks.Open Filename:="F:\USERS\MCM\40X\LATTIME.JVB"
        Selection.Insert Shift:=xlDown
        Application.CutCopyMode = False
        ActiveWorkbook.Save
        ActiveWindow.Close
        ActiveWorkbook.Saved = True
        ActiveWindow.Close
        ActiveWorkbook.Saved = True
        ActiveWindow.Close
        Selection.Delete Shift:=xlUp
        Range("A2").Select
        Application.ScreenUpdating = True
'Continue looping the macro until all of the cases contained in this vector _
    file have been separated and no data is left in the vector file.
        CASENUM = Range("A2").Value
    Wend
'If there is more than one vector file to separate, open the next file
    ActiveWorkbook.Saved = True
    ActiveWindow.Close
    GoTo OpenLine
' End the macro and refresh the screen
```

-97-

'VB Macro Source Code

```
LastLine:
    ActiveWorkbook.Saved = True
    ActiveWindow.Close
    Application.ScreenUpdating = True
End Sub
```

The following is the source code listing of a computer program for the neural network as set forth in Example XII.

```
/*******************************     ****************************    ****************

File:          sigsin.c
Contents:      Back Propagation neural networks with
               sigmoid, sinusoid and gaussian activation
               function. Data normalized by mean and std.
Date:          Dec, 17, 1992

**********************************************************************************/ include         <math.h>
include         <stdio.h>
#define          TRUE            1
#define          FALSE           0
#define          EQUAL           0
#define          SAMPLED         1
#define          UNSAMPLED       0
#define          SINUSOID        0
#define          SIGMOID         1
#define          GAUSSIAN        2
#define          LINEAR          3
#define          NEWEXP          1
#define          RESUM           0
#define          SIG(x)          1.0/(1.0 + exp((double)(-x/10.0)))
#define          SIN(f, x)       sin((double)(f*x))
#define          GAUS(x)         exp((double)(-x*x/40.0))
#define          SLOPE(f, x)     cos((double)(f*x))
#define          MaxPtns         1000                    /*Max training + test patterns*/
#define          MaxLayerN       2                       /*Max LayerN in configuration*/
#define          MaxWtN          40                      /*Max weights per nuron*/
#define          MaxStrLen       100                     /*Maximum String Length*/
#define          MaxInputN       20                      /*Maximum data input lines*/
#define          NxtLn(s, File)  fgets((char*)s,MaxStrLen,(FILE*)File)

/*Network configuration
and control parameters*/ int      TrainPtns = 16;                             /*Total training patterns*/
int      TestPtns = 16;                              /*Total test patterns*/
int      InputN = 4;                                 /*Total input nurons*/
int      OutputN = 1;                                /*Total output nurons*/
int      LayerN = 2;                                 /*Total LayerN*/
int      NeuronInLayer[MaxLayerN] = {8, 1};          /*Total nurons in each layer*/
int      ActInLayer[MaxLayerN] = {1, 1};             /*Action function configs*/
float    LearnRate = 0.5;                            /*Learning rate*/
float    Threshold = 0.01;                           /*Termination condition*/
float    Frequency = 3.0;                            /*Sinusoid frequency*/
float    InitialRange = 2.0;                         /*Initial range for network*/
float    InputScale = 1.0;                           /*Input Normlization Factor*/
int      RptRate = 20;                               /*Reprot rate*/
int      MaxLoops = 2000;                            /*Maximum loops*/
int      RandSeed = 123456789;                       /*Random seed*/
char     TrainFile[20] = "Traing";                   /*Traingin data file name*/
char     TestFile[20] = "Ttest";                     /*Test data file name*/
char     ReportFile[20] = "Report";                  /*Output dowenload file*/
char     NetworkFile[20] = "Network";                /*Final NN sctructure*/

/*Input data*/
float    *DataIn[MaxPtns];                           /*Normalized training patterns*/
float    *DataOut[MaxPtns];                          /*Normalized training patterns*/
float    mean[MaxInputN];                            /*Input data mean buffer*/
float    std[MaxInputN];                             /*Input data std buffer*/
float    *InputLayer;                                /*Array of input nurons*/
float    *Target;
char     TrainPrefix[MaxStrLen] = "../cdi-data2/";/*Train data file prefix*/
char     TestPrefix[MaxStrLen] = "../cdi-data2/";/*Test data file prefix*/
```

-100-

```
typedef struct Neuron {
                        float   Wt[MaxWtN];
                        float   Biase;
                        float   Sum;
                        float   Out;
                        float   Error;
                        float   Delta;
                        int     Activation;
                        }NEURON;

NEURON          *Layer[MaxLayerN];

char *HELP = "Usage:    sigsin NewExpFlag.\n";

main(argc, argv)
int     argc;
char    **argv;
{
int             Loops, Pattern;
int             Spool[MaxPtns], RandSample;
float           SumError;
double          drand48();
void            Initialization();
void            Resum();
void            Output();
void            BackPropagation();
void            DumpOutput();

if((argc==1)||(atoi(argv[1])==NEWEXP))
        Initialization();
else if(atoi(argv[1]) == RESUM)
        Resum();
else{
        printf("%s\n", HELP);
        exit(0);
        }

Loops = 0;
SumError = (float)HUGE;
while((Loops++ <= MaxLoops) && (SumError >= Threshold)){
        for(Pattern=0; Pattern < TrainPtns; Pattern++)  /*Mark as unsampled*/
                Spool[Pattern] = UNSAMPLED;

SumError = 0.0;
        for(Pattern = 0; Pattern < TrainPtns; Pattern++){
                RandSample = TrainPtns * drand48();     /*Randomly sample patns*/
                while(Spool[RandSample] == SAMPLED)
                        RandSample = TrainPtns * drand48();/*Sampled? try other*/
                Output(RandSample);
                BackPropagation();
                DumpOutput(Pattern, Loops, RandSample, &SumError);
                Spool[RandSample] = SAMPLED;            /*Marked as sampled*/
                }
        } if(TestPtns){
        SumError = 0.0;
        for(Pattern = TrainPtns; Pattern < TestPtns + TrainPtns; Pattern++){
                Output(Pattern);
                DumpOutput(Pattern, -1, Pattern, &SumError);
                }
        }
exit();
```

-101-

}

/************************************************************

Routine:      Initialization()

Get in arguments, allocate memory.

************************************************************/

```c
void    Initialization()
{
void    ReportArg();
void    GetArguments();
void    AllocateMemory();
void    GetData();
void    srand48();
void    InitialNetwork();
void    NormData();

GetArguments();
ReportArg(NEWEXP);
AllocateMemory();
GetData();
NormData();
srand48(RandSeed);
InitialNetwork();
}
```

/************************************************************

Routine:      GetArguments()

Collect control and network
              configuration parameters.

************************************************************/

```c
void    GetArguments()
{
int             i, *ip, tmp;
char            TmpC, TmpS[100];
FILE            *ArgFile;
void            ReadInStr();

if((ArgFile = fopen("arg", "r")) == NULL){
        printf("cannot open file arg to read\n");
        exit(1);
        } while((TmpC = getc(ArgFile)) != EOF){
        ungetc(TmpC, ArgFile);
        ReadInStr(TmpS, ArgFile);
        if(strcmp(TmpS, "Training Data File:")==EQUAL)
                ReadInStr(TrainFile, ArgFile);
        else if(strcmp(TmpS, "Test Data File:")==EQUAL)
                ReadInStr(TestFile, ArgFile);
        else if(strcmp(TmpS, "Report Data File:")==EQUAL)
                ReadInStr(ReportFile, ArgFile);
        else if(strcmp(TmpS, "Network Structure File:")==EQUAL)
                ReadInStr(NetworkFile, ArgFile);
        else if(strcmp(TmpS, "Training Patterns:")==EQUAL){
                fscanf(ArgFile, "%d", &TrainPtns);
                NxtLn(TmpS, ArgFile);
                }
```

```c
        else if(strcmp(TmpS, "Test Patterns:")==EQUAL){
                fscanf(ArgFile, "%d", &TestPtns);
                NxtLn(TmpS, ArgFile);
                }
        else if(strcmp(TmpS, "Input Neurons:")==EQUAL){
                fscanf(ArgFile, "%d", &InputN);
                NxtLn(TmpS, ArgFile);
                }
        else if(strcmp(TmpS, "Output Neurons:")==EQUAL){
                fscanf(ArgFile, "%d", &OutputN);
                NxtLn(TmpS, ArgFile);
                }
        else if(strcmp(TmpS, "Layers:")==EQUAL){
                fscanf(ArgFile, "%d", &LayerN);
                NxtLn(TmpS, ArgFile);
                }
        else if(strcmp(TmpS, "Neurons in Layer:")==EQUAL){
                for(i=0; i<LayerN; i++)
                        fscanf(ArgFile, "%d", &NeuronInLayer[i]);
                NxtLn(TmpS, ArgFile);
                }
        else if(strcmp(TmpS, "Activation in Layer:")==EQUAL){
                for(i=0; i<LayerN; i++)
                        fscanf(ArgFile, "%d", &ActInLayer[i]);
                NxtLn(TmpS, ArgFile);
                }
        else if(strcmp(TmpS, "Learning Rate:")==EQUAL){
                fscanf(ArgFile, "%f", &LearnRate);
                NxtLn(TmpS, ArgFile);
                }
        else if(strcmp(TmpS, "Random Seed:")==EQUAL){
                fscanf(ArgFile, "%d", &RandSeed);
                NxtLn(TmpS, ArgFile);
                }
        else if(strcmp(TmpS, "Input Scaling:")==EQUAL){
                fscanf(ArgFile, "%f", &InputScale);
                if(InputScale==0.0){
                        printf("Warning: 0 scaling factor\n");
                        exit(0);
                        }
                NxtLn(TmpS, ArgFile);
                }
        else if(strcmp(TmpS, "Ending Threshold:")==EQUAL){
                fscanf(ArgFile, "%f", &Threshold);
                NxtLn(TmpS, ArgFile);
                }
        else if(strcmp(TmpS, "Frequency:")==EQUAL){
                fscanf(ArgFile, "%f", &Frequency);
                NxtLn(TmpS, ArgFile);
                }
        else if(strcmp(TmpS, "Initial Range:")==EQUAL){
                fscanf(ArgFile, "%f", &InitialRange);
                NxtLn(TmpS, ArgFile);
                }
        else if(strcmp(TmpS, "Report Rate:")==EQUAL){
                fscanf(ArgFile, "%d", &RptRate);
                NxtLn(TmpS, ArgFile);
                }
        else if(strcmp(TmpS, "Maximum Loops:")==EQUAL){
                fscanf(ArgFile, "%d", &MaxLoops);
                NxtLn(TmpS, ArgFile);
                }
        } fclose(ArgFile);
}
```

```
/*************************  *******************************.************

Routine:      ReadInStr

Read into string, disgard newline character

*************************************************************************/ void    ReadInStr(Str, InFile)
char    *Str;
FILE    *InFile;
{
int     Len;

fgets(Str, MaxStrLen, InFile);
*(Str + strlen(Str) - 1) = '\0';          /*Disgard newline and pad null*/
}

/*************************************************************************

Routine:      ReportArg

Reporte the input arguments.

*************************************************************************/ void    ReportArg(NewExpFlag)
int             NewExpFlag;
{
register        i, *ip;
FILE            *RptFile;

if(NewExpFlag){
        if((RptFile=fopen(ReportFile, "w"))==NULL){
                printf("cannot open file %s to write\n", ReportFile);
                exit(1);
                }
        }
else{
        if((RptFile=fopen(ReportFile, "a"))==NULL){
                printf("cannot open file %s to append\n", ReportFile);
                exit(1);
                }
        } if(!NewExpFlag)
        fprintf(RptFile, "\nRESUMED FROM THE PREVIOUSLY STOPED PROCESS\n\n");
fprintf(RptFile, "Training Data File: %s\n", TrainFile);
fprintf(RptFile, "Test Data File: %s\n", TestFile);
fprintf(RptFile, "Report Data File: %s\n", ReportFile);
fprintf(RptFile, "Network Structure File: %s\n", NetworkFile);
fprintf(RptFile, "Training Patterns: %d\n", TrainPtns);
fprintf(RptFile, "Test Patterns: %d\n", TestPtns);
fprintf(RptFile, "Input Neurons: %d\n", InputN);
fprintf(RptFile, "Output Neurons: %d\n", OutputN);
fprintf(RptFile,"Layers: %d\n", LayerN);
fprintf(RptFile, "Neurons in Layer: ");

ip = NeuronInLayer;
for(i=0; i<LayerN; i++)
        fprintf(RptFile, "%d\t", *ip++);

fprintf(RptFile, "\n");
fprintf(RptFile, "Activation in Layer: ");
```

```
        ip = ActInLayer;
        for(i=0; i<LayerN; i++)
                fprintf(RptFile, "%d\t", *ip++);

fprintf(RptFile, "\n");
        fprintf(RptFile,"Learn Rate: %f\n", LearnRate);
        fprintf(RptFile,"Random Seed: %d\n", RandSeed);
        fprintf(RptFile,"Input Scaling: %f\n", InputScale);
        fprintf(RptFile,"Ending Threshold: %f\n", Threshold);
        fprintf(RptFile,"Frequency: %f\n", Frequency);
        fprintf(RptFile,"Initial Range %f\n", InitialRange);
        fprintf(RptFile,"Report Rate %d\n", RptRate);
        fprintf(RptFile,"Maximum Loops %d\n", MaxLoops);

fclose(RptFile);
        }

/****************************************************

Routine:        GetData

Read in training and test data from file

****************************************************/ void    GetData()
{
register        i, j;
float           *fp1, *fp2, ftmp;
char            *TmpStr;
FILE            *DataFile;

/*Get training data*/
TmpStr = (char *)strcat(TrainPrefix, TrainFile);
if((DataFile = fopen(TmpStr,  "r")) == NULL){
        printf("cannot open file %s to read\n", TmpStr);
        exit(1);
        } for(i=0; i<TrainPtns; i++){
        fp1 = DataIn[i];
        fp2 = DataOut[i];
        for(j=0; j<InputN; j++){
                fscanf(DataFile, "%f", &ftmp);
                *fp1++ = ftmp/InputScale;
                }
        for(j=0; j<OutputN; j++)
                fscanf(DataFile, "%f", fp2++);
        }

/*Get test data*/
TmpStr = (char *)strcat(TestPrefix, TestFile);
if(TestPtns){
        if((DataFile = fopen(TmpStr,  "r")) == NULL){
                printf("cannot open file %s to read\n", TmpStr);
                exit(1);
                } for(i=TrainPtns; i<TrainPtns + TestPtns; i++){
                fp1 = DataIn[i];
                fp2 = DataOut[i];
                for(j=0; j<InputN; j++){
                        fscanf(DataFile, "%f", &ftmp);
                        *fp1++ = ftmp/InputScale;
                        }
                for(j=0; j<OutputN; j++)
```

```
                fscanf(DataFile, "%f", fp2++);
        }
    }
}

/*******************************************************
Routine:        NormData Normalize input data
                to range [0,1].

*******************************************************/ void    NormData()
{
int     i, j, ptns;
float   ftmp;
FILE    *RptFile;

ptns = TrainPtns;
for(i=0; i<InputN; i++){
        ftmp = 0.0;
        for(j=0; j<ptns; j++)
                ftmp += DataIn[j][i];
        mean[i] = ftmp/ptns;
        } for(i=0; i<InputN; i++){
        ftmp = 0.0;
        for(j=0; j<ptns; j++)
                ftmp += pow((DataIn[j][i] - mean[i]),2.0);
        std[i] = pow((ftmp/ptns),0.5);
        } ptns = TrainPtns + TestPtns;
for(i=0; i<InputN; i++)
        for(j=0; j<ptns; j++)
                DataIn[j][i] = (DataIn[j][i]-mean[i])/std[i];

if((RptFile = fopen(ReportFile, "a"))==NULL){
        printf("cannot open file %s to write\n", ReportFile);
        exit(0);
        } fprintf(RptFile, "Mean\tSTD\n");
for(i=0; i<InputN; i++){
        fprintf(RptFile, "%f\t", mean[i]);
        fprintf(RptFile, "%f\n", std[i]);
        printf("%f\t", mean[i]);
        printf("%f\n", std[i]);
        }
fprintf(RptFile,"\n\n");
fprintf(RptFile, "Loops\tPtns\tNN-Out\tTarget\tSq-Err\n");
fclose(RptFile);
}

/*******************************************************
Routine:        AllocateMemory Allocate memory to nuron
                structure and other arrays

*******************************************************/ void    AllocateMemory()
{
```

```
register        i;

/*Allocate space
for training data*/ for(i=0; i<TrainPtns + TestPtns; i++){
        if((DataIn[i] = (float*)calloc(InputN, sizeof(float)))==NULL){
                printf("cannot allocate memory to DataIn\n");
                exit(1);
                }
        if((DataOut[i] = (float*)calloc(OutputN, sizeof(float)))==NULL){
                printf("cannot allocate memory to DataOut\n");
                exit(1);
                }
        }

/*Allocate space for
input layer nurons*/ if((InputLayer = (float*)calloc(InputN, sizeof(float)))==NULL){
        printf("cannot allocate memory to InputLayer\n");
        exit(1);
        }

/*Allocate space for nurons
in the rest of Layers*/ for(i=0; i<LayerN; i++)
        if((Layer[i]=(NEURON *)calloc(NeuronInLayer[i],sizeof(NEURON)))==NULL){
                printf("cannot allocate memory to Layer[%d]\n", i);
                exit(1);
                }

/*Allocate space for target values*/ if((Target = (float*)calloc(OutputN, sizeof(float)))==NULL){
        printf("cannot allocate memory to Target\n");
        exit(1);
        }
}
/***********************************************************************

Routine:        InitialNetwork

Initialize the activation function configuration for
                each layer (nuron) and nuron structure in the network.

***********************************************************************/ void    InitialNetwork()
{
register        i, j, k;
float           *fp;
NEURON          *NeuronP;
double          drand48();

for(i=0; i<LayerN; i++){
        for(NeuronP = Layer[i], j=0; j<NeuronInLayer[i]; NeuronP++, j++){
                NeuronP->Activation = ActInLayer[i];
                NeuronP->Biase = (drand48() - 0.5) * InitialRange;
                NeuronP->Sum = 0.0;
                NeuronP->Out = 0.0;
                NeuronP->Error = 0.0;
                fp = NeuronP->Wt;
```

-107-

```c
                if(i==0)
                        for(k=0; k<InputN; k++)
                                *fp++ = (drand48() - 0.5) * InitialRange;
                else
                        for(k=0; k<NeuronInLayer[i-1]; k++)
                                *fp++ = (drand48() - 0.5) * InitialRange;
                }
        }
}

/**********************************************************************************

Routine:        ReadInNetwork

Initialize the activation function configuration for
                each layer (nuron) and read in the network weight
                values from stoped process.

**********************************************************************************/ void    ReadInNetwork()
{
register        i, j, k;
char            Header, Ctmp;
float           *fp;
NEURON          *NeuronP;
FILE            *NetFp;

if((NetFp=fopen(NetworkFile, "r"))==NULL){
        printf("cannot open file file %s to read\n", NetworkFile);
        exit(1);
        }

Header = 7 + InputN;
while(--Header){                                        /*Read off network file header*/
        fscanf(NetFp, "%c", &Ctmp);
        while(Ctmp!='\n')
                fscanf(NetFp, "%c", &Ctmp);
        } for(i=0; i<LayerN; i++){
        for(NeuronP = Layer[i], j=0; j<NeuronInLayer[i]; NeuronP++, j++){
                NeuronP->Activation = ActInLayer[i];
                fscanf(NetFp, "%f", &(NeuronP->Biase));
                fp = NeuronP->Wt;
                if(i==0)
                        for(k=0; k<InputN; k++)
                                fscanf(NetFp, "%f", fp++);
                else
                        for(k=0; k<NeuronInLayer[i-1]; k++)
                                fscanf(NetFp, "%f", fp++);
                }
        }
fclose(NetFp);
}

/**********************************************************************************

Routine:        Resum()

Resum a stoped process.

**********************************************************************************/
```

```
void    Resum()
{
void    ReportArg();
void    GetArguments();
void    AllocateMemory();
void    GetData();
void    InitialNetwork();
void    NormData();

GetArguments();
ReportArg(RESUM);
AllocateMemory();
GetData();
NormData();
ReadInNetwork();
}

/***************************************************************************

Routine:    Output

Calculate the output for each nuron.

****************************************************************************/ void    Output(Pattern)
int     Pattern;
{
int             i, j;
float           Tmp, rt;
NEURON          *NeuronP;
void            GetPattern();
float           GetSum();

GetPattern(Pattern);

for(i=0; i<LayerN; i++){
        NeuronP = Layer[i];
        for(j=0; j<NeuronInLayer[i]; j++, NeuronP++){
                rt = GetSum(i, j);
                Tmp = rt + NeuronP->Biase;
                NeuronP->Sum = Tmp;
                switch (NeuronP->Activation){
                        case SIGMOID:
                                NeuronP->Out = SIG(Tmp);
                                break;
                        case SINUSOID:
                                NeuronP->Out = SIN(Frequency, Tmp);
                                break;
                        case GAUSSIAN:
                                NeuronP->Out = GAUS(Tmp);
                                break;
                        case LINEAR:
                                NeuronP->Out = Tmp;
                                break;
                        default:
                                printf("invalide activation function type\n");
                                exit(0);
                }
        }
}
}
/***************************************************************************

Routine:    GetPattern
```

Get input pattern for network

```
***********************************************************************/ void    GetPattern(Pattern)
int     Pattern;
{
register        i, j;
float           *fp1, *fp2;

fp1 = InputLayer;
fp2 = DataIn[Pattern];
for(i=0; i<InputN; i++)
        *fp1++ = *fp2++;

fp1 = Target;
fp2 = DataOut[Pattern];
for(i=0; i<OutputN; i++)
        *fp1++ = *fp2++;
}

/***********************************************************************

Routine:        GetSum()

Calculate the sum input for each nuron

***********************************************************************/ float   GetSum(LayerIndex, NeuronIndex)
int     LayerIndex, NeuronIndex;
{
register        i, j;
float           Sum, *fp1, *fp2;
NEURON          *NeuronP1, *NeuronP2;

if(LayerIndex == 0){
        NeuronP1 = (NEURON *)(Layer[LayerIndex] + NeuronIndex);
        fp1 = InputLayer;
        fp2 = NeuronP1->Wt;
        for(Sum=0.0, i=0; i<InputN; i++)
                Sum += (*fp1++ * *fp2++);
        }
else{
        NeuronP1 = (NEURON *)(Layer[LayerIndex] + NeuronIndex);
        NeuronP2 = Layer[LayerIndex - 1];
        fp1 = NeuronP1->Wt;
        for(Sum=0.0, i=0; i<NeuronInLayer[LayerIndex-1]; i++, NeuronP2++)
                Sum += (NeuronP2->Out * *fp1++);
        }
return(Sum);
}

/***********************************************************************

Routine:        BackPropgation

Modify network through backpropgation.

***********************************************************************/ void    BackPropagation()
{
void    GetDelta();
void    UpdateWt();
```

-110-

```
GetDelta();
UpdateWt();

}
/********************************************************************

Routine:    GetDelta

Calculate delta values for each nuron in the
            network, out layer and internal layer;

********************************************************************/ void    GetDelta()
{
register    i;
void        OutLayerDelta();
void        InterLayerDelta();

OutLayerDelta();

for(i=LayerN-2; i>=0; i--)
        InterLayerDelta(i);

}

/********************************************************************

Routine:    OutLayerDelta

Calculate output layer delta

********************************************************************/ void    OutLayerDelta()
{
register    i;
float       TmpOut;
NEURON      *NeuronP;

for(NeuronP = Layer[LayerN-1], i=0; i<NeuronInLayer[LayerN-1]; NeuronP++, i++){
        TmpOut = NeuronP->Out;
        NeuronP->Error = Target[i] - TmpOut;
        switch (NeuronP->Activation){
                case SIGMOID:
                        NeuronP->Delta = TmpOut * (1 - TmpOut) * NeuronP->Error;
                        break;
                case SINUSOID:
                        NeuronP->Delta =SLOPE(Frequency, NeuronP->Sum) * NeuronP->Error;
                        break;
                case GAUSSIAN:
                        NeuronP->Delta = -NeuronP->Sum * TmpOut * NeuronP->Error/20;
                        break;
                case LINEAR:
                        NeuronP->Delta = NeuronP->Error;
                        break;
                default:
                        printf("invalide activation function type\n");
                        exit(0);
                }
        }
}
```

-111-

```
/*************************    ****************************,   :**************

Routine:        InterLayerDelta

Calculate internal layer Delta

*************************************************************************/ void    InterLayerDelta(LayerIndex)
int     LayerIndex;
{
register        i;
float           TmpOut;
NEURON          *NeuronP;
float           NeuronError();

for(NeuronP=Layer[LayerIndex],i=0; i<NeuronInLayer[LayerIndex]; NeuronP++,i++){
        TmpOut = NeuronP->Out;
        NeuronP->Error = NeuronError(LayerIndex, i);
        switch (NeuronP->Activation){
                case SIGMOID:
                        NeuronP->Delta = TmpOut * (1 - TmpOut) * NeuronP->Error;
                        break;
                case SINUSOID:
                        NeuronP->Delta =SLOPE(Frequency, NeuronP->Sum) * NeuronP->Error;
                        break;
                case GAUSSIAN:
                        NeuronP->Delta = -2 * NeuronP->Sum * TmpOut * NeuronP->Error;
                        break;
                case LINEAR:
                        NeuronP->Delta = NeuronP->Error;
                        break;
                default:
                        printf("invalide activation function type\n");
                        exit(0);
                }
        }
}

/***************************************************************************

Routine:        NeuronError

Calculate error for each nuron in the internal LayerN.

*************************************************************************/ float   NeuronError(LayerIndex, NeuronIndex)
int     LayerIndex, NeuronIndex;
{
register        i;
float           Error;
NEURON          *NeuronP;

Error = 0.0;
for(NeuronP=Layer[LayerIndex+1],i=0;i<NeuronInLayer[LayerIndex+1];NeuronP++,i++)
        Error += (NeuronP->Wt[NeuronIndex] * NeuronP->Delta);

return(Error);
}

/***************************************************************************

Routine:        UpdateWt

Modify the weights associated with each nuron.
```

-112-

```
/***************************     *************************.**************/ void    UpdateWt()
{
register        i;
void            FirstLayerWt();
void            RestLayerWt();

FirstLayerWt();

for(i=1; i<LayerN; i++)
        RestLayerWt(i);
}

/**************************************************************************

Routine:        FirstLayerWt

Modify the weights related to the first layer nurons.

**************************************************************************/ void    FirstLayerWt()
{
register        i, j;
float           *fp1, *fp2;
NEURON          *NeuronP;

for(NeuronP = Layer[0], i=0; i<NeuronInLayer[0]; NeuronP++, i++){
        fp1 = InputLayer;
        fp2 = NeuronP->Wt;
        for(j=0; j<InputN; j++)
                *fp2++ += LearnRate * NeuronP->Delta * *fp1++;
        NeuronP->Biase += (LearnRate * NeuronP->Delta);
        }
}

/**************************************************************************

Routine:        RestLayerWt

Modify the weights related to the nurons of other LayerN.

**************************************************************************/ void    RestLayerWt(LayerIndex)
{
register        i, j;
float           *fp;
NEURON          *NeuronP1, *NeuronP2;

for(NeuronP1=Layer[LayerIndex],i=0;i<NeuronInLayer[LayerIndex];NeuronP1++,i++){
        fp = NeuronP1->Wt;
        NeuronP2 = Layer[LayerIndex - 1];
        for(j=0; j<NeuronInLayer[LayerIndex - 1]; j++){
                *fp++ += (LearnRate*NeuronP1->Delta*NeuronP2->Out);
                NeuronP2++;
                }
        NeuronP1->Biase += (LearnRate * NeuronP1->Delta);
        }
}
                                -113-

/**************************************************************************
```

```
Routine:    DumpOutput

Save output to report file and rturn it to main.
***********************************************************************/ void    DumpOutput(PtnCnt, Loops, PtnSampled, SumError)
float   *SumError;
int     Loops, PtnCnt, PtnSampled;
{
register    i;
float       SqError, OutError, *fp;
NEURON      *NeuronP;
FILE        *RptFile;
void        DumpNetwork();

fp = DataOut[PtnSampled];
NeuronP = Layer[LayerN-1];
SqError = 0.0;
for(i=0;i<OutputN;fp++,NeuronP++,i++){
        OutError = *fp - NeuronP->Out;
        SqError += OutError*OutError;
        }
*SumError += SqError;

if((Loops % RptRate == 0) || (Loops == -1)){
        if((RptFile=fopen(ReportFile, "a"))==NULL){
                printf("cannot open file %s to append.\n", ReportFile);
                exit(1);
                } fprintf(RptFile, "%d\t%d\t", Loops, PtnSampled);
        NeuronP = Layer[LayerN-1];
        for(NeuronP=Layer[LayerN-1],i=0;i<NeuronInLayer[LayerN-1];NeuronP++,i++)
                fprintf(RptFile, "%6.4f\t", NeuronP->Out);

fp = DataOut[PtnSampled];
        for(i=0; i<OutputN; i++)
                fprintf(RptFile, "%6.4f\t", *fp++);

fprintf(RptFile, "%6.4f\t", SqError);

fprintf(RptFile, "\n");
        fclose(RptFile);
        } if(((Loops%RptRate==0)&&(PtnCnt==TrainPtns-1))||(PtnCnt==TrainPtns+TestPtns-1)){
        if((RptFile=fopen(ReportFile, "a"))==NULL){
                printf("cannot open file %s to append.\n", ReportFile);
                exit(1);
                }
        fprintf(RptFile, "SumError %6.4f\n\n\n", *SumError);
        fclose(RptFile);

DumpNetwork();
        }
}

/************************************************************************
Routine:    DumpNetwork()

Save the final network configuration, including network
            parameters(layers, layer configuration, activation function
            configuration), weights, biases.
```

```
/*************************        ****************************     ***************/
void DumpNetwork()
{
register        i, j, k, WtN;
float           *fp;
NEURON          *NeuronP;
FILE            *NetFile;

if((NetFile=fopen(NetworkFile, "w"))==NULL){
        printf("cannot open file %s to write\n", NetworkFile);
        exit(1);
        } fprintf(NetFile, "%d\t%d\n", InputN, OutputN);
fprintf(NetFile, "%d\n", LayerN);
for(i=0; i<LayerN; i++)
        fprintf(NetFile, "%d\t", NeuronInLayer[i]);
fprintf(NetFile, "\n");
for(i=0; i<LayerN; i++)
        fprintf(NetFile, "%d\t", ActInLayer[i]);
fprintf(NetFile, "\n%6.4f\n", Frequency);
for(i=0; i<InputN; i++){
        fprintf(NetFile, "%f\t", mean[i]);
        fprintf(NetFile, "%f\n", std[i]);
        }
fprintf(NetFile, "\n\n");

for(i=0;i<LayerN;i++){
        WtN = i==0 ? InputN : NeuronInLayer[i-1];
        for(NeuronP=Layer[i],j=0;j<NeuronInLayer[i];NeuronP++,j++){
                fprintf(NetFile, "\n%6.4f\n", NeuronP->Biase);
                for(fp=NeuronP->Wt, k=0; k<WtN; k++){
                        fprintf(NetFile, "%6.4f ", *fp++);
                        if(k%8==7)
                                fprintf(NetFile, "\n");
                        }
                }
        } fclose(NetFile);
}
```

REFERENCES

The following references, to the extent that they provide exemplary procedural or other details supplementary to those set forth herein, are specifically incorporated herein by reference.

1. Ashenayi, K., Vogh, J., Tai, H.M., Sayeh, M.R., Mostafavi, M.T., "Single-Layer Perceptron Capable of Classifying 2N÷1 Distinct Patterns," *IASTED International Journal of Modelling and Simulation*, Vol. 10, No. 4, 1990, pp. 124-128.

2. Ashenayi, K., Singh, S., and Sayeh, M.R., "Pattern Classification Using Associative Memory," paper presented at 31 St. Midwest Symposium on Circuits and Systems, pp. 169-172, Aug. 11-12, 1988.

3. Ashenayi, K., Vogh, J., and Sayeh, M.R., 1992, "Gaussian Perceptron Capable of Classifying "2N÷1" Distinct Classes of Input Patterns," *IASTED Journal of Control and Computers*, Vol. 20, No. 2, pp. 54-60.

4. Austenfeld, MS, Treatment of Stage A1 prostate cancer: The case for observation. Seminars in Urology, XI: 58-63, 1993.

5. Bahnson, RR. Treatment of Stage A1 prostate cancer: The Case for treatment. Seminars in Urology, XI: 54-57, 1993.

6. Bibbo, M, Kim, DH, di Lareto, C, Galera-Davidson, H, Thompson, D, and Dytch, HE. Architectural morphometric and photometric features and their relationship to the main subjective clues of grading prostate cancer. Anal. Quant. Cytol. Histol., 12: 85-90, 1990.

7. Block, H.D., "The Perceptron: a Model for Brain Functioning. I," Reviews of Modern Physics, 34, pp. 123-135, 1962.

8. Bonner, R.B., Hemstreet, G.P., Fradet, Y., Min, K.Y., Hurst, R.E., 1993, "Bladder Cancer Risk Assessment with Quantitative Fluorescence Image Analysis of Tumor Markers in Exfoliated Bladder Cells. Cancer 72: 2461-69.

9. Boone, CW and Kelloff, GJ. Intraepithelial neoplasia, surrogate endpoint biomarkers, and cancer chemoprevention. J. Cell. Biochem. (Suppl), 17F: 37-48, 1993.

10. Boring, C.C., Squires, T.S. and Tsong, T. Cancer Statistics, CA, 41:19-36, 1991.

11. Bostwick, DG, Montironi, R, Nagle, R, Pretlow, T, Miller, G, Wheeler, T, Epstein, JI, and Sakr, W. Current and proposed biologic markers in prostate cancer. J. Cell. Biochem. (Suppl.) 16H: 65-67, 1992.

12. Bostwick, DG, Graham, SD, Napalkov, P, Abrahamsson, P-A, di Sant'Agnese, PA, Algaba F, Hoisaeter PA, Lee, F, Littrup, P, Mostofi, FK, Denis, L, Schroeder, F, Murphy, GP. Staging of early prostate cancer: A proposed tumor volume-based prognostic index. Urology, 41: 403-411, 1993.

13. Bostwick, DG, Amin, MB, Dundore, P, Marsh, W, and Schultz, DS. Architectural patterns of high grade prostatic intraepithelial neoplasia. Human Pathology, 24: 298-310, 1993.

14. Brady, M.L., Raghavan, R., and Slawny, J., "Back Propagation Fails to Separate Where Perceptron Succeed," IEEE Transactions on Circuits and Systems, Vol. 36, No. 5, pp. 665-674, May 1989.

15. Cancer Facts and Figures - 1993. New York: American Cancer Society, Inc.,

16. Cantrell, B.B., deklerk, D.P., Eggleston, J.C., Boitnott, J.K. and Walsh, P.C. Pathological factors that influence prognosis in stage A prostatic cancer: The influence of extent versus grade. J. Urol., 125:516, 1981.

17. Carpenter, G.A. and Grossberg, S., "The ART of Adaptive Pattern Recognition by Self-Organizing Neural Network," Computer, pp. 77-88, March 1988.

18. Carter, H.B. and Coffey, D.S. Prostate cancer: The magnitude of the problem in the United States. In: *A Multidisciplinary Analysis of Controversies in the Management of Prostate Cancer*, Coffey, D.S., Resnick, M.I., Dorr, F.A. and Karr, J.P. (eds.), New York: Plenum Publishing Corp., pp. 1-7, 1988.

19. Catalona, W.J. and Bigg, S.W. Nerve-sparing radical prostatectomy: evaluation of results after 250 patients. J. Urol. 143:538-543, 1990.

20. Christen, R, Xiao, J, Minimo, C, Gibbons, G, Fitzpatrick, BT, Galera-Davidson, H, Bartels, PH, and Bibbo, M. Chromatin texture features in hematoxylin and eosin-stained prostate tissue. Analytical Quant. Cytol. Histol., 15: 383-388, 1991.

21. Clark, T.D., Askin, F.B. and Bagnell, C.F. Nuclear roundness factor: A quantitative approach to grading in prostatic carcinoma, reliability of needle biopsy tissue, and the effect of tumor stage on usefulness. Prostate, 10:199, 1987.

22. DARPA Neural Network Study, AFCEA International Pres, Fairfax, Virginia, November 1988.

23. Dawson, A.E., Cibas,E.S., Bacus, J.W. and Weinberg, D.S. "Chromatin Texture Measurement by Markovian Analysis, Use of Nuclear Models to Define and Select Texture Features," Analytical and Quantitative Cytology and Histology, 15: 227-35, 1993.

24. Diamond DA, Berry SJ, Umbricht C, Jewett HJ, and Coffey DS. Computerized image analysis of nuclear shape as a prognostic factor for prostatic cancer. *The Prostate* 1982; 3:321-332.

25. Diamond DA, Berry SJ, Jewett HJ, Eggleston, and Coffey DS. A new method to assess metastatic potential of human prostate cancer: relative nuclear roundness. *J Urol* 1982; 128:729-734.

26. Eichenberger, T., Mihatsch, M.J., Oberholzer, M., Gschwind, R. and Rutishauser, G. <u>Prostate Cancer. Part A: Research, Endocrine Treatment, and Histopathology</u>. Alan R. Liss, Inc., New York, pp. 533-537, 1987.

27. Epstein, J.I., Oesterling, J.E. and Walsh, P.C. Tumor volume versus percentage involved by tumor correlated with progression in stage A prostatic cancer. J. Urol. 139:980, 1988.

28. Epstein, J.I., Berry, S.J. and Eggleston, J.C. Nuclear roundness factor: A predictor of prognosis in untreated stage A2 prostate cancer. Cancer 54:1666, 1984.

29. Franks, LM. Latent carcinoma of the prostate. J. Pathol Bacteriol. 68: 603-616, 1954.

30. Freiha, F.S. Selection criteria for radical prostatectomy based on morphometric studies. In: Consensus Development Conference on Management of Clinically Localized Prostate Cancer, Program and Abstracts, p. 73, June 15-17, 1987.

31. Gibbons, R.P., Correa, R.J., Jr., Brannen, G.E. and Mason, J.T. Total prostatectomy for localized prostatic cancer. J. Urol., 131:73, 1984.

32. Gleason DF, The Veterans Administrative Cooperative Urological Research Group. Histological grading and clinical staging of prostatic carcinoma. In: Tannenbaum M, editor. Urologic pathology: the prostate. Philadelphia: Lea and Febiger, 1977:171-98.

33. Gleason, D.F. Histologic grading of prostatic carcinoma. In: Bostwick DG (Ed): Pathology of the Prostate, New York, Churchhill-Livingstone, pp 83-90, 1990.

34. Gleason, D.F., Mellinger, G.T. and the Veterans Administrative Cooperative Urological Research Group. Prediction of prognosis for prostatic adenocarcinoma by combined histological grading and clinical staging. J. Urol., 111:58, 1974.

35. Han, J.Y., Syeh, M.R. and Zhang, J., "Convergence and Limit Points of Neural Network and Its Applications in Pattern Recognition," IEEE Transaction on Systems, Man, and Cybernectics, Vol. 19, No. 5, pp. 1217-1222, 1989.

36. Hopfield, J.J. "Neural Networks and Physical Systems with Emergent Collective Computational Abilities," Proc. Natl. Acad. Science, USA, Vol. 79, pp. 2554-2558, April 1982.

37. Irinopoulou, T., Rigaut J.P., and Benson M.C. Toward Objective Prognostic Grading of Prostatic carcinoma Using Image Analysis. Analytical and Quantitative Cytology and histology, 15: 341-44, 1993.

38. Isaacs, J.T (Ed). Prostate Cancer Cell and Molecular Mechanisms in Diagnosis and Treatment. Cancer Surveys 11: 1-287, 1991.

39. Kohonen, T., Self-Organization and Associative Memory, 2ND Ed., Springer-Verlag, New York, 1987.

40. Lippmann, R.P., "An Introduction to Computing With Neural Nets," IEEE ASSP Magazine, pp. 4-22, April 1987.

41. Lippmann, R.P., and Martin, E.A., "Multi-Style Training for Robust Isolated-Word Speech Recognition," in ICASSP 87, April 1987, 705-708.

42. McNeal, J.E., Kindrachuk, R.A., Freiha, F.S., Bostwick, D.G., et. al. Patterns of progression in prostate cancer. Lancet, 1:60, 1986.

43. Middleton, R.G., Smith, J.A., Jr., Metzer, R.B. and Hamilton, P.E. Patient survival and local recurrence rate following radical prostatectomy for prostatic cancer. J. Urol. 136:422-, 1986.

44. Miller, G.J. and Shikes, J.L. Nuclear roundness as a predictor of response to hormonal therapy of patients with stage D2 prostatic carcinoma. IN: <u>Prognostic Cytometry and Cytopathology of prostate cancer</u>. Karr, J.P., Coffey, D.S. and Gardner W. (Eds.), Elsevier Science Publishing Co., Inc., New York, pp. 349-354, 1988.

45. Minsky, M.L. and Papert, S.A., Perceptrons, Expanded Edition, MIT Press, Cambridge, Mass., 1988.

46. Mohler JL, Partin AW, Epstein JI, Lohr WD, and Coffey DS. Nuclear roundness factor measurement for assessment of prognosis of patients with prostatic carcinoma: II. Standardization of methodology for histologic sections. *J Urol* 1988; 139:1085-1090.

47. Mohler JL, Partin AW, Lohr WD, and Coffey DS. Nuclear roundness factor measurement for assessment of prognosis of patients with prostatic carcinoma: I. Testing of a digitization system. *J Urol* 1988; 139:1080-4.

48. Mostofi FK. Grading of prostatic carcinoma. *Cancer Chemother. Rep.* 1975; 59:111-7.

49. Murphy, G.P., Gaeta, J.F., Pickren, J. and Wajsman, Z. Current status of classification and staging of prostate cancer. Cancer, 45:1889, 1980.

50. Myers, R.P. and Fleming, T.R. Course of localized adenocarcinoma of the prostate treated by radical prostatectomy. Prostate, 4: 461, 1983.

51. Narayan, P., Michael, M., Jajodia, P., Stein, R., Gonzalez, J., Ljung, B., Chu, K. and Myall, B. Automated image analysis - a new technique to predict metastatic potential of prostate carcinomas? J. Urol., 141 (4 part 2): 183 (Abstract), 1989.

52. Nowell, P.C. Mechanisms of tumor progression. Cancer Res., 46:2203, 1986.

53. Oesterling, J.E. PSA leads the way for detecting and following prostate cancer. Contemporary Urol. 5:60-81, 1993.

54. Oesterling, J.E. Prostate specific antigen: A critical assessment of the most useful tumor marker for adenocarcinoma of the prostate. J. Urol., 145:907-923, 1991.

55. Pack R and Spitz MA. Epidemiology of prostate cancer, with emphasis on familial clusters. The Cancer Bulletin, 45: 384-388, 1993.

56. Parker, D.B., "Learning-Logic," Innovation Report, 581-64, File 1, Office of Technology Licensing, Stanford University, October, 1982.

57. Partin, A.W., Pound, C.R., Clemens, J.Q., Epstein, J.I. and Walsh, P.C.: Prostate specific antigen after anatomic radical prostatectomy: The Johns Hopkins Experience after ten years. Urol. Clin. North Am., November, 20:713, 1993.

58. Partin, A.W., Yoo, J., Carter, H.B., Pearson, J.D., Chan, D.W., Epstein, J.I. and Walsh P.C. The use of prostate specific antigen, clinical stage and gleason score to predict pathologic stage in men with clinically localized prostate cancer. J. Urol. 150:105-110, 1993.

59. Partin AW, Walsh AC, Pitcock RV, Mohler JL, Epstein JI, and Coffey DS. A comparison of nuclear morphometry and Gleason grade as a predictor of prognosis in stage A2 prostate cancer: A critical analysis. *J Urol* 1989; 142:1254-1258.

60. Partin, A.W. The development of a system for the quantitative analysis of tumor cell motility: Application to prostate cancer. Doctoral Thesis, The Johns Hopkins University, 1988.

61. Partin, A.W., Carter, H.B., Chan, D.W., Epstein, J.I., Oesterling, J.E., Rock, R.C., Weber, J.P. and Walsh, P.C. Prostate specific antigen in the staging of localized prostate cancer: Influence of tumor differentiation, tumor volume and benign hyperplasia. J. Urol., 143:747, 1990.

62. Partin, A.W., Epstein, J.I., Cho, K.R., Gittelsohn, A.M. and Walsh, P.C. Morphometric measurement of tumor volume and percent of gland involvement 1as predictors of pathologic stage in clinical stage B prostate cancer. J. Urol., 141:341, 1989.

63. Partin AW, Steinberg GD, Pitcock RV, Wu L, Piantadosi S, Coffey DS, and Epstein JI. Use of nuclear morphometry, gleason histologic scoring, clinical stage, and age to predict disease-free survival among patients with prostate cancer. *Cancer* 1992, 70(1):161-168.

64. Partin, A.W., Steinberg, G.D., Pitcock, R.V., Wu, L., Piantadosi, S., Coffey, D.S. and Epstein, J.I. Use of nuclear morphometry, Gleason histologic scoring, clinical stage and age to predict disease free survival among patients with prostate cancer. Cancer 70:161-168, 1992.

65. Paulson, D.F. Radiotherapy versus surgery for localized prostatic cancer. Urol. Clin. North Am., 14:675, 1987.

66. Paulson, D.F., Stone, A.R., Walther, P.J., Tucker, J.A. and Cox, E.B. Radical prostatectomy: Anatomical predictors of success or failure. J. Urol., 136:1041, 1986.

67. Pisters LI. and Babaian RJ. Status of early prostate cancer detection. The Cancer Bulletin, 45: 389-396, 1993.

68. Pressman, N.J. "Markovian Analysis of Cervical Images," J Histochemistry and Cytochemistry, 24: 138-44, 1976.

69. Reed, J.A., Manahan, L.J., Park, C.S., and Brigati, D.J. Complete one-hour immunochemistry based on capillary action. BioTechniques 13: 434-442.

70. Reed, T. and Hans Du Buf, J., 1993, "A Review of Recent Texture segmentation and Feature Extraction Techniques," *CVGIP:Image Understanding*, 57, pp. 359-372.

71. Robey, E.L. and Schellhammer, P.F. Local failure after definitive therapy for prostatic cancer. J. Urol., 137:613, 1987.

72. Rosenblatt, R., Principles of Neurodynamics, Spartan Books, New York, 1962.

73. Rumelhart, D.E., McClelland, J.L., and The PDP Research Group, Parallel Distributed Processing Explorations in the Microstructures of Cognition Vol. 1:Foundations, MIT Press, Cambridge, Mass., 1988.

74. Scardino PT. Early detection of prostate cancer. Urol Clin North America 16: 635-655, 1989.

75. Sejnowski, T.J. and Rosenberg, C.M., "Parallel Networks that Learn to Pronounce English Text," Complex Systems, 1, 145-168.

76. Shankey, VT, Kallioniemi, O-P, Koslowski, JM, Leiber, ML, Mayall, BH, Miller, G, and Smith GJ. Consensus review of the clinical utility of DNA content cytometry in prostate cancer. Cytometry, 14: 497-500, 1993.

77. Thompson IM, Brawley O, and Kramer B. Chemoprevention in carcinoma of the prostate. Oncology 7 (Supplement), 49-53, 1993.

78. Van Gool, L., Dewaele, P., and Oosterlinck, A., 1983, "Texture Analysis Anno 1983," *Computer Vision, Graphic, and Image Processing*, 29, pp. 336-357.

79. Vogh, J. and Ashenayi, K., "A Solution to the Perceptron XOR Problem With a Gaussian Function," in the proceedings of the 1989 Southeastern Simulation Conference, Pensacola, Florida, pp. 7-12, October 16-17, 1989.

80. Walsh, P.C. and Jewett, H.J. Radical surgery for prostatic cancer. Cancer, 45:1906, 1980.

81. Wasserman, Phillip D. Neural Computing Theory and Practice, Van Nostrand and Reinhold, New York, 1989.

82. Werbos, P.J., "Beyond Regression: New Tools for Prediction and Analysis in the Behavioral Sciences," Ph.D. Thesis, Harvard University, 1974.

What is claimed is:

1. A method of predicting prostate cancer progression, comprising:
   (a) obtaining prostate cells from a subject;
   (b) analyzing predictive parameters in the prostate cells, wherein the predictive parameters are nuclear morphometric descriptors, including: object sum optical density, picograms of DNA, contrast, correlation, sum average, sum variance, difference variance, difference entropy, information measure B, product moment, standard deviation, and DNA ploidy; and
   (c) predicting cancer progression by statistical analysis of the predictive parameters, where the statistical analysis is logistic regression, discriminate analysis, recursive partitioning, neural network, or classification and regression tree analysis.

2. The method of claim 1, wherein the nuclear morphometric descriptors are selected from the group consisting of object sum optical density, object shape, picograms of DNA, contrast, correlation, inverse difference moment, sum average, sum variance, difference variance, difference entropy, information measure B, product moment, standard deviation, and DNA ploidy.

3. The method of claim 1, wherein the nuclear morphometric descriptors are selected from the group consisting of object sum optical density, object size, object shape, picograms of DNA, angular second moment, contrast, correlation, difference moment, inverse difference moment, sum average, sum variance, sum entropy, entropy, difference variance, difference entropy, information measure A, information measure B, maximal correlation coefficient, coefficient of variation, peak transition probability, diagonal variance, diagonal moment, second diagonal moment, product moment, triangular symmetry, blobness, standard deviation, and DNA ploidy.

4. The method of claim 1, wherein the predictive parameters further include Post-op Gleason.

5. The method of claim 4, wherein the predictive parameters further include PD-41 antigenic expression and Her-2-neu antigenicity.

6. The method of claim 1, wherein the nuclear morphometric descriptors are Markovian nuclear texture features.

7. The method of claim 1, wherein the statistical analysis is univariate or multivariate analysis.

8. The method of claim 7, wherein the statistical analysis is multivariate analysis.

9. A method for predicting the recurrence of prostate cancer following radical prostatectomy comprising the steps of:
   (a) obtaining prostate cells from a subject;
   (b) generating nuclear morphometric descriptors for the cells, including: object sum optical density, picograms of DNA, contrast, correlation, sum average, sum variance, difference variance, difference entropy, information measure B, product moment, standard deviation, and DNA ploidy; and
   (c) predicting the recurrence of prostate cancer in the cell samples by statistical analysis of the nuclear morphometric descriptors, where the statistical analysis is logistic regression, discriminate analysis, recursive partitioning, neural network, or classification and regression tree analysis.

10. The method of claim 9, wherein the statistical analysis is multivariate statistical analysis.

11. The method of claim 10, further comprising statistical analysis of predictive parameters selected from the group consisting of Post-op Gleason, nuclear roundness variance, PD-41 antigenic expression and Her-2-neu antigenic expression.

12. The method of claim 11, wherein the nuclear morphometric descriptors are Markovian nuclear texture features.

13. A method of predicting the occurrence of fatal metastatic prostate disease comprising the steps of:
   (a) obtaining prostate cells from a subject;
   (b) generating nuclear morphometric descriptors for the cells, including: object sumn optical density, picograms of DNA, contrast, correlation, sum average, sum variance, difference variance, difference entropy, information measure B, product moment, and standard deviation; and
   (c) predicting the occurrence of fatal metastatic prostate disease by statistical analysis of the nuclear morphometric descriptors.

14. The method of claim 13, further comprising statistical analysis of predictive parameters selected from the group consisting of post-op Gleason DNA ploidy, PD-41 antigenic expression, or Her-2-neu antigenic expression.

15. The method of claim 14, wherein the predictive parameter is Her-2-neu antigenic expression.

16. A method of predicting the progression of prostate cells from a normal state to a malignant state comprising the steps of:
   (a) obtaining prostate cells from a subject;
   (b) generating nuclear morphometric descriptors for the cells;
   (c) analyzing selected cell biomarkers; and
   (d) predicting the progression of the cells by using multivariate statistical modeling of the nuclear morphometric descriptors and the selected biomarkers.

17. The method of claim 16, wherein the selected biomarkers are PD-41 antigenic expression and Her-2-neu antigenic expression.

18. The method of claim 16, wherein the nuclear morphometric descriptors include Markovian texture features.

19. A method of determining prostate cancer progression comprising: (a) providing a neural network;
   (b) training the neural network using predictive parameters, obtained from prostate cells known to progress and a set of predictive parameters obtained from prostate cells known not to progress, the predictive parameters comprising nuclear morphometric descriptors;
   (c) analyzing dredictive parameters in tumor cells of an individual having an unknown state of cancer progression; and
   (d) predicting cancer progression in cells of the individual having an unknown state of cancer progression using the predictive parameters and the trained neural network.

20. The method of claim 19, wherein the nuclear morphometric descriptors are selected from the group consisting of object sum optical density, object shape, picograms of DNA, contrast, correlation, inverse difference moment, sum average, sum variance, difference variance, difference entropy, information measure B, product moment, standard deviation, and DNA ploidy.

21. The method of claim 19, wherein the nuclear morphometric descriptors are selected from the group consisting of object sum optical density, object size, object shape, picograms of DNA, angular second moment, contrast, correlation, difference moment, inverse difference moment, sum average, sum variance, sum entropy, entropy, difference variance, difference entropy, information measure A, information measure B, maximal correlation coefficient, coefficient of variation, peak transition probability, diagonal variance, diagonal moment, second diagonal moment, product moment, triangular symmetry, blobness, standard deviation, and DNA ploidy.

22. The method of claim 19, wherein the neural network is of the back propagation type.

23. The method of claim 19, wherein the neural network is of a hybrid type.

24. The method of claim 19, wherein the prognostic parameters of step (b) further include post operative Gleason score, PD-41 antigenic expression, or Her-2-neu antigenic expression.

25. The method of claim 1, 9 or 13, further comprising analyzing one or more nuclear morphometric descriptors selected from the group consisting of object size, object shape, angular second moment, difference moment, inverse difference moment, sum entropy, entropy, information measure A, maximal correlation coefficient, coefficient of variation, peak transition probability, diagonal variance, diagonal moment, second diagonal moment, triangular symmetry, perimeter, DNA index, density, average optical density, feret X, feret Y, maximum diameter, minimum diameter and elongation.

26. The method of claim 16 or claim 19, wherein the nuclear morphometric descriptors are selected from the group consisting of object sum optical density, object size, object shape, picoprams of DNA, angular second moment, contrast, correlation, difference moment, inverse difference moment, sum average, sum variance, sum entropy, entropy, difference variance, difference entropy, information measure A, information measure B, maximal correlation coefficient, coefficient of variation, peak transition probability, diagonal variance, diagonal moment, second diagonal moment, product moment, triangular symmetry, standard deviation, DNA ploidy, perimeter, DNA index, density, average optical density, feret X, feret Y, maximum diameter, minimum diameter and elongation.

27. A method of predicting the progression of prostate cancer comprising the steps of:
 (a) obtaining prostate cells from a subject;
 (b) analyzing predictive parameters from the prostate cells, the predictive parameters including nuclear morphometric descriptors;
 (c) utilizing statistical analysis to determine multivariately significant nuclear morphometric descriptors to calculate a quantitative nuclear grade; and
 (d) predicting the probability of progression in the patient by statistical analysis of the quantitative nuclear grade.

28. The method of claim 27, further including the steps of analyzing predictive parameters from the prostate cells including utilizing statistical analysis to determine univariately significant patient derived pathology and clinical information variables that contribute to a multivariate model solution and predicting the probability of progression in the patient by further statistical analysis of the quantitative nuclear grade and urivariately significant patient derived pathology and clinical information variables.

29. The method of claim 27, wherein the nuclear morphometric descriptors include Markovian nuclear texture features.

30. The method of claim 13 or claim 16, wherein the statistical analysis is logistic regression, discriminate analysis, recursive partitioning, classification and regression tree analysis, or neural network.

31. The method according to claim 17, wherein the patient derived pathology and clinical information variables are selected from the group consisting of post operative Gleason score, serum PSA, PD-41 antigenic expression, or Her-2-neu antigenic expression.

* * * * *